US012700493B2

(12) United States Patent
Fernandes et al.

(10) Patent No.: US 12,700,493 B2
(45) Date of Patent: Aug. 4, 2026

(54) AUTOMATED IMAGING PROTOCOL MANAGEMENT FOR HYBRID MODALITIES

(71) Applicant: GE Precision Healthcare LLC, Waukesha, WI (US)

(72) Inventors: Angelo Fernandes, Bangalore (IN); Ann Jose, Bangalore (IN); Manpreet Singh, Bangalore (IN); Adarsh V. Nath, Bangalore (IN); Anoop Thomas, Bangalore (IN); Veeresh Badiginchula, Bangalore (IN); Marina Mesh, Haifa (IL); Uzi Dror, Haifa (IL)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 364 days.

(21) Appl. No.: 18/508,837

(22) Filed: Nov. 14, 2023

(65) Prior Publication Data
US 2024/0177830 A1 May 30, 2024

(30) Foreign Application Priority Data
Nov. 24, 2022 (IN) .............................. 202241067702

(51) Int. Cl.
| | |
|---|---|
| *G06K 9/00* | (2022.01) |
| *G06T 7/00* | (2017.01) |
| *G16H 30/20* | (2018.01) |

(52) U.S. Cl.
CPC ........... *G16H 30/20* (2018.01); *G06T 7/0012* (2013.01); *G06T 2207/10008* (2013.01)

(58) Field of Classification Search
USPC ....... 382/100, 128–133, 155, 162, 168, 173, 382/181, 254, 305; 600/410
See application file for complete search history.

(56) References Cited

U.S. PATENT DOCUMENTS

| | | | | |
|---|---|---|---|---|
| 11,894,123 | B2 * | 2/2024 | Fishman ................ | G16H 30/20 |
| 2005/0206967 | A1 * | 9/2005 | Viswanth ............... | G16H 30/20 |
| | | | | 358/448 |
| 2008/0255443 | A1 * | 10/2008 | Piron ..................... | A61B 5/055 |
| | | | | 600/410 |
| 2017/0195377 | A1 * | 7/2017 | Ahmed ................ | H04L 51/046 |

(Continued)

*Primary Examiner* — Seyed H Azarian
(74) *Attorney, Agent, or Firm* — Amin, Turocy & Watson, LLP

(57) ABSTRACT

Systems or techniques that facilitate automated imaging protocol management for hybrid modalities are provided. In various embodiments, a system can electronically access a first medical imaging scanner and a second medical imaging scanner, wherein the first medical imaging scanner and the second medical imaging scanner can be of different image-capture modalities. In various aspects, the system can electronically perform automated imaging protocol management across the first medical imaging scanner and the second medical imaging scanner. In various instances, such automated imaging protocol management can comprise: hybrid-aware scanner registration management; hybrid-aware protocol dependency management; hybrid-aware protocol commit management; hybrid-aware remote protocol marking management; hybrid-aware protocol restore management; hybrid-aware protocol editing management; or hybrid-aware scanner-protocol incompatibility management.

18 Claims, 26 Drawing Sheets

(56)                    References Cited

U.S. PATENT DOCUMENTS

| | | | | |
|---|---|---|---|---|
| 2018/0144823 A1* | 5/2018 | Raman | .................. | A61B 6/545 |
| 2018/0294052 A1* | 10/2018 | Fishman | ........... | G06Q 10/1093 |
| 2021/0196219 A1* | 7/2021 | Jansen | .................. | A61B 6/037 |

* cited by examiner

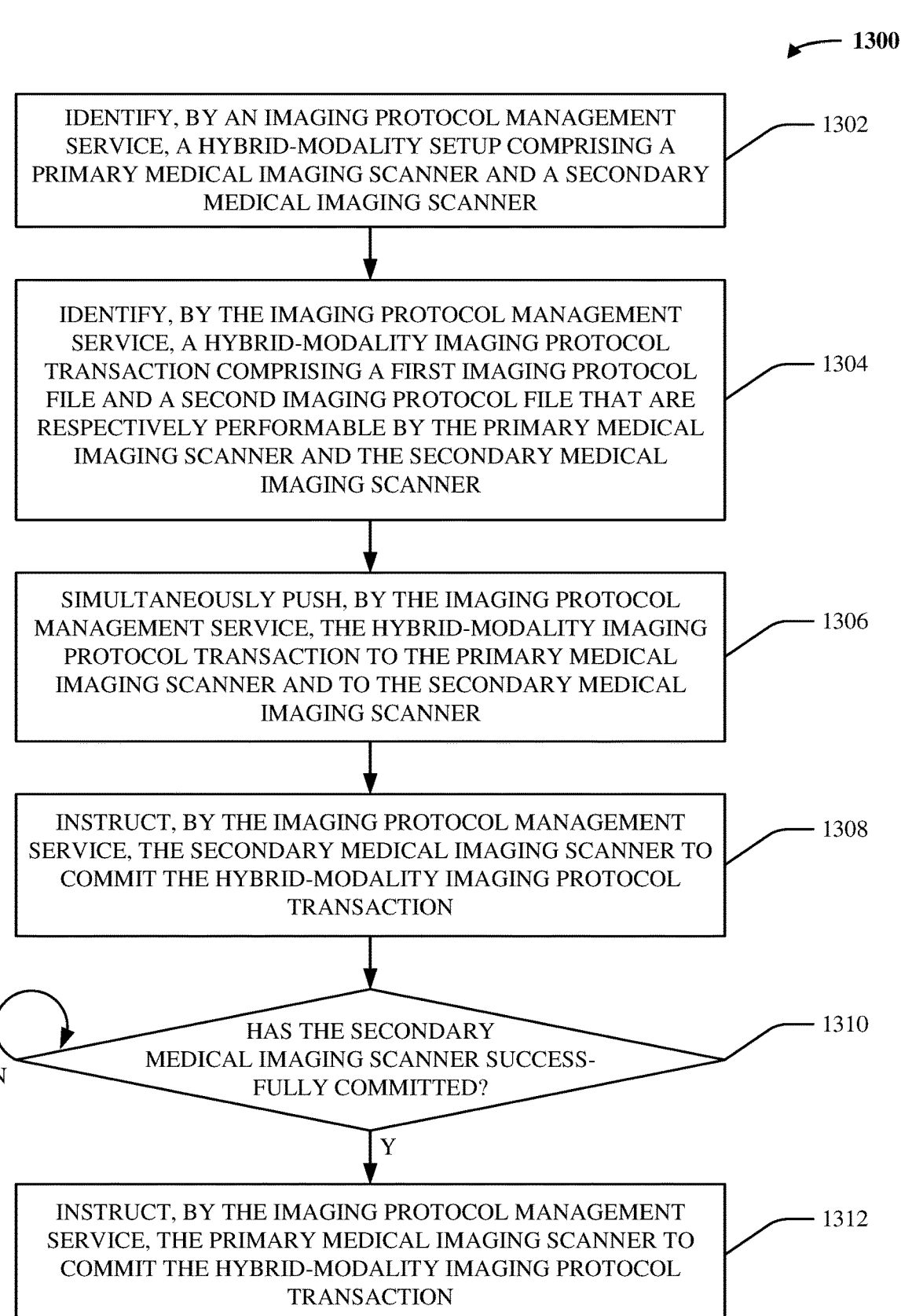

1300

1302 — IDENTIFY, BY AN IMAGING PROTOCOL MANAGEMENT SERVICE, A HYBRID-MODALITY SETUP COMPRISING A PRIMARY MEDICAL IMAGING SCANNER AND A SECONDARY MEDICAL IMAGING SCANNER

1304 — IDENTIFY, BY THE IMAGING PROTOCOL MANAGEMENT SERVICE, A HYBRID-MODALITY IMAGING PROTOCOL TRANSACTION COMPRISING A FIRST IMAGING PROTOCOL FILE AND A SECOND IMAGING PROTOCOL FILE THAT ARE RESPECTIVELY PERFORMABLE BY THE PRIMARY MEDICAL IMAGING SCANNER AND THE SECONDARY MEDICAL IMAGING SCANNER

1306 — SIMULTANEOUSLY PUSH, BY THE IMAGING PROTOCOL MANAGEMENT SERVICE, THE HYBRID-MODALITY IMAGING PROTOCOL TRANSACTION TO THE PRIMARY MEDICAL IMAGING SCANNER AND TO THE SECONDARY MEDICAL IMAGING SCANNER

1308 — INSTRUCT, BY THE IMAGING PROTOCOL MANAGEMENT SERVICE, THE SECONDARY MEDICAL IMAGING SCANNER TO COMMIT THE HYBRID-MODALITY IMAGING PROTOCOL TRANSACTION

1310 — HAS THE SECONDARY MEDICAL IMAGING SCANNER SUCCESS-FULLY COMMITTED?

N

Y

1312 — INSTRUCT, BY THE IMAGING PROTOCOL MANAGEMENT SERVICE, THE PRIMARY MEDICAL IMAGING SCANNER TO COMMIT THE HYBRID-MODALITY IMAGING PROTOCOL TRANSACTION

FIG. 13

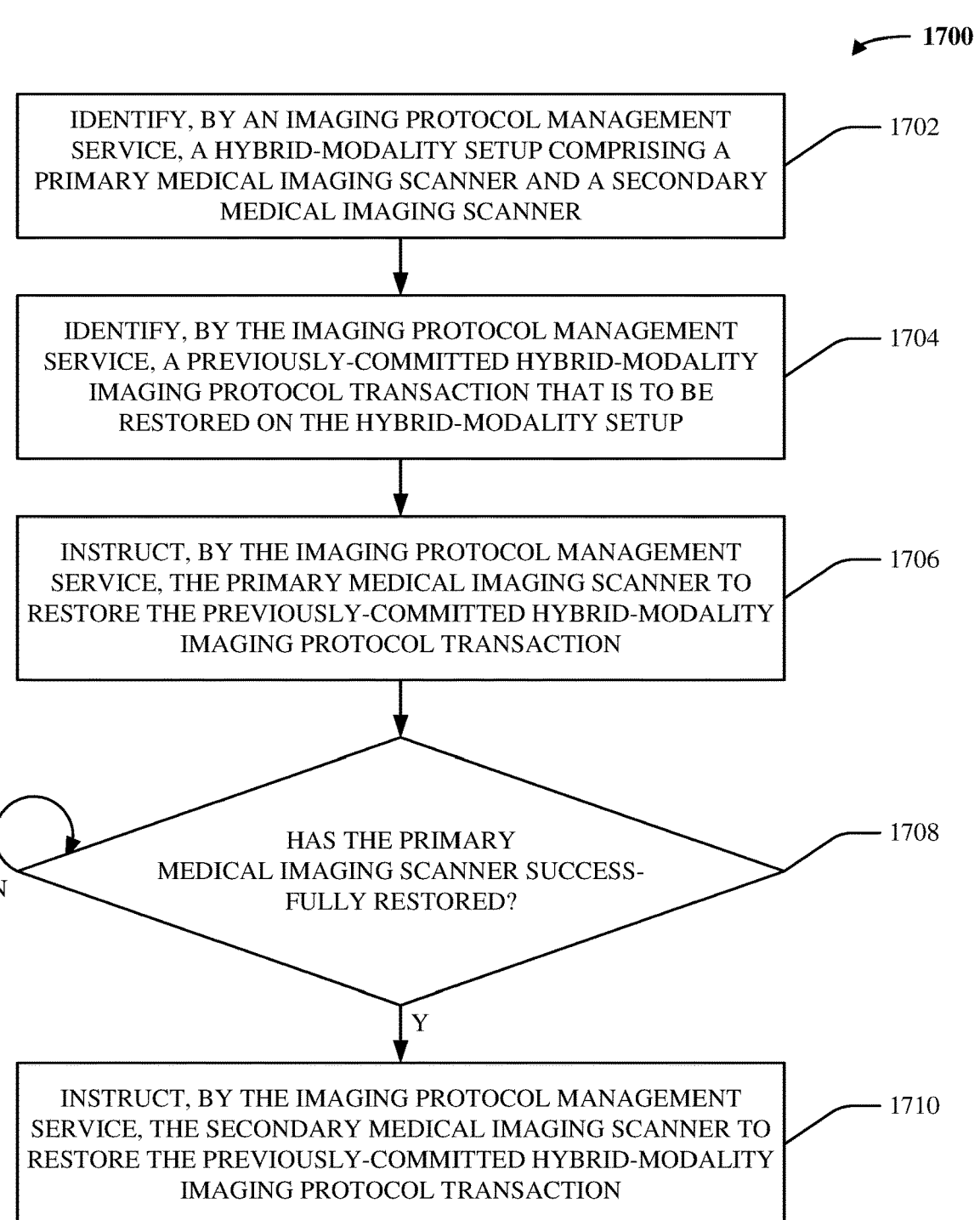

1700

IDENTIFY, BY AN IMAGING PROTOCOL MANAGEMENT SERVICE, A HYBRID-MODALITY SETUP COMPRISING A PRIMARY MEDICAL IMAGING SCANNER AND A SECONDARY MEDICAL IMAGING SCANNER — 1702

IDENTIFY, BY THE IMAGING PROTOCOL MANAGEMENT SERVICE, A PREVIOUSLY-COMMITTED HYBRID-MODALITY IMAGING PROTOCOL TRANSACTION THAT IS TO BE RESTORED ON THE HYBRID-MODALITY SETUP — 1704

INSTRUCT, BY THE IMAGING PROTOCOL MANAGEMENT SERVICE, THE PRIMARY MEDICAL IMAGING SCANNER TO RESTORE THE PREVIOUSLY-COMMITTED HYBRID-MODALITY IMAGING PROTOCOL TRANSACTION — 1706

HAS THE PRIMARY MEDICAL IMAGING SCANNER SUCCESS-FULLY RESTORED? — 1708

N

Y

INSTRUCT, BY THE IMAGING PROTOCOL MANAGEMENT SERVICE, THE SECONDARY MEDICAL IMAGING SCANNER TO RESTORE THE PREVIOUSLY-COMMITTED HYBRID-MODALITY IMAGING PROTOCOL TRANSACTION — 1710

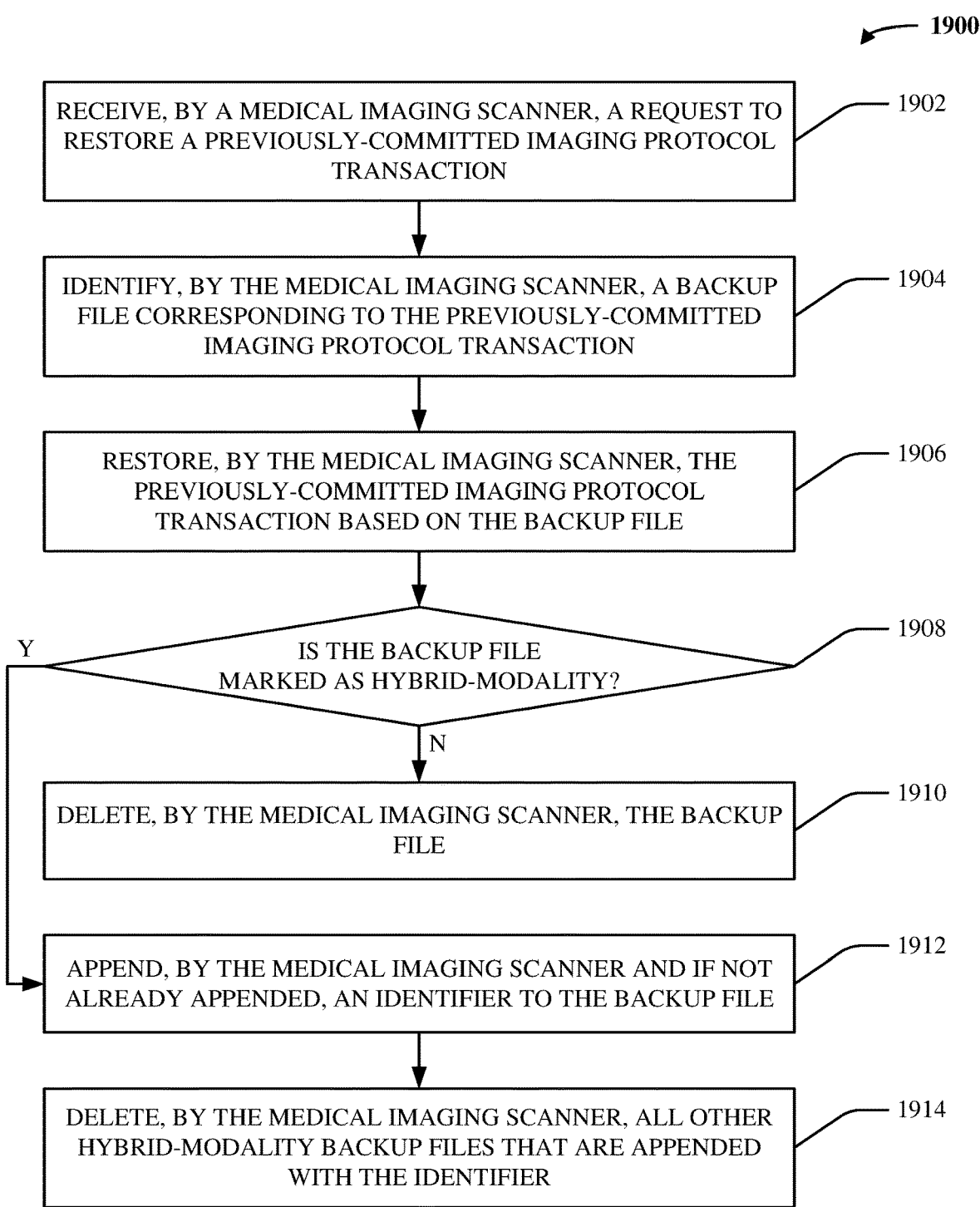

RECEIVE, BY A MEDICAL IMAGING SCANNER, A REQUEST TO RESTORE A PREVIOUSLY-COMMITTED IMAGING PROTOCOL TRANSACTION — 1902

IDENTIFY, BY THE MEDICAL IMAGING SCANNER, A BACKUP FILE CORRESPONDING TO THE PREVIOUSLY-COMMITTED IMAGING PROTOCOL TRANSACTION — 1904

RESTORE, BY THE MEDICAL IMAGING SCANNER, THE PREVIOUSLY-COMMITTED IMAGING PROTOCOL TRANSACTION BASED ON THE BACKUP FILE — 1906

IS THE BACKUP FILE MARKED AS HYBRID-MODALITY? — 1908

Y

N

DELETE, BY THE MEDICAL IMAGING SCANNER, THE BACKUP FILE — 1910

APPEND, BY THE MEDICAL IMAGING SCANNER AND IF NOT ALREADY APPENDED, AN IDENTIFIER TO THE BACKUP FILE — 1912

DELETE, BY THE MEDICAL IMAGING SCANNER, ALL OTHER HYBRID-MODALITY BACKUP FILES THAT ARE APPENDED WITH THE IDENTIFIER — 1914

FIG. 19

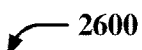
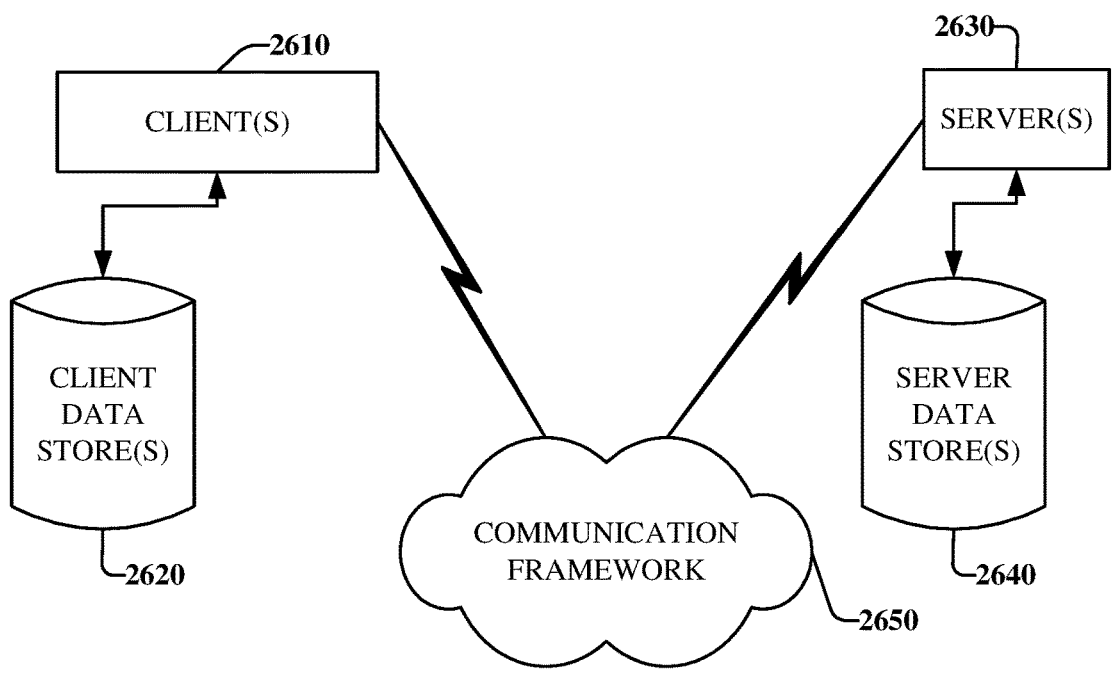
FIG. 26

AUTOMATED IMAGING PROTOCOL MANAGEMENT FOR HYBRID MODALITIES

RELATED APPLICATION

This application claims priority to India Patent Application No. 202241067702 filed Nov. 24, 2022 and titled "IMAGING PROTOCOL MANAGEMENT FOR HYBRID IMAGING SYSTEMS," the entirety of which application is incorporated herein by reference.

TECHNICAL FIELD

The subject disclosure relates generally to medical imaging scanners, and more specifically to automated imaging protocol management for hybrid modalities.

BACKGROUND

A medical imaging scanner can capture or generate a medical image by executing an imaging protocol file. A healthcare entity can employ a fleet of medical imaging scanners. Automated imaging protocol management can be implemented to help organize which imaging protocol files are executed by which medical imaging scanners in the fleet. Some medical imaging scanners in the fleet can be grouped together in hybrid-modality setups. Unfortunately, existing techniques for facilitating automated imaging protocol management do not account for such hybrid-modality setups.

Accordingly, systems or techniques that can address one or more of these technical problems can be desirable.

SUMMARY

The following presents a summary to provide a basic understanding of one or more embodiments. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus or computer program products that facilitate automated imaging protocol management for hybrid modalities are described.

According to one or more embodiments, a system is provided. The system can comprise a non-transitory computer-readable memory that can store computer-executable components. The system can further comprise a processor that can be operably coupled to the non-transitory computer-readable memory and that can execute the computer-executable components stored in the non-transitory computer-readable memory. In various embodiments, the computer-executable components can comprise an access component that can electronically access a first medical imaging scanner and a second medical imaging scanner, wherein the first medical imaging scanner and the second medical imaging scanner can be of different image-capture modalities. In various aspects, the computer-executable components can comprise a manager component that can electronically perform imaging protocol management across the first medical imaging scanner and the second medical imaging scanner. In various instances, such imaging protocol management can comprise: hybrid-aware scanner registration management; hybrid-aware protocol dependency management; hybrid-aware protocol commit management; hybrid-aware remote protocol marking management; hybrid-aware protocol restore management; hybrid-aware protocol editing management; or hybrid-aware scanner-protocol incompatibility management.

According to one or more embodiments, a computer-implemented method is provided. In various embodiments, the computer-implemented method can comprise electronically accessing, by a device operatively coupled to a processor, a first medical imaging scanner and a second medical imaging scanner, wherein the first medical imaging scanner and the second medical imaging scanner can be of different image-capture modalities. In various aspects, the computer-implemented method can comprise electronically performing, by the device, automated imaging protocol management across the first medical imaging scanner and the second medical imaging scanner. In various instances, such automated imaging protocol management can comprise: hybrid-aware scanner registration management; hybrid-aware protocol dependency management; hybrid-aware protocol commit management; hybrid-aware remote protocol marking management; hybrid-aware protocol restore management; hybrid-aware protocol editing management; or hybrid-aware scanner-protocol incompatibility management.

According to one or more embodiments, a computer program product for facilitating automated imaging protocol management for hybrid modalities is provided. In various embodiments, the computer program product can comprise a non-transitory computer-readable memory having program instructions embodied therewith. In various aspects, the program instructions can be executable by a processor to cause the processor to electronically access a first medical imaging scanner and a second medical imaging scanner, wherein the first medical imaging scanner and the second medical imaging scanner can be of different image-capture modalities. In various instances, the program instructions can be further executable to cause the processor to electronically perform automated imaging protocol management across the first medical imaging scanner and the second medical imaging scanner. In various cases, such automated imaging protocol management can comprise: hybrid-aware scanner registration management; hybrid-aware protocol dependency management; hybrid-aware protocol commit management; hybrid-aware remote protocol marking management; hybrid-aware protocol restore management; hybrid-aware protocol editing management; or hybrid-aware scanner-protocol incompatibility management.

DESCRIPTION OF THE DRAWINGS

FIG. 13 illustrates a flow diagram of an example, non-limiting computer-implemented method that facilitates hybrid-aware protocol commit management in accordance with one or more embodiments described herein.

FIGS. 17-19 illustrate flow diagrams of example, non-limiting computer-implemented methods that facilitate hybrid-aware protocol restore management in accordance with one or more embodiments described herein.

FIG. 26 illustrates an example networking environment operable to execute various implementations described herein.

DETAILED DESCRIPTION

Figure 1:
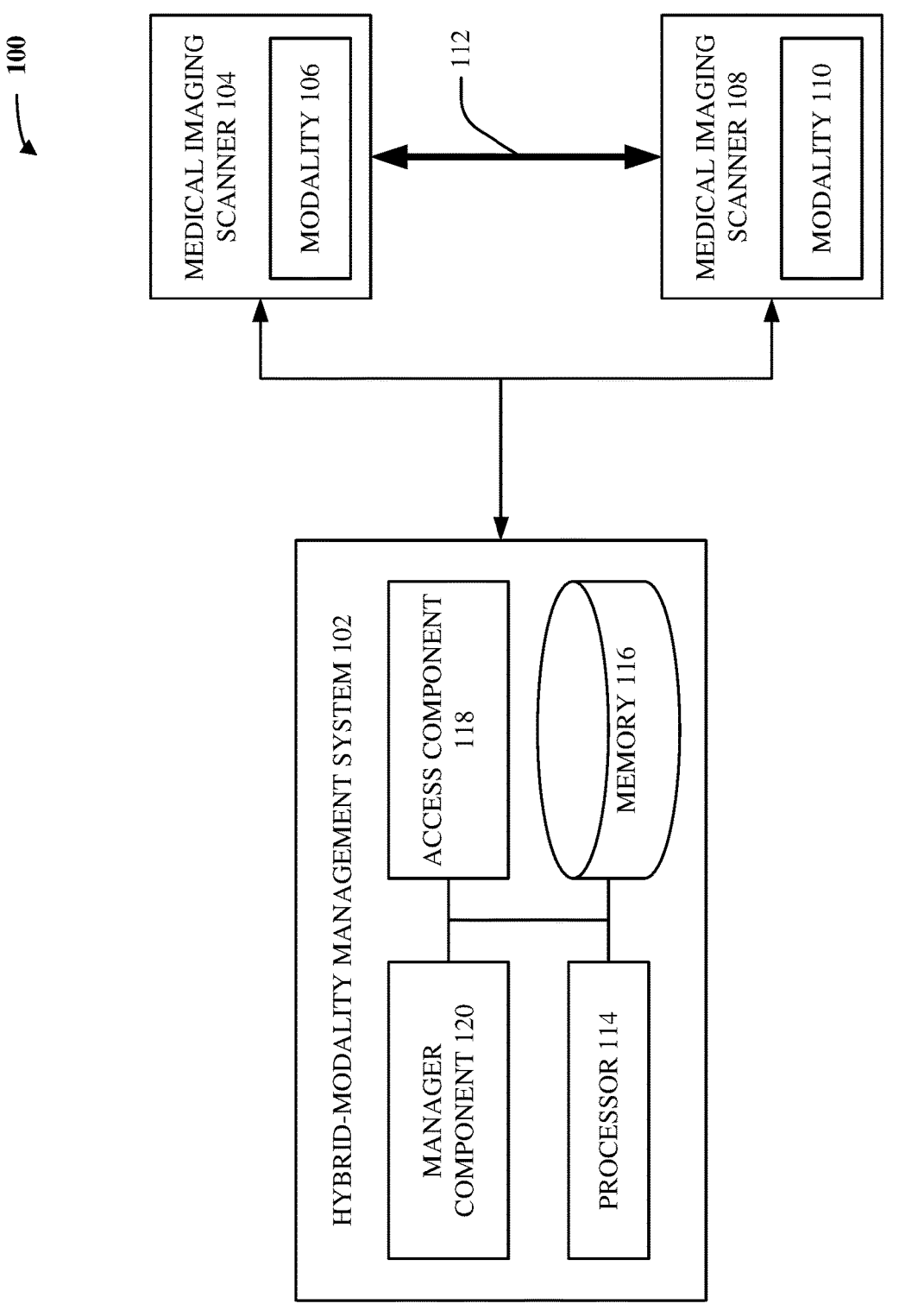
FIG. 1 illustrates a block diagram of an example, non-limiting system that facilitates automated imaging protocol management for hybrid modalities in accordance with one or more embodiments described herein.

The following detailed description is merely illustrative and is not intended to limit embodiments or application/uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A medical imaging scanner (e.g., a computed tomography (CT) scanner, a magnetic resonance imaging (MRI) scanner, an X-ray scanner, an ultrasound scanner, a positron emission tomography (PET) scanner, a nuclear medicine (NM) scanner) can capture or generate a medical image (e.g., a CT scanned image, an MRI scanned image, an X-ray scanned image, an ultrasound scanned image, a PET scanned image, an NM scanned image) by executing an imaging protocol file.

An imaging protocol file can be any suitable electronic data that specifics or defines image-acquisition or image-processing steps, parameters, or actions which, when implemented by a suitable medical imaging scanner, can yield one or more medical images. As some non-limiting examples, an imaging protocol file can specify or define one or more scanning planes to be implemented by a medical imaging scanner, one or more tube currents or voltages to be implemented by a medical imaging scanner, one or more filters or kernels to be implemented by a medical imaging scanner, one or more gantry speeds or spans to be implemented by a medical imaging scanner, or one or more patient table heights to be implemented by a medical imaging scanner.

In various cases, an imaging protocol transaction can be a discrete, time-stamped electronic transaction which requests or commands a medical imaging scanner to do something with respect to one or more imaging protocol files (e.g., to transmit or receive one or more imaging protocol files, to commit one or more imaging protocol files, to restore one or more imaging protocol files).

Imaging protocol files can vary across image-capture modalities, even if such files are designed or intended to visualize the same anatomical structure (e.g., organ, tissue, body party, body fluid, body cavity) as each other. For instance, suppose that a medical imaging scanner A belongs to a CT image-capture modality, and suppose that a medical imaging scanner B belongs to an NM image-capture modality. CT scanners can have different image-acquisition or image-processing steps, actions, or parameters than NM scanners. Accordingly, capturing a CT scanned image of a patient's brain using the medical imaging scanner A can require some particular imaging protocol file, and capturing an NM scanned image of the patient's brain using the medical imaging scanner B can require a different imaging protocol file.

Likewise, imaging protocol files can vary across scanner models, even if such files are designed or intended to visualize the same anatomical structure as each other. For instance, suppose that a medical imaging scanner C and a medical imaging scanner D both belong to a PET image-capture modality, but suppose that the medical imaging scanner C and the medical imaging scanner D have different model numbers (e.g., have different PET hardware or different PET software than each other). Different PET scanner models can have different image-acquisition or image-processing steps, actions, or parameters. Accordingly, capturing a PET scanned image of the patient's head using the medical imaging scanner C can require some specific imaging protocol file, and capturing a PET scanned image of the patient's head using the medical imaging scanner D can require yet a different imaging protocol file.

A healthcare entity (e.g., a hospital, a clinic) can employ a fleet of medical imaging scanners (e.g., tens, hundreds, or thousands of medical imaging scanners). Because imaging protocol files can vary across both image-capture modality and scanner model, and because different imaging protocol files can be required for different patients, in different localities, at different times, or to comply with different regulatory restrictions, organizing or distributing imaging protocol files among the fleet can be a daunting, non-trivial task.

Automated imaging protocol management can be implemented to help efficiently organize or control which imaging protocol files are implemented by which medical imaging scanners in the fleet. Existing techniques facilitate automated imaging protocol management via a cloud-based protocol manager. In particular, medical imaging scanners in the fleet can be registered with the cloud-based protocol manager. The cloud-based protocol manager can automatically import (e.g., pull) imaging protocol files from the registered scanners to a cloud-based protocol library. Users or technicians (e.g., radiologists, clinicians, medical researchers) can access the cloud-based protocol manager from a computing device (e.g., workstation, desktop computer, laptop computer, smart phone) to view or edit whatever imaging protocol files are stored in the cloud-based protocol library. The cloud-based protocol manager can distribute (e.g., push) various imaging protocol files from the cloud-based protocol library to selected or desired ones of the registered scanners. The cloud-based protocol manager can also track or monitor deviations between imaging protocol files implemented on the registered scanners and imaging protocol files stored in the cloud-based protocol library. Accordingly, the cloud-based protocol manager can be considered as automatically organizing (e.g., managing) which imaging protocol files are implemented on which medical imaging scanners in the fleet. Such automatic organization can help to reduce instances in which incorrect or non-regulatory-compliant imaging protocol files are erroneously or mistakenly implemented in the fleet.

Now, some medical imaging scanners in the fleet can be grouped together in hybrid-modality setups. A hybrid-modality setup can be a group of two or more physically-close-together medical imaging scanners that belong to different image-capture modalities but that nevertheless work in tandem to achieve a common, concerted, or consolidated clinical objective or outcome. For example, suppose that a medical imaging scanner E belonging to an NM image-capture modality and a medical imaging scanner F belonging to a CT image-capture modality together form a hybrid-modality setup. In such case, the medical imaging scanner E and the medical imaging scanner F can be physically present in the same hospital room as each other, such that a patient can be scanned first by the medical imaging scanner F, thereby yielding a CT scanned image of the patient, and shortly thereafter (e.g., seconds or minutes later) by the medical imaging scanner E, thereby yielding an NM scanned image of the patient. Moreover, the NM scanned image can depend upon the CT scanned image. That is, the medical imaging scanner E can be communicatively coupled to the medical imaging scanner F, such that the medical imaging scanner E can generate the NM scanned image based on the CT scanned image (e.g., the medical imaging scanner E can orient, align, or alter its gantry, table, or tube settings based on the CT scanned image or based on the gantry, table, or tube settings used by the medical imaging scanner F; the medical imaging scanner E can superimpose the NM scanned image overtop of or adjacent to the CT scanned image). In this way, the medical imaging scanner E and the medical imaging scanner F can be considered as working together in tandem to scan the patient.

Unfortunately, existing techniques for facilitating automated imaging protocol management do not account for such hybrid-modality setups. In particular, as recognized by the inventors of various embodiments described herein, such existing techniques treat each medical imaging scanner in isolation. That is, the cloud-based protocol manager of existing techniques pulls imaging protocol files from, pushes imaging protocol files to, or otherwise interacts with imaging protocol files pertaining to any given medical imaging scanner, without regard to the imaging protocol files that have been pulled from, that have been pushed to, or that pertain to any other medical imaging scanner. In other words, the cloud-based protocol manager of existing techniques performs imaging protocol transactions with the given medical imaging scanner, without regard to what other imaging protocol transactions have been performed with related medical imaging scanners. If the given medical imaging scanner is a member of a hybrid-modality setup, such isolated treatment can disrupt the proper operation of the hybrid-modality setup. In particular, which imaging protocol files the given medical imaging scanner is supposed to implement can depend upon, or can be depended upon by, which imaging protocol files are implemented by the other medical imaging scanners in the hybrid-modality setup. Because existing techniques fail to take the imaging protocol files of those other medical imaging scanners into account when managing or organizing the imaging protocol files of the given medical imaging scanner, such existing techniques can cause the hybrid-modality setup to suffer protocol inconsistencies. Such protocol inconsistencies prevent the hybrid-modality setup from properly performing scans, and such protocol inconsistencies often go undetected until a scan is actually attempted on a patient.

For instance, consider again the medical imaging scanner E and the medical imaging scanner F mentioned above. Suppose that an imaging protocol file of the medical imaging scanner E assumes that the medical imaging scanner F implements a specific imaging protocol file. If that assumption is incorrect (e.g., if the medical imaging scanner F implements an imaging protocol file that is inconsistent with that of the medical imaging scanner E), then the hybrid-modality setup formed by the medical imaging scanner E and the medical imaging scanner F cannot function properly. Unfortunately, because existing techniques treat the medical imaging scanner E and the medical imaging scanner F separately in isolation, such existing techniques significantly increase the likelihood of that assumption being incorrect (e.g., significantly increase the probability of inconsistent imaging protocol files being mistakenly implemented by the hybrid-modality setup formed by the medical imaging scanner E and the medical imaging scanner F).

Accordingly, systems or techniques that can address one or more of these technical problems can be desirable.

Various embodiments described herein can address one or more of these technical problems. One or more embodiments described herein can include systems, computer-implemented methods, apparatus, or computer program products that can facilitate automated imaging protocol management for hybrid modalities. In particular, various embodiments described herein can involve a cloud-based protocol manager that explicitly accounts for hybrid-modality setups. In other words, when pulling, pushing, or otherwise interacting with imaging protocol files corresponding to a particular medical imaging scanner (e.g., when performing imaging protocol transactions with the particular medical imaging scanner), the cloud-based protocol manager can be configured to alter or constrain such pulling, pushing, or interacting based on whether or not that particular medical imaging scanner is a member of a hybrid-modality setup. Specifically, in some cases, the cloud-based protocol manager can pull imaging protocol files from each medical imaging scanner of a hybrid-modality setup (e.g., in some instances, this can be a simultaneous pull), and the cloud-based protocol manager can automatically analyze those pulled imaging protocol files to ensure that they are consistent with each other. If any protocol inconsistency is detected, the cloud-based protocol manager can generate an appropriate alert or warning to notify a user or technician. Similarly, the cloud-based protocol manager can push imaging protocol files to each medical imaging scanner of the hybrid-modality setup (e.g., in some instances, this can be a simultaneous push), but such push can be conditioned on those imaging protocol files being consistent with each other. So, prior to such push, the cloud-based protocol manager can analyze those imaging protocol files to ensure that they are consistent with each other, the cloud-based protocol manager can perform the push in response to no protocol inconsistencies being detected, and the cloud-based protocol manager can instead prohibit the push in response to at least one protocol inconsistency being detected. Accordingly, various embodiments described herein can detect or avoid situations in which inconsistent imaging protocol files are implemented on a hybrid-modality setup, unlike existing techniques for facilitating automated imaging protocol management.

However, this is a mere non-limiting example. Various embodiments described herein can further improve automated imaging protocol management for hybrid modalities, by making various other protocol management features cognizant of hybrid-modality setups. As described herein, this can include: making scanner registration automatically cognizant of hybrid-modality setups; making protocol commit instructions automatically cognizant of hybrid-modality setups; making local protocol markings automatically cognizant of hybrid-modality setups; making protocol or transaction restore instructions automatically cognizant of hybrid-modality setups; or making protocol editing instructions automatically cognizant of hybrid-modality setups.

Various embodiments described herein can be considered as a computerized tool (e.g., any suitable combination of computer-executable hardware or computer-executable software) that can facilitate automated imaging protocol management for hybrid modalities. In various aspects, such computerized tool can comprise an access component or a manager component.

In various embodiments, there can be a first medical imaging scanner and a second medical imaging scanner. In various aspects, the first medical imaging scanner can belong to any suitable image-capture modality (e.g., a CT image-capture modality, an MRI image-capture modality, an X-ray image-capture modality, an ultrasound image-capture modality, a PET image-capture modality, an NM image-capture modality) and can comprise any suitable human-computer interface devices (e.g., keyboard, keypad, touch-screen, voice command system). Likewise, the second medical imaging scanner can belong to any suitable image-capture modality and can comprise any suitable human-computer interface devices. However, the image-capture modality of the second medical imaging scanner can be different from that of the first medical imaging scanner. Moreover, in various cases, the first medical imaging scanner and the second medical imaging scanner can be communicatively coupled together (e.g., via any suitable wired or wireless electronic connection) or can be within any suitable threshold proximity of each other (e.g., physically located in the same hospital room as each other). Accordingly, the first medical imaging scanner and the second medical imaging scanner can collectively be considered as forming a hybrid-modality setup, such that they can work in tandem to achieve a clinical outcome for any given medical patient.

In various embodiments, the access component of the computerized tool can electronically access the first medical imaging scanner or the second medical imaging scanner. For instance, the access component can electronically communicate with (e.g., transmit data to, receive data from) the first medical imaging scanner or the second medical imaging scanner. In any case, the access component can be considered as a conduit through which or via which other components of the computerized tool can electronically interact with the first medical imaging scanner or with the second medical imaging scanner.

In various embodiments, the manager component of the computerized tool can electronically manage, control, organize, synchronize, or otherwise orchestrate imaging protocol files for the first medical imaging scanner or for the second medical imaging scanner, as described herein. In particular, the manager component can electronically store, maintain, control, or otherwise access an imaging protocol library. In various aspects, the imaging protocol library can comprise any suitable number of imaging protocol files. In various instances, the imaging protocol library can collate such imaging protocol files according to image-capture modality or according to scanner model. Moreover, in various cases, for each given imaging protocol file, the imaging protocol library can indicate one or more other imaging protocol files that belong to different image-capture modalities or to different scanner models, but that nevertheless are clinical substitutes for the given imaging protocol file (e.g., that nevertheless are designed or intended to visualize a same anatomical structure for a same clinical purpose as the given imaging protocol file). In various aspects, the manager component can pull imaging protocol files from the first medical imaging scanner or from the second medical imaging scanner to the imaging protocol library, or the manager component can push imaging protocol files from the imaging protocol library to the first medical imaging scanner or to the second medical imaging scanner. Furthermore, in various instances, the manager component can comprise or otherwise implement any suitable graphical user interface (e.g., can be a web-accessible interface). In various cases, the graphical user interface can enable a user or technician to manually access, consider, or edit any imaging protocol files stored in the imaging protocol library. Further still, in various aspects, the graphical user interface can enable the user or technician to register the first medical imaging scanner or the second medical imaging scanner with the manager component and to manually select which imaging protocol files should be pulled from or pushed to the first medical imaging scanner or the second medical imaging scanner.

In various embodiments, the manager component can perform hybrid-aware scanner registration management for the first medical imaging scanner and for the second medical imaging scanner. For instance, suppose that neither the first medical imaging scanner nor the second medical imaging scanner is initially registered with the manager component. That is, the manager component can initially not have any information or metadata pertaining to the first medical imaging scanner or to the second medical imaging scanner (e.g., the manager component can initially not know the names, image-capture modalities, model numbers, software versions, or physical locations of the first medical imaging scanner and of the second medical imaging scanner). Without loss of generality, a user or technician can cause (e.g., by interacting with the graphical user interface of the manager component) the first medical imaging scanner to become registered with the manager component (e.g., the user or technician can input to the manager component the name, image-capture modality, model number, software version, or physical location of the first medical imaging scanner). Now, in response to registration of the first medical imaging scanner, the manager component can electronically command the first medical imaging scanner to search for any other medical imaging scanners that are communicatively coupled to the first medical imaging scanner (e.g., can be facilitated via any suitable network-discovery or device-discovery techniques) or that are otherwise physically nearby the first medical imaging scanner (e.g., can be facilitated via radio frequency identification tags or beacons). In various instances, the first medical imaging scanner can respond to such search command by informing the manager component that the second medical imaging scanner is communicatively coupled to, or is physically nearby, the first medical imaging scanner. In various cases, the manager component can thus automatically designate the first medical imaging scanner and the second medical imaging scanner as forming or belonging to a hybrid-modality setup. In various aspects, the manager component can further determine that the second medical imaging scanner has not yet been registered. Accordingly, the manager component can prompt or otherwise recommend that the second medical imaging scanner become registered (e.g., can ask, via the graphical user interface, the user or technician to input the name, image-capture modality, model number, or software version of the second medical imaging scanner).

In this way, the manager component can be considered as automatically avoiding situations in which one or more medical imaging scanners of a hybrid-modality setup are mistakenly left unregistered. In stark contrast, existing techniques do not automatically detect such erroneously unregistered medical imaging scanners.

In various embodiments, the manager component can perform hybrid-aware protocol dependency management for the first medical imaging scanner and for the second medical imaging scanner. In some aspects, the manager component can perform such hybrid-aware protocol dependency management in response to a pull from the first medical imaging scanner and from the second medical imaging scanner. In other aspects, the manager component can perform such hybrid-aware protocol dependency management prior to a push to the first medical imaging scanner and to the second medical imaging scanner. In either case, the manager component can determine whether or not the dependencies of whatever imaging protocol files have been pulled from or are to be pushed to the first medical imaging scanner are consistent (e.g., valid, unbroken) with those of whatever imaging protocol files have been pulled from or are to be pushed to the second medical imaging scanner.

Specifically, an imaging protocol file can specify or reference one or more dependencies. A dependency can be considered as specifying an expected or required state, value, or content of a defined computing resource or data slot. For example, an imaging protocol file can reference as a dependency an energy session of a particular scanner, meaning that the imaging protocol file can be properly executed only if: the energy session resource or slot of that particular scanner is accessible or readable to whatever scanner executes the imaging protocol file; and the energy session resource or slot of that particular scanner has whatever state, value, or content that is specified in the imaging protocol file. If either of those conditions is not satisfied (e.g., if the energy session resource or slot of that particular scanner is not accessible or readable to whatever scanner executes the imaging protocol file; or if the actual state, value, or content of that energy session resource or slot does not match that specified in the imaging protocol file), then the dependency can be considered as being invalid or broken, and the imaging protocol file can be not properly executable. Furthermore, dependencies can be nested or daisy-chained together in parent-child fashion. For example, an imaging protocol file can reference a particular computing resource as a dependency, and that particular computing resource can itself reference some other computing resource as a dependency. In various cases, if a child dependency is invalid or broken, then its parent dependency can likewise be considered as invalid or broken. Further still, note that, in some cases, an imaging protocol file can reference as a dependency some other imaging protocol file.

Now, in various aspects, the manager component can have access to the following information: one or more first imaging protocol files that have been pulled from or that are to be pushed to the first medical imaging scanner; a first link file that indicates what computing resources or data slots are locally or remotely accessible or readable by the first medical imaging scanner; one or more first computing resource states, values, or contents that are locally-stored on the first medical imaging scanner; one or more second imaging protocol files that have been pulled from or that are to be pushed to the second medical imaging scanner; a second link file that indicates what computing resources or data slots are locally or remotely accessible or readable by the second medical imaging scanner; or one or more second computing resource states, values, or contents that are locally-stored on the second medical imaging scanner.

The manager component can utilize such information to evaluate the dependencies of the first medical imaging scanner. In particular, for each dependency that is referenced in any of the one or more first imaging protocol files and that is marked as accessible or readable in the first link file, the manager component can determine whether or not the specified state, value, or content of that dependency (and of all of its child dependencies, if any) is satisfied by: the one or more first computing resource states, values, or contents; by the one or more second imaging protocol files; or by the one or more second computing resource states, values, or contents. If so, the manager component can conclude that that dependency is valid or unbroken. If not, the manager component can instead conclude that that dependency is invalid or broken. Moreover, for each dependency that is referenced in any of the one or more first imaging protocol files and that is not marked as accessible or readable in the first link file, the manager component can conclude that that dependency is invalid or broken. Furthermore, for each dependency that is marked as accessible or readable in the first link file but that is not referenced in any of the one or more first imaging protocol files, the manager component can conclude that that dependency is valid but unused (e.g., valid but unlinked; valid but unutilized).

In like fashion, the manager component can utilize such information to evaluate the dependencies of the second medical imaging scanner. In particular, for each dependency that is referenced in any of the one or more second imaging protocol files and that is marked as accessible or readable in the second link file, the manager component can determine whether or not the specified state, value, or content of that dependency (and of all of its child dependencies, if any) is satisfied by: the one or more second computing resource states, values, or contents; by the one or more first imaging protocol files; or by the one or more first computing resource states, values, or contents. If so, the manager component can conclude that that dependency is valid or unbroken. If not, the manager component can instead conclude that that dependency is invalid or broken. Moreover, for each dependency that is referenced in any of the one or more second imaging protocol files and that is not marked as accessible or readable in the second link file, the manager component can conclude that that dependency is invalid or broken. Furthermore, for each dependency that is marked as accessible or readable in the second link file but that is not referenced in any of the one or more second imaging protocol files, the manager component can conclude that that dependency is valid but unused.

In various aspects, the manager component can visually indicate conclusions or determinations of its dependency analysis on the graphical user interface. Furthermore, if the manager component performs such dependency analysis prior to a push, the manager component can permit that push to proceed only if the dependency analysis finds that no dependency is broken or invalid. In this way, the manager component can be considered as automatically avoiding or flagging situations in which inconsistent imaging protocol files are mistakenly implemented on a hybrid-modality setup. In stark contrast, existing techniques do not automatically avoid or flag such erroneously inconsistent imaging protocol files.

In various embodiments, the manager component can perform hybrid-aware protocol commit management for the first medical imaging scanner and for the second medical imaging scanner. In other words, the manager component can automatically ensure that commit operations are performed in an appropriate order among the first medical imaging scanner and the second medical imaging scanner, so as to avoid commitment of inconsistent imaging protocol files.

In various aspects, when an imaging protocol file is pushed to a medical imaging scanner, the imaging protocol file can be considered as waiting in a not-yet-committed menu of the medical imaging scanner. While the imaging protocol file is in the not-yet-committed menu, the medical imaging scanner can be unable to execute the imaging protocol file (e.g., the imaging protocol file can be not yet selectable for execution by a user or technician). In various instances, the imaging protocol file can be transferred or moved from the not-yet-committed menu to a committed menu upon performance of a commit operation or transaction. While the imaging protocol file is in the committed menu, the medical imaging scanner can be able to execute the imaging protocol file (e.g., the imaging protocol file can now be selectable for execution by a user or technician).

Now, suppose that the manager component respectively pushes to the first medical imaging scanner and to the second medical imaging scanner a first imaging protocol file and a second imaging protocol file, where (without loss of generality) the first imaging protocol file references the second imaging protocol file as a dependency. Note that a protocol inconsistency can arise if the first imaging protocol file were committed by the first medical imaging scanner but the second imaging protocol file were not committed by the second medical imaging scanner (e.g., in such case, the first imaging protocol file would be selectable for execution on the first medical imaging scanner; but, since it relies upon the second imaging protocol file, the first imaging protocol file would not be properly executable due to the second medical imaging scanner's failure to commit the second imaging protocol file). To address this problem, the manager component can determine which imaging protocol file is referenced as a dependency (e.g., the manager component can identify which imaging protocol file is the dependee and which is the depender), and the manager component can accordingly ensure that that determined imaging protocol file is committed first (e.g., the dependee can be committed before the depender). In this example, the manager component can determine that the second imaging protocol file is referenced as a dependency by the first imaging protocol file. In response to such determination, the manager component can instruct the second medical imaging scanner to commit the second imaging protocol file, and the manager component can refrain from instructing the first medical imaging scanner to commit the first imaging protocol file. In particular, the manager component can wait to instruct the first medical imaging scanner to commit the first imaging protocol file, until after receiving a notification from the second medical imaging scanner indicating that the second imaging protocol file has been successfully committed.

In this way, the manager component can be considered as automatically avoiding erroneous commit sequences or orderings that result in protocol inconsistencies on a hybrid-modality setup. In stark contrast, existing techniques do not automatically avoid such erroneous commit sequences or orderings.

In various embodiments, the manager component can perform hybrid-aware remote protocol marking management for the first medical imaging scanner and for the second medical imaging scanner. In other words, the manager component can automatically ensure that the first medical imaging scanner and the second medical imaging scanner have proper or correct local designations for whatever imaging protocol files are pushed to them.

In particular, when an imaging protocol file is pushed to a medical imaging scanner, the medical imaging scanner can locally designate, mark, or flag that imaging protocol file as being either a single-modality protocol or a hybrid-modality protocol. If the medical imaging scanner locally designates that imaging protocol file as being single-modality, then the medical imaging scanner can prohibit any other scanners from accessing or reading that imaging protocol file (e.g., such prohibition can be indicated or reflected in the link files of those other scanners). In contrast, if the medical imaging scanner instead locally designates that imaging protocol file as being hybrid-modality, then the medical imaging scanner can permit other scanners to access or read that imaging protocol file (e.g., such permission can be indicated or reflected in the link files of those other scanners).

Now, suppose that the manager component pushes to the first medical imaging scanner a first imaging protocol file. In various aspects, the manager component can determine whether or not the first imaging protocol file references as a dependency any other imaging protocol file, or whether or not the first imaging protocol file is referenced as a dependency by any other imaging protocol file. If either of those is true, the manager component can instruct the first medical imaging scanner to locally designate, mark, or flag the first imaging protocol file as a hybrid-modality protocol. On the other hand, if both of those are false, the manager component can instruct the first medical imaging scanner to locally designate, mark, or flag the first imaging protocol file as a single-modality protocol.

In this way, the manager component can be considered as automatically avoiding situations in which an imaging protocol file is assigned an erroneous local designation, which can cause downstream protocol inconsistencies (e.g., an actually-hybrid-modality protocol file that is mistakenly marked as single-modality can be inaccessible or unreadable to medical imaging scanners that depend upon it). In stark contrast, existing techniques do not automatically avoid such situations.

In various embodiments, the manager component can perform hybrid-aware protocol restore management for the first medical imaging scanner and for the second medical imaging scanner. In other words, the manager component can automatically ensure that restore operations are performed in an appropriate order or sequence among the first medical imaging scanner and the second medical imaging scanner, so as to avoid implementation of inconsistent imaging protocol files. In particular, the manager component can perform restore operations in the reverse order in which commit operations are performed as described herein. That is, rather than first restoring whichever medical imaging scanner whose imaging protocol files are depended upon (e.g., the dependee), the manager component can instead first restore whichever medical imaging scanner whose imaging protocol files do the depending (e.g., the depender).

In various aspects, when one or more previously-committed imaging protocol files (e.g., an imaging protocol transaction) are restored from a backup on a medical imaging scanner, it is possible that one or more currently-committed imaging protocol files that are not captured or reflected in that backup can be lost.

Now, suppose (without loss of generality) that the imaging protocol files committed on the first medical imaging scanner depend upon those committed on the second medical imaging scanner. Furthermore, suppose that it is desired to respectively restore or revert both the first medical imaging scanner and the second medical imaging scanner from their currently-committed consistent states back to some previously-committed consistent states. Note that a protocol inconsistency can arise if the second medical imaging scanner were restored or reverted but the first medical imaging scanner were not restored or reverted (e.g., in such case, one or more second imaging protocol files currently-committed on the second medical imaging scanner can be not reflected in the to-be-restored state of the second medical imaging scanner; so, those one or more second imaging protocol files can be lost upon restore of the second medical imaging scanner; if the first medical imaging scanner does not undergo a commensurate restore, then one or more first imaging protocol files currently-committed on the first medical imaging scanner can be maintained and can depend upon those one or more second imaging protocol files that were lost). To address this problem, the manager component can determine which medical imaging scanner serves as the primary scanner (e.g., the depender) and which medical imaging scanner serves as the secondary scanner (e.g., the dependee), and the manager component can accordingly ensure that the primary scanner is restored first. In this example, the manager component can determine that the first medical imaging scanner is the primary scanner (e.g., the scanner whose imaging protocol files do the depending). In response to such determination, the manager component can instruct the first medical imaging scanner to restore or revert to some prior state, and the manager component can refrain from instructing the second medical imaging scanner to restore or revert to that prior state. In particular, the manager component can wait to instruct the second medical imaging scanner to restore or revert to that prior state, until after receiving a notification from the first medical imaging scanner indicating successful restoration or reversion.

In this way, the manager component can be considered as automatically avoiding erroneous restore sequences or orderings that result in protocol inconsistencies on a hybrid-modality setup. In stark contrast, existing techniques do not automatically avoid such erroneous restore sequences or orderings.

In various embodiments, the manager component can perform hybrid-aware protocol editing management for the first medical imaging scanner and for the second medical imaging scanner. In other words, the manager component can automatically help to ensure that imaging protocol files implementable on the hybrid-modality setup formed by the first medical imaging scanner and the second medical imaging scanner are not rendered inconsistent by erroneous or mistaken edits.

In various aspects, a user or technician can interact with the graphical user interface of the manager component, so as to manually edit any given imaging protocol file that is stored in the imaging protocol library. In particular, the user or technician can make a selection on the graphical user interface so as to cause the manager component to launch an editor associated with that given imaging protocol file. Now, prior to launching the editor, the manager component can determine whether the given imaging protocol file depends upon, or is depended upon by, any other imaging protocol file stored in the imaging protocol library. If not, the manager component can launch the editor of that given imaging protocol file. If so, the manager component can launch the editor of that given imaging protocol file, and the manager component can also launch respective editors of whatever other imaging protocol files are determined to depend upon, or to be depended upon by, that given imaging protocol file. Such parallel launching of multiple editors can be considered as notifying the user or technician that whatever edits they desire to make to the given imaging protocol file should be commensurately made across all the launched editors.

The above paragraph can be considered as pertaining to embodiments in which editors are launched on a file-wise basis. However, this is a mere non-limiting example. In other embodiments, editors can instead be launched on a scanner-wise basis. Indeed, in various embodiments, a user or technician can make a selection on the graphical user interface of the manager component, so as to cause the manager component to launch an editor associated with any given medical imaging scanner that is registered with the management component (e.g., an editor that can edit any or all imaging protocol files that are stored in the imaging protocol library and that are executable or implementable by that given medical imaging scanner). Now, prior to launching the editor, the manager component can determine whether that given medical imaging scanner is designated as belonging to a hybrid-modality setup. If not, the manager component can launch the editor of that given medical imaging scanner. If so, the manager component can launch the editor of that given medical imaging scanner, and the manager component can also launch respective editors of whatever other medical imaging scanners are designated as forming a hybrid-modality setup with the given medical imaging scanner. Such parallel launching of multiple editors can be considered as notifying the user or technician that whatever edits they desire to make with respect to that given medical imaging scanner should be commensurately made across the entire hybrid-modality setup to which that given medical imaging scanner belongs.

In any of these ways, the manager component can be considered as automatically helping to avoid scenarios in which erroneous edits result in protocol inconsistencies on a hybrid-modality setup. In stark contrast, existing techniques do not automatically help to avoid such erroneous edits.

In various embodiments, the manager component can perform hybrid-aware scanner-protocol incompatibility management for the first medical imaging scanner and for the second medical imaging scanner. In other words, the manager component can automatically help to deal with situations in which an imaging protocol file that is attempted to be pushed to the first medical imaging scanner or to the second medical imaging scanner notwithstanding being incompatible with the first medical imaging scanner or with the second medical imaging scanner.

Indeed, suppose that it is desired to respectively push a first imaging protocol file and a second imaging protocol file to the first medical imaging scanner and to the second medical imaging scanner. As mentioned above, imaging-protocol files can be modality-specific, model-specific, or software-specific. So, suppose further that the first imaging protocol file is properly performable on the first medical imaging scanner (e.g., the first imaging protocol file can be compatible with the image-capture modality, with the model number, and with the software version of the first medical imaging scanner). However, suppose that the second imaging protocol file is not properly performable on the second medical imaging scanner (e.g., the second imaging protocol file can be incompatible with the image-capture modality, with the model number, or with the software version of the second medical imaging scanner). In such case, the manager component can prohibit or prevent the first imaging protocol file and the second imaging protocol file from being respectively pushed to the first medical imaging scanner and to the second medical imaging scanner. Instead, the manager component can identify, within the imaging protocol library, a third imaging protocol file that is marked as a clinical substitute for the second imaging protocol file but that is nevertheless properly performable on the second medical imaging scanner (e.g., that is nevertheless compatible with the image-capture modality, with the model number, and with the software version of the second medical imaging scanner). Accordingly, the manager component can respectively push the first imaging protocol file and the third imaging protocol file to the first medical imaging scanner and to the second medical imaging scanner.

In this way, the manager component can be considered as automatically helping to cure scenarios in which modality-incompatible, model-incompatible, or software-incompatible imaging protocol files are erroneously pushed to a hybrid-modality setup. In stark contrast, existing techniques do not automatically help to cure such incompatibilities.

Various embodiments described herein can be employed to use hardware or software to solve problems that are highly technical in nature (e.g., to facilitate automated imaging protocol management for hybrid modalities), that are not abstract and that cannot be performed as a set of mental acts by a human. Further, some of the processes performed can be performed by a specialized computer (e.g., graphical user interfaces, medical imaging scanners) for carrying out defined acts related to medical imaging scanners. For example, such defined acts can include: electronically accessing, by a device operatively coupled to a processor, a first medical imaging scanner and a second medical imaging scanner, wherein the first medical imaging scanner and the second medical imaging scanner can be of different image-capture modalities; and electronically performing, by the device, automated imaging protocol management across the first medical imaging scanner and the second medical imaging scanner.

As described herein, such defined tasks can further include: facilitating hybrid-aware scanner registration management (e.g., can involve asking a scanner to discover another scanner that is communicatively coupled to or physically near it); facilitating hybrid-aware protocol dependency management (e.g., can involve parsing imaging protocol files to identify what computing resources or data slots are referenced as dependencies, and evaluating whether or not those dependencies are broken or unbroken); facilitating hybrid-aware protocol commit management (e.g., can involve requesting commitment of imaging protocol files on dependee scanners before depender scanners); facilitating hybrid-aware remote protocol marking management (e.g., can involve checking whether scanners have correctly locally designated imaging protocol files as single-modality or hybrid-modality); facilitating hybrid-aware protocol restore management (e.g., can involve requesting restoration of imaging protocol files or transactions on depender scanners before dependee scanners); facilitating hybrid-aware protocol editing management (e.g., can involve launching in parallel editors for interdependent imaging protocol files); or facilitating hybrid-aware scanner-protocol incompatibility management (e.g., can involve substituting clinically-related imaging protocol files based on image-capture modality, based on model number, or based on software version).

Such defined acts are not performed manually by humans. Indeed, neither the human mind nor a human with pen and paper can electronically parse, electronically pull, electronically push, or electronically edit imaging protocol files to, from, or for medical imaging scanners (e.g., CT scanners, X-ray scanners, MRI scanners, NM scanners) and visually render appropriate notifications pertaining to such parsing, pulling, pushing, or editing on a graphical user interface. Indeed, medical imaging scanners, imaging protocol files, and graphical user interfaces are inherently-computerized, hardware-and-software-based constructs that simply cannot be meaningfully implemented in any way by the human mind without computers. A computerized tool that can electronically manage imaging protocol files pertaining to medical imaging scanners that collectively form a hybrid-modality setup is likewise inherently-computerized and cannot be implemented in any sensible, practical, or reasonable way without computers.

Moreover, various embodiments described herein can integrate into a practical application various teachings relating to automated imaging protocol management for hybrid modalities. As described above, existing techniques for facilitating automated imaging protocol management treat each medical imaging scanner in isolation (e.g., without regard to any other medical imaging scanners). Such isolation can, and often does, yield situations in which the medical imaging scanners belonging to a hybrid-modality setup implement inconsistent imaging protocol files. Such inconsistency prevents the hybrid-modality setup from properly performing scans on patients, and such inconsistency is often not discovered or caught until scan time, at which point remedying such inconsistency can be excessively inconvenient or time-consuming.

Various embodiments described herein can address one or more of these technical problems. In particular, various embodiments described herein can involve performing imaging protocol management that explicitly takes into account the interdependencies of hybrid-modality setups. By taking such interdependencies into account, various embodiments described herein can help to reduce, or even avoid altogether, situations in which inconsistent imaging protocol files are implemented on a hybrid-modality setup. Specifically, various embodiments described herein can facilitate: hybrid-aware scanner registration (e.g., so as to avoid failure to register all scanners of a hybrid-modality setup); hybrid-aware protocol dependency checking (e.g., so as to flag inconsistent protocol files that have been pulled from a hybrid-modality setup, or so as to avoid erroneously pushing inconsistent protocol files to the hybrid-modality setup); hybrid-aware commit synchronization (e.g., so as to avoid protocol inconsistencies that arise from erroneously-ordered commit operations); hybrid-aware remote protocol marking (e.g., so as to avoid protocol inconsistencies that arise from erroneous local protocol designations); hybrid-aware restore synchronization (e.g., so as to avoid protocol inconsistencies that arise from erroneously-ordered restore operations); hybrid-aware protocol editing synchronization (e.g., so as to avoid protocol inconsistencies that arise from erroneous protocol edits); or hybrid-aware scanner-protocol incompatibility curing (e.g., so as to deal with situations in which modality-incompatible, model-incompatible, or software-incompatible protocol files are attempted to be pushed to a hybrid-modality setup). Existing techniques do not perform such functionalities and thus are substantially increased risk of experiencing protocol inconsistencies or error in hybrid-modality setups. For at least these reasons, various embodiments described herein can be considered as an improved technique for facilitating automatic imaging protocol management for medical imaging scanners. Thus, various embodiments described herein certainly constitute a tangible and concrete technical improvement or technical advantage in the field of medical imaging scanners. Accordingly, such embodiments clearly qualify as useful and practical applications of computers.

Furthermore, various embodiments described herein can control real-world tangible devices based on the disclosed teachings. For example, various embodiments described herein can electronically control real-world graphical user interfaces and real-world medical imaging scanners (e.g., X-ray machines, CT machines, MRI machines).

It should be appreciated that the herein figures and description provide non-limiting examples of various embodiments and are not necessarily drawn to scale.

FIG. 1 illustrates a block diagram of an example, non-limiting system 100 that can facilitate automated imaging protocol management for hybrid modalities in accordance with one or more embodiments described herein. As shown, a hybrid-modality management system 102 can be electronically integrated, via any suitable wired or wireless electronic connections, with a medical imaging scanner 104 and with a medical imaging scanner 108.

In various embodiments, the medical imaging scanner 104 can be any suitable medical device or medical equipment that can electronically capture or electronically generate any suitable medical images of medical patients (e.g., humans, animals, or otherwise). In various aspects, the medical imaging scanner 104 can belong to a modality 106, where the modality 106 can be any suitable medical or clinical image-capture modality. As a non-limiting example, the modality 106 can be a CT image-capture modality, in which case the medical imaging scanner 104 can be a CT scanner that can capture or generate CT scanned pixel arrays or voxel arrays. As another non-limiting example, the modality 106 can be an MRI image-capture modality, in which case the medical imaging scanner 104 can be an MRI scanner that can capture or generate MRI scanned pixel arrays or voxel arrays. As even another non-limiting example, the modality 106 can be an X-ray image-capture modality, in which case the medical imaging scanner 104 can be an X-ray scanner that can capture or generate X-ray scanned pixel arrays or voxel arrays. As yet another non-limiting example, the modality 106 can be an ultrasound image-capture modality, in which case the medical imaging scanner 104 can be an ultrasound scanner that can capture or generate ultrasound scanned pixel arrays or voxel arrays. As still another non-limiting example, the modality 106 can be a PET image-capture modality, in which case the medical imaging scanner 104 can be a PET scanner that can capture or generate PET scanned pixel arrays or voxel arrays. As another non-limiting example, the modality 106 can be an NM image-capture modality, in which case the medical imaging scanner 104 can be an NM scanner that can capture or generate NM scanned pixel arrays or voxel arrays.

In various embodiments, the medical imaging scanner 108 can be any suitable medical device or medical equipment that can electronically capture or electronically generate any suitable medical images of medical patients. In various instances, the medical imaging scanner 108 can belong to a modality 110, where the modality 110 can be any suitable medical or clinical image-capture modality (e.g., CT image-capture modality, MRI image-capture modality, X-ray image-capture modality, ultrasound image-capture modality, PET image-capture modality, NM image-capture modality) that is different from or otherwise not the same as the modality 106. As a non-limiting example, if the modality 106 is a CT image-capture modality, then the modality 110 can be any of an MRI image-capture modality, an X-ray image-capture modality, an ultrasound image-capture modality, a PET image-capture modality, or an NM image-capture modality. As another non-limiting example, if the modality 106 is an MRI image-capture modality, then the modality 110 can be any of a CT image-capture modality, an X-ray image-capture modality, an ultrasound image-capture modality, a PET image-capture modality, or an NM image-capture modality.

In various embodiments, as shown by numeral 112, the medical imaging scanner 104 and the medical imaging scanner 108 can be considered as forming a hybrid-modality setup. In some cases, the medical imaging scanner 104 and the medical imaging scanner 108 can be electronically coupled together by any suitable wired or wireless electronic connection, such that the medical imaging scanner 104 and the medical imaging scanner 108 can electronically communicate with each other. In other cases, the medical imaging scanner 104 and the medical imaging scanner 108 can be physically located or physically deployed within any suitable threshold proximity of each other (e.g., can be physically deployed in the same hospital room as each other; can be physically deployed onboard the same emergency vehicle as each other). In any case, the medical imaging scanner 104 and the medical imaging scanner 108 can collectively form a hybrid-modality setup, such that the medical imaging scanner 104 and the medical imaging scanner 108 work in tandem to achieve a unified clinical objective or outcome for any given medical patient. As a non-limiting example, a medical patient can be scanned first by the medical imaging scanner 104, and the medical patient can then be scanned (e.g., mere seconds, minutes, or moments later) by the medical imaging scanner 108, and the medical images captured or generated by the medical imaging scanner 104 and the medical imaging scanner 108 can superimposed overtop of each other, can be rendered adjacent to each other, or can otherwise be interpreted or viewed together so as to obtain a diagnosis or prognosis for the medical patient. In such non-limiting example, the medical imaging scanner 104 can be considered as depending upon the medical imaging scanner 108 (e.g., the medical imaging scanner 104 cannot properly capture or generate a medical image of the medical patient if the medical imaging scanner 108 used unexpected or unfamiliar image-acquisition settings).

In various aspects, it can be desired to perform automated imaging protocol management for the medical imaging scanner 104 and for the medical imaging scanner 108. As described herein, the hybrid-modality management system 102 can facilitate such automated imaging protocol management.

In various embodiments, the hybrid-modality management system 102 can comprise a processor 114 (e.g., computer processing unit, microprocessor) and a non-transitory computer-readable memory 116 that is operably or operatively or communicatively connected or coupled to the processor 114. The non-transitory computer-readable memory 116 can store computer-executable instructions which, upon execution by the processor 114, can cause the processor 114 or other components of the hybrid-modality management system 102 (e.g., access component 118, manager component 120) to perform one or more acts. In various embodiments, the non-transitory computer-readable memory 116 can store computer-executable components (e.g., access component 118, manager component 120), and the processor 114 can execute the computer-executable components.

In various embodiments, the hybrid-modality management system 102 can comprise an access component 118. In various aspects, the access component 118 can electronically access the medical imaging scanner 104 or the medical imaging scanner 108. As a non-limiting example, the access component 118 can electronically communicate in any suitable fashion with the medical imaging scanner 104 or with the medical imaging scanner 108. That is, the access component 118 can electronically transmit any suitable electronic data to the medical imaging scanner 104 or to the medical imaging scanner 108, and the access component 118 can electronically receive any suitable electronic data from the medical imaging scanner 104 or from the medical imaging scanner 108. In any case, the access component 118 can electronically access the medical imaging scanner 104 or the medical imaging scanner 108, such that other components of the hybrid-modality management system 102 can electronically interact (e.g., by proxy) with the medical imaging scanner 104 or with the medical imaging scanner 108.

In various embodiments, the hybrid-modality management system 102 can comprise a manager component 120. In various aspects, the manager component 120 can facilitate automated imaging protocol management across, among, or otherwise for the medical imaging scanner 104 or the medical imaging scanner 108.

Although FIG. 1 shows the hybrid-modality management system 102 as managing only two medical imaging scanners (e.g., 104 and 108), this is a mere non-limiting example for case of explanation and illustration. In various cases, the hybrid-modality management system 102 can be electronically coupled to, and thus can facilitate automated imaging protocol management for, any suitable number of any suitable types of medical imaging scanners that are implemented or deployed in any suitable physical locations.

Furthermore, although not explicitly shown in FIG. 1, note that any other suitable accessory or ancillary devices can be implemented in conjunction with the medical imaging scanner 104 or with the medical imaging scanner 108. As a non-limiting example, any suitable image reconstruction consoles can be electronically coupled to the medical imaging scanner 104 or to the medical imaging scanner 108.

Figure 2:
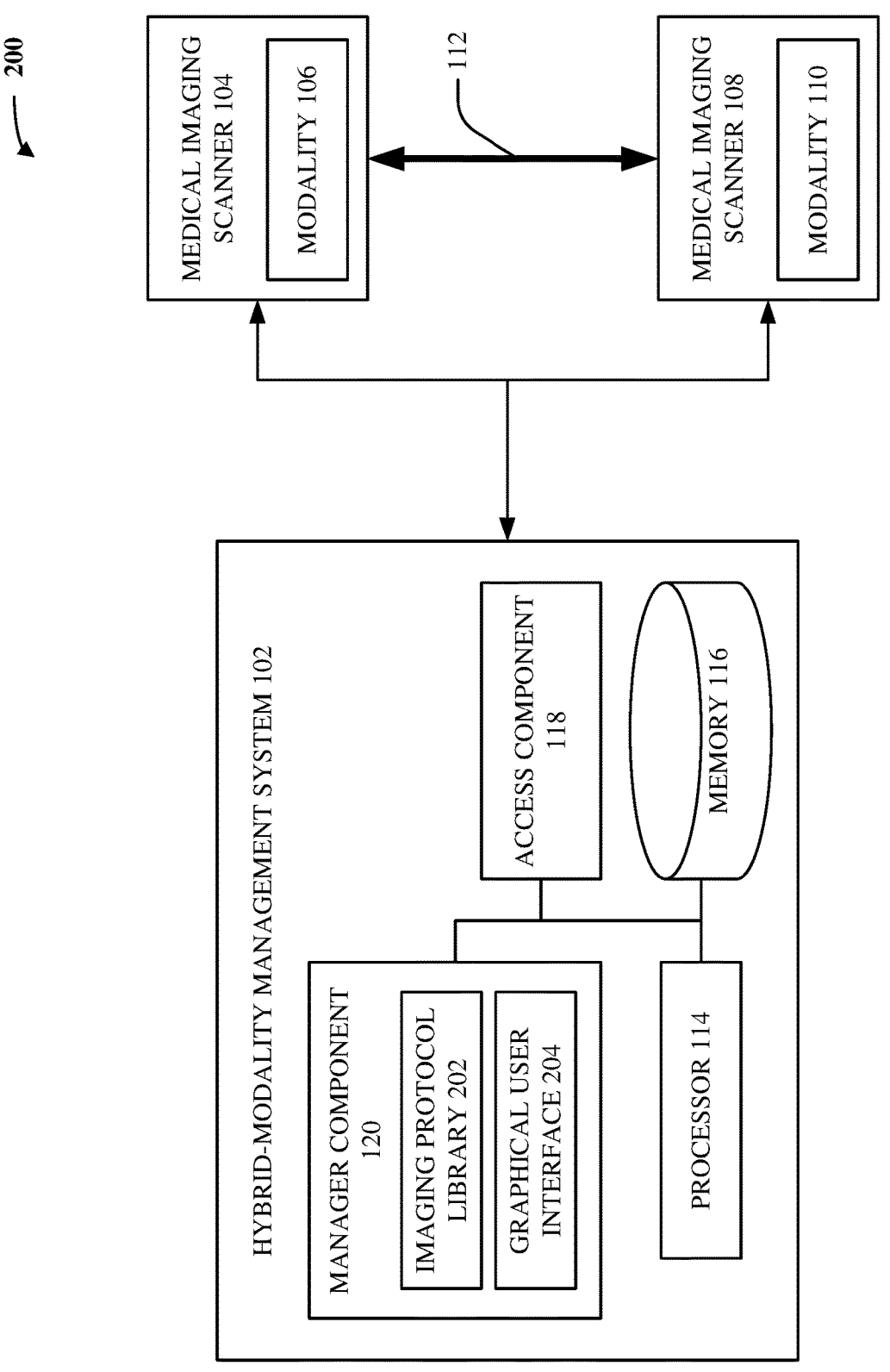
FIG. 2 illustrates a block diagram of an example, non-limiting system including an imaging protocol library and a graphical user interface that facilitates automated imaging protocol management for hybrid modalities in accordance with one or more embodiments described herein.

FIG. 2 illustrates a block diagram of an example, non-limiting system 200 including an imaging protocol library and a graphical user interface that can facilitate automated imaging protocol management for hybrid modalities in accordance with one or more embodiments described herein. As shown, the system 200 can, in some cases, comprise the same components as the system 100, and can further comprise an imaging protocol library 202 or a graphical user interface 204.

In various embodiments, the manager component 120 can electronically store, electronically maintain, electronically control, or otherwise electronically access the imaging protocol library 202. In various aspects, the imaging protocol library 202 can be any suitable database or data structure (e.g., graph data structure, relational data structure, hybrid data structure) which can store any suitable imaging protocol files pertaining to the medical imaging scanner 104, to the medical imaging scanner 108, or to any other suitable medical imaging scanners. Non-limiting aspects are described with respect to FIG. 3.

Figure 3:
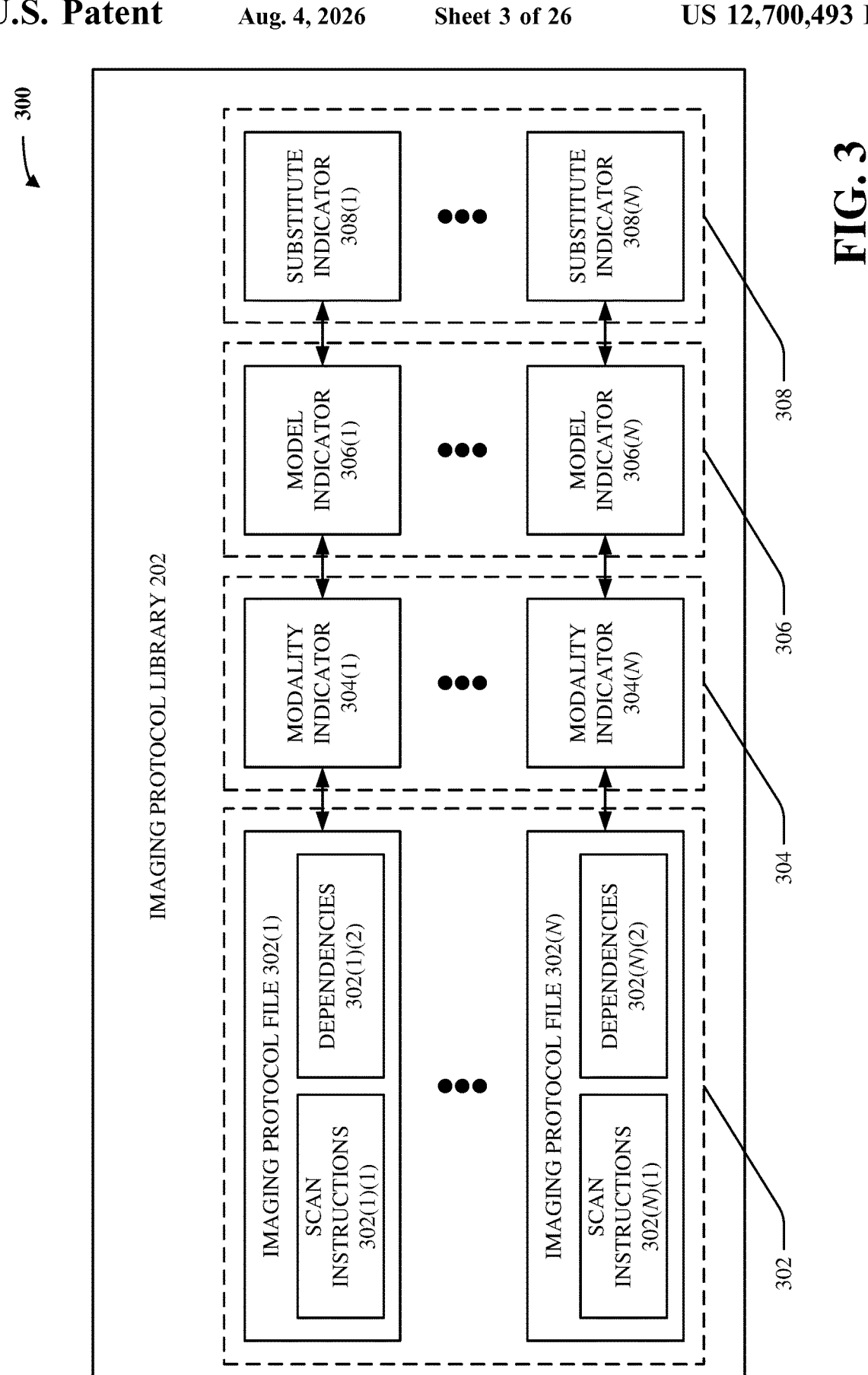
FIG. 3 illustrates an example, non-limiting block diagram showing an imaging protocol library in accordance with one or more embodiments described herein.

FIG. 3 illustrates an example, non-limiting block diagram 300 showing the imaging protocol library 202 in accordance with one or more embodiments described herein.

In various aspects, the imaging protocol library 202 can comprise a set of imaging protocol files 302. In various instances, the set of imaging protocol files 302 can comprise n files, for any suitable positive integer n: an imaging protocol file 302(1) to an imaging protocol file 302(n). In various cases, each of the set of imaging protocol files 302 can be any suitable electronic data (e.g., exhibited in any suitable format or syntax) that indicates, specifies, or otherwise conveys: instructions which, when followed or executed by a suitable or respective medical imaging scanner, can yield one or more medical images; and dependencies which are required or necessitated by those instructions.

For instance, the imaging protocol file 302(1) can comprise one or more scan instructions 302(1)(1) and one or more dependencies 302(1)(2). In various aspects, the one or more scan instructions 302(1)(1) can comprise any suitable number of scan instructions, where a scan instruction can be one or more scalars, one or more vectors, one or more matrices, one or more tensors, one or more character strings, or any suitable combination thereof that can indicate, convey, or otherwise represent an image-acquisition action or an image-acquisition parameter setting that can be executed, followed, or performed by a suitable or respective medical imaging scanner. As some non-limiting examples, a scan instruction can be: configuring a gantry of a medical imaging scanner to rotate at a specified angular velocity; configuring a gantry of a medical imaging scanner to sweep through a specified angular range; configuring a table of a medical imaging scanner to rise or fall to a specified height; or configuring a tube voltage or tube current of a medical imaging scanner to rise or fall to a specified value. In various instances, the one or more dependencies $302(1)(2)$ can comprise any suitable number of dependencies, where a dependency can be one or more scalars, one or more vectors, one or more matrices, one or more tensors, one or more character strings, or any suitable combination thereof that can indicate, convey, or otherwise represent a specified state, value, or content of a specified computing resource or data slot, where such specified state, value, or content is required or needed for the proper or correct performance of a respective scan instruction. As some non-limiting examples, a dependency can be: an energy session resource or slot of a particular medical imaging scanner having a particular state, value, or content; an administrator event resource or slot of a particular medical imaging scanner having a particular state, value, or content; or a post-processing resource or slot having a particular state, value, or content. Accordingly, the one or more dependencies $302(1)(2)$ can be considered as conditions that must be satisfied in order for the one or more scan instructions $302(1)(1)$ to be properly or correctly executed. Note that, in some cases, any of the one or more dependencies $302(1)(2)$ can be computing resources or data slots that are local or internal to whatever medical imaging scanner performs or executes the one or more scan instructions $302(1)(1)$. However, in other cases, any of the one or more dependencies $302(1)(2)$ can instead be computing resources or data slots that are remote from or external to whatever medical imaging scanner performs or executes the one or more scan instructions $302(1)(1)$.

As another instance, the imaging protocol file $302(n)$ can comprise one or more scan instructions $302(n)(1)$ and one or more dependencies $302(n)(2)$. In various aspects, the one or more scan instructions $302(n)(1)$ can comprise any suitable number of scan instructions. In various instances, the one or more dependencies $302(n)(2)$ can comprise any suitable number of dependencies. Just as above, the one or more dependencies $302(n)(2)$ can be considered as conditions that must be satisfied in order for the one or more scan instructions $302(n)(1)$ to be properly or correctly executed. Also as above, note that, in some cases, any of the one or more dependencies $302(n)(2)$ can be computing resources or data slots that are local or internal to whatever medical imaging scanner performs or executes the one or more scan instructions $302(1)(1)$. Moreover, in other cases, any of the one or more dependencies $302(n)(2)$ can instead be computing resources or data slots that are remote from or external to whatever medical imaging scanner performs or executes the one or more scan instructions $302(n)(1)$.

As mentioned above, note that an imaging protocol file can be a dependency for another imaging protocol file, as is often the case in hybrid-modality setups.

In various embodiments, the imaging protocol library 202 can comprise a set of modality indicators 304. In various aspects, the set of modality indicators 304 can respectively correspond (e.g., in one-to-one fashion) to the set of imaging protocol files 302. So, since the set of imaging protocol files 302 comprises n files, the set of modality indicators 304 can comprise n indicators: a modality indicator $304(1)$ to a modality indicator $304(n)$. In various instances, each of the set of modality indicators 304 can be any suitable electronic data that indicates, conveys, or otherwise represents which image-capture modality a respective one of the set of imaging protocol files 302 is designed or configured for. As a non-limiting example, the modality indicator $304(1)$ can correspond to the imaging protocol file $302(1)$. Thus, the modality indicator $304(1)$ can be one or more scalars, one or more vectors, one or more matrices, one or more tensors, one or more character strings, or any suitable combination thereof that can indicate or specify which image-capture modality (e.g., CT, MRI, X-ray, ultrasound, PET, NM) the imaging protocol file $302(1)$ is designed or configured for. In other words, the imaging protocol file $302(1)$ cannot be executed by a medical imaging scanner that does not belong to whichever image-capture modality is specified by the modality indicator $304(1)$. As another non-limiting example, the modality indicator $304(n)$ can correspond to the imaging protocol file $302(n)$. So, the modality indicator $304(n)$ can be one or more scalars, one or more vectors, one or more matrices, one or more tensors, one or more character strings, or any suitable combination thereof that can indicate or specify which image-capture modality (e.g., CT, MRI, X-ray, ultrasound, PET, NM) the imaging protocol file $302(n)$ is designed or configured for. In other words, the imaging protocol file $302(n)$ cannot be executed by a medical imaging scanner that does not belong to whichever image-capture modality is specified by the modality indicator $304(n)$.

In various embodiments, the imaging protocol library 202 can comprise a set of model indicators 306. In various aspects, the set of model indicators 306 can respectively correspond (e.g., in one-to-one fashion) to the set of imaging protocol files 302. So, since the set of imaging protocol files 302 comprises n files, the set of model indicators 306 can comprise n indicators: a model indicator $306(1)$ to a model indicator $306(n)$. In various instances, each of the set of model indicators 306 can be any suitable electronic data that indicates, conveys, or otherwise represents which scanner models a respective one of the set of imaging protocol files 302 is designed or configured for. As a non-limiting example, the model indicator $306(1)$ can correspond to the imaging protocol file $302(1)$. Thus, the model indicator $306(1)$ can be one or more scalars, one or more vectors, one or more matrices, one or more tensors, one or more character strings, or any suitable combination thereof that can indicate or specify which scanner model numbers (e.g., which scanner hardware versions, which scanner software versions) the imaging protocol file $302(1)$ is designed or configured for. In other words, the imaging protocol file $302(1)$ cannot be executed by a medical imaging scanner that does not belong to at least one of whichever scanner model numbers are specified by the model indicator $306(1)$. As another non-limiting example, the model indicator $306(n)$ can correspond to the imaging protocol file $302(n)$. So, the model indicator $306(n)$ can be one or more scalars, one or more vectors, one or more matrices, one or more tensors, one or more character strings, or any suitable combination thereof that can indicate or specify which scanner model numbers (e.g., which scanner hardware versions, which scanner software versions) the imaging protocol file $302(n)$ is designed or configured for. In other words, the imaging protocol file $302(n)$ cannot be executed by a medical imaging scanner that does not belong to at least one of whichever scanner model numbers are specified by the model indicator $306(n)$.

In various embodiments, the imaging protocol library 202 can comprise a set of substitute indicators 308. In various aspects, the set of substitute indicators 308 can respectively correspond (e.g., in one-to-one fashion) to the set of imaging protocol files 302. So, since the set of imaging protocol files 302 comprises n files, the set of substitute indicators 308 can comprise n indicators: a substitute indicator 308(1) to a substitute indicator 308(n). In various instances, each of the set of substitute indicators 308 can be any suitable electronic data that indicates, conveys, or otherwise represents one or more clinical substitutes for a respective one of the set of imaging protocol files 302. As a non-limiting example, the substitute indicator 308(1) can correspond to the imaging protocol file 302(1). Thus, the substitute indicator 308(1) can be one or more scalars, one or more vectors, one or more matrices, one or more tensors, one or more character strings, or any suitable combination thereof that can indicate or specify which (if any) others of the set of imaging protocol files 302 are clinical substitutes for the imaging protocol file 302(1) (e.g., which, if any, other imaging protocol files are designed to visualize the same anatomical structure for the same clinical purpose as the imaging protocol file 302(1), but for image-capture modalities that are not specified by the modality indicator 304(1), or for scanner model numbers that are not specified by the model indicator 306(1)). As another non-limiting example, the substitute indicator 308 (n) can correspond to the imaging protocol file 302(n). So, the substitute indicator 308(n) can be one or more scalars, one or more vectors, one or more matrices, one or more tensors, one or more character strings, or any suitable combination thereof that can indicate or specify which (if any) others of the set of imaging protocol files 302 are clinical substitutes for the imaging protocol file 302(n) (e.g., which, if any, other imaging protocol files are designed to visualize the same anatomical structure for the same clinical purpose as the imaging protocol file 302(n), but for image-capture modalities that are not specified by the modality indicator 304(n), or for scanner model numbers that are not specified by the model indicator 306(n)).

Referring back to FIG. 2, the graphical user interface 204 can be any suitable graphical user interface through which or via which a user or technician can view or interact with the imaging protocol library 202. As a non-limiting example, the graphical user interface 204 can be any suitable internet-accessible webpage which can show the contents of the imaging protocol library 202 and which can be visually rendered on any suitable electronic display (e.g., computer screen, computer monitor). In some instances, a user or technician can utilize the graphical user interface 204 to manually edit any of the imaging protocol files stored in the imaging protocol library 202. In other instances, a user or technician can utilize the graphical user interface 204 to manually select imaging protocol files to be pulled to the imaging protocol library 202 from the medical imaging scanner 104 or from the medical imaging scanner 108. In yet other instances, a user or technician can utilize the graphical user interface 204 to manually select imaging protocol files to be pushed from the imaging protocol library 202 to the medical imaging scanner 104 or to the medical imaging scanner 108.

Figure 4:
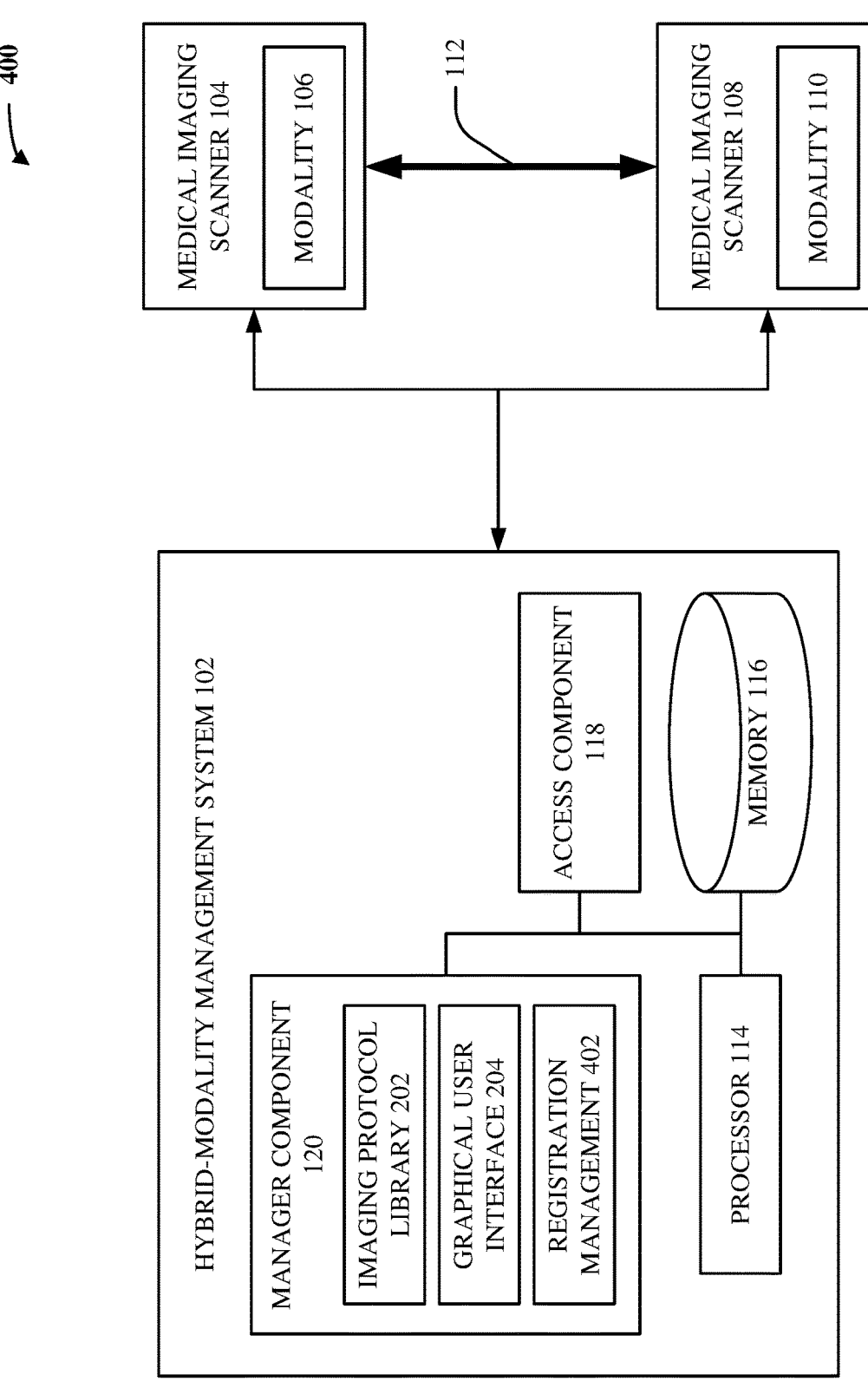
FIG. 4 illustrates a block diagram of an example, non-limiting system including registration management that facilitates automated imaging protocol management for hybrid modalities in accordance with one or more embodiments described herein.

FIG. 4 illustrates a block diagram of an example, non-limiting system 400 including registration management that can facilitate automated imaging protocol management for hybrid modalities in accordance with one or more embodiments described herein. As shown, the system 400 can, in some cases, comprise the same components as the system 200, and can further comprise registration management 402.

In various embodiments, the manager component 120 can electronically perform or electronically facilitate the registration management 402 for or with respect to the medical imaging scanner 104 or the medical imaging scanner 108. In various aspects, the registration management 402 can be considered as a procedure or technique for performing scanner registration in a hybrid-aware fashion. In various instances, scanner registration can be considered as the electronic receipt by the manager component 120 of any suitable properties, characteristics, attributes, or metadata pertaining to any suitable medical imaging scanner. In various cases, scanner registration can be considered as a preliminary step or action which can subsequently allow the manager component 120 to pull data from or to push data to any given medical imaging scanner.

In various aspects, the manager component 120 can perform scanner registration in a hybrid-aware fashion as follows. Whenever a new scanner is registered by a user or technician with the manager component 120, the manager component 120 can automatically instruct that newly-registered scanner to determine whether or not it is communicatively coupled to, or is physically close to, another scanner. If not, the manager component 120 can determine that that newly-registered scanner is not part of a hybrid-modality setup. On the other hand, if so, the manager component 120 can instead determine that that newly-registered scanner is part of a hybrid-modality setup. In such case, the manager component 120 can then prompt the user or technician to register whichever scanners are communicatively coupled to, or are physically close to, that newly-registered scanner. In this way, the manager component 120 can automatically ensure that no hybrid-modality setup is erroneously left partially registered.

As a non-limiting example, suppose that both the medical imaging scanner 104 and the medical imaging scanner 108 are initially not registered with the manager component 120. In such case, the manager component 120 can be unable to pull imaging protocol files from, or to push imaging protocol files to, the medical imaging scanner 104 and the medical imaging scanner 108. Now, suppose that the user or technician registers the medical imaging scanner 104 with the manager component 120. That is, suppose that the user or technician inputs to the manager component 120, via the graphical user interface 204, an identifier or name of the medical imaging scanner 104, the modality 106 of the medical imaging scanner 104, a model number (e.g., hardware version identifier or software version identifier) of the medical imaging scanner 104, or a physical location (e.g., hospital room number or address) of the medical imaging scanner 104. At such point, the manager component 120 can be able to pull imaging protocol files from, or to push imaging protocol files to, the medical imaging scanner 104. However, the manager component 120 can still be unable to pull imaging protocol files from, or to push imaging protocol files to, the medical imaging scanner 108. In various aspects, the manager component 120 can, automatically in response to registration of the medical imaging scanner 104, electronically instruct the medical imaging scanner 104 to search for any other medical imaging scanners that are communicatively coupled to the medical imaging scanner 104 (e.g., can be facilitated by any suitable device-discovery procedures) or that are within any suitable threshold spatial proximity of the medical imaging scanner 104 (e.g., can be facilitated by wireless fidelity or radio frequency identification location beacons). Because the medical imaging scanner 108 can be communicatively coupled to or physically near the medical imaging scanner 104, the medical imaging scanner 104 can respond affirmatively to the manager component 120, thereby notifying the manager component 120 of the existence of the medical imaging scanner 108. Accordingly, the manager component 120 can electronically designate or mark the medical imaging scanner 104 and the medical imaging scanner 108 as collectively forming a hybrid-modality setup. Furthermore, the manager component 120 can prompt or recommend registration of the medical imaging scanner 108. For instance, the manager component 120 can ask, via the graphical user interface 204, the user or technician for an identifier or name of the medical imaging scanner 108, for the modality 110 of the medical imaging scanner 108, or for a model number (e.g., hardware version identifier or software version identifier) of the medical imaging scanner 108. In this way, the manager component 120 can be considered as guarding or defending against a situation in which the user or technician mistakenly forgets to register the medical imaging scanner 108.

Figure 5:
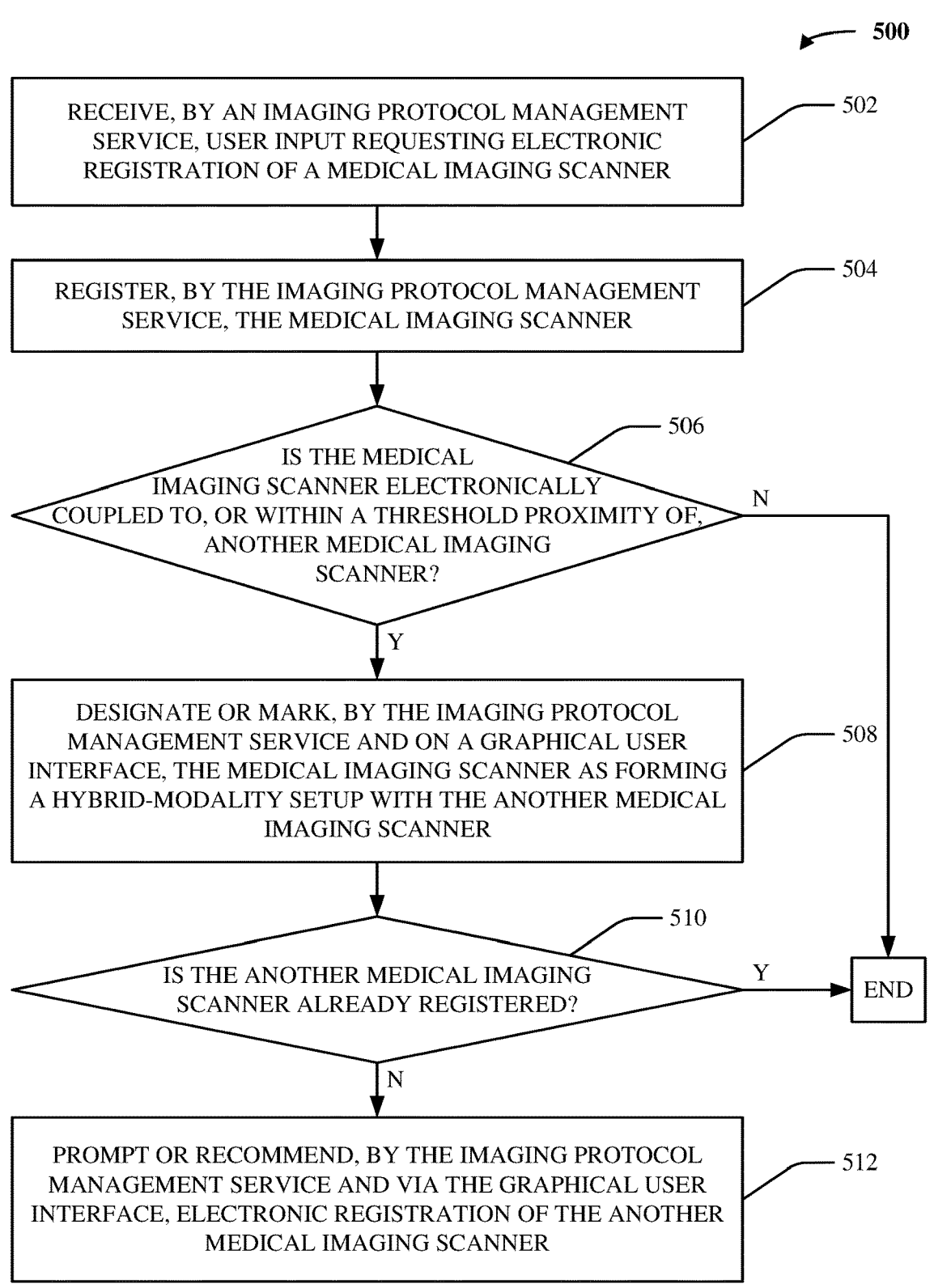
FIG. 5 illustrates a flow diagram of an example, non-limiting computer-implemented method that facilitates hybrid-aware scanner registration management in accordance with one or more embodiments described herein.

FIG. 5 illustrates a flow diagram of an example, non-limiting computer-implemented method 500 that can facilitate hybrid-aware scanner registration management in accordance with one or more embodiments described herein. In various cases, the hybrid-modality management system 102 can facilitate the computer-implemented method 500.

In various embodiments, act 502 can include receiving, by an imaging protocol management service (e.g., via 120 of 102), user input requesting electronic registration of a medical imaging scanner (e.g., 104).

In various aspects, act 504 can include registering, by the imaging protocol management service (e.g., via 120 of 102), the medical imaging scanner (e.g., can record user-provided identification data or metadata pertaining to the medical imaging scanner).

In various instances, act 506 can include determining, by the imaging protocol management service (e.g., via 120 of 102), whether the medical imaging scanner is electronically coupled to, or is within a threshold proximity of, another medical imaging scanner (e.g., 108). If not (e.g., if the medical imaging scanner is not communicatively coupled to, and is not within the threshold proximity of, any other medical imaging scanner), the computer-implemented method 500 can end. If so (e.g., if the medical imaging scanner is communicatively coupled to, or is within the threshold proximity of, another medical imaging scanner), the computer-implemented method 500 can proceed to act 508.

In various cases, act 508 can include designating or marking, by the imaging protocol management service (e.g., via 120 of 102) and on a graphical user interface (e.g., 204), the medical imaging scanner as forming a hybrid-modality setup with the another medical imaging scanner.

In various aspects, act 510 can include determining, by the imaging protocol management service (e.g., via 120 of 102), whether the another medical imaging scanner is already registered. If so (e.g., if the another medical imaging scanner is already registered), the computer-implemented method 500 can end. If not (e.g., if the another medical imaging scanner is not yet registered), the computer-implemented method 500 can proceed to act 512.

In various instances, act 512 can include prompting or recommending, by the imaging protocol management service (e.g., via 120 of 102) and via the graphical user interface, electronic registration of the another medical imaging scanner.

Figure 6:
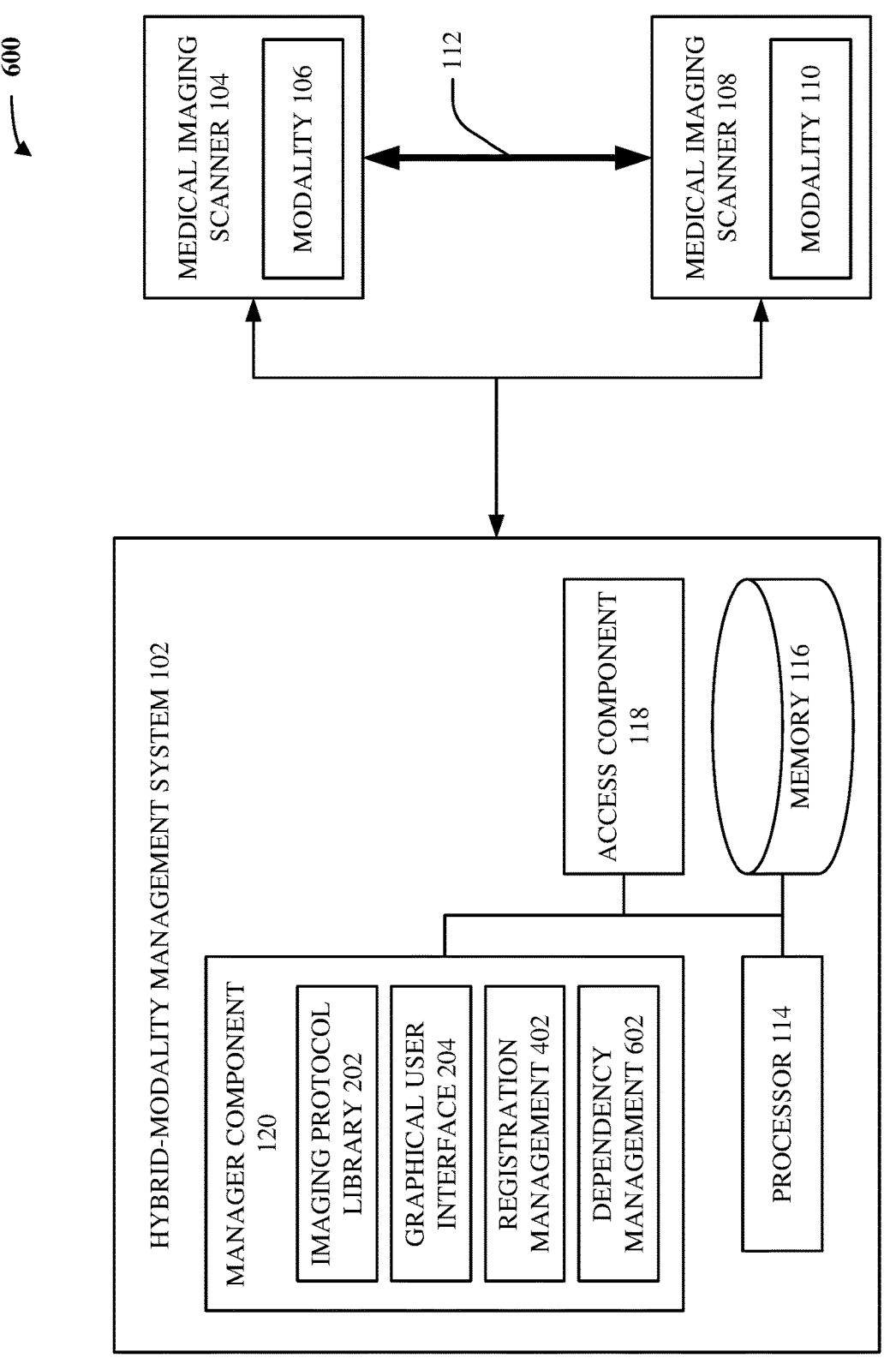
FIG. 6 illustrates a block diagram of an example, non-limiting system including dependency management that facilitates automated imaging protocol management for hybrid modalities in accordance with one or more embodiments described herein.

FIG. 6 illustrates a block diagram of an example, non-limiting system 600 including hybrid-aware protocol dependency management that can facilitate automated imaging protocol management for hybrid modalities in accordance with one or more embodiments described herein. As shown, the system 600 can, in some cases, comprise the same components as the system 400, and can further comprise dependency management 602.

In various embodiments, the manager component 120 can electronically perform or electronically facilitate the dependency management 602 for or with respect to the medical imaging scanner 104 or the medical imaging scanner 108. In various aspects, the dependency management 602 can be considered as a procedure or technique for checking, validating, or verifying interdependencies between pulled or pushed imaging protocol files in a hybrid-aware fashion.

In various aspects, the manager component 120 can perform such interdependency checking, validating, or verifying in a hybrid-aware fashion as follows. Whenever imaging protocol files are pulled from a hybrid-modality setup, or whenever it is desired to push imaging protocol files to the hybrid-modality setup, the manager component 120 can electronically parse those imaging protocol files, so as to discover or identify the dependencies specified in those imaging protocol files. In various instances, the manager component 120 can also query the hybrid-modality setup, so as to discover or identify all computing resources or data slots that are accessible, available, or readable to the hybrid-modality setup, and so as to discover or identify the actual states, values, or contents of those computing resources or data slots. The manager component 120 can then evaluate whether or not each dependency specified in the imaging protocol files is valid, based on those discovered computing resources or data slots. For instance, suppose that a given dependency specifies a particular state, value, or content of a particular computing resource or data slot; suppose further that that particular computing resource or data slot is accessible, available, or readable to the appropriate scanner in the hybrid-modality setup; and suppose yet further that the actual state, value, or content of that particular computing resource or data slot does not match the particular state, value, or content. In such case, the manager component 120 can conclude that the given dependency is invalid. As another instance, suppose that a given dependency specifies a particular state, value, or content of a particular computing resource or data slot; suppose further that that particular computing resource or data slot is accessible, available, or readable to the appropriate scanner in the hybrid-modality setup; and suppose yet further that the actual state, value, or content of that particular computing resource or data slot does match the particular state, value, or content. In such case, the manager component 120 can instead conclude that the given dependency is valid. As still another instance, suppose that a given dependency specifies a particular state, value, or content of a particular computing resource or data slot; and suppose further that that particular computing resource or data slot is not accessible, available, or readable to the appropriate scanner in the hybrid-modality setup. In such case, the manager component 120 can conclude that the given dependency is invalid, regardless of the actual state, value, or content of that particular computing resource or data slot.

In some aspects, if the imaging protocol files have been pulled from the hybrid-modality setup and an invalid dependency is detected, the manager component 120 can generate any suitable warning or alert on the graphical user interface 204. In other aspects, if the imaging protocol files are about to be pushed to the hybrid-modality setup and an invalid dependency is detected, the manager component 120 can prohibit or prevent such push and can accordingly generate any suitable warning or alert on the graphical user interface 204.

Figure 7:
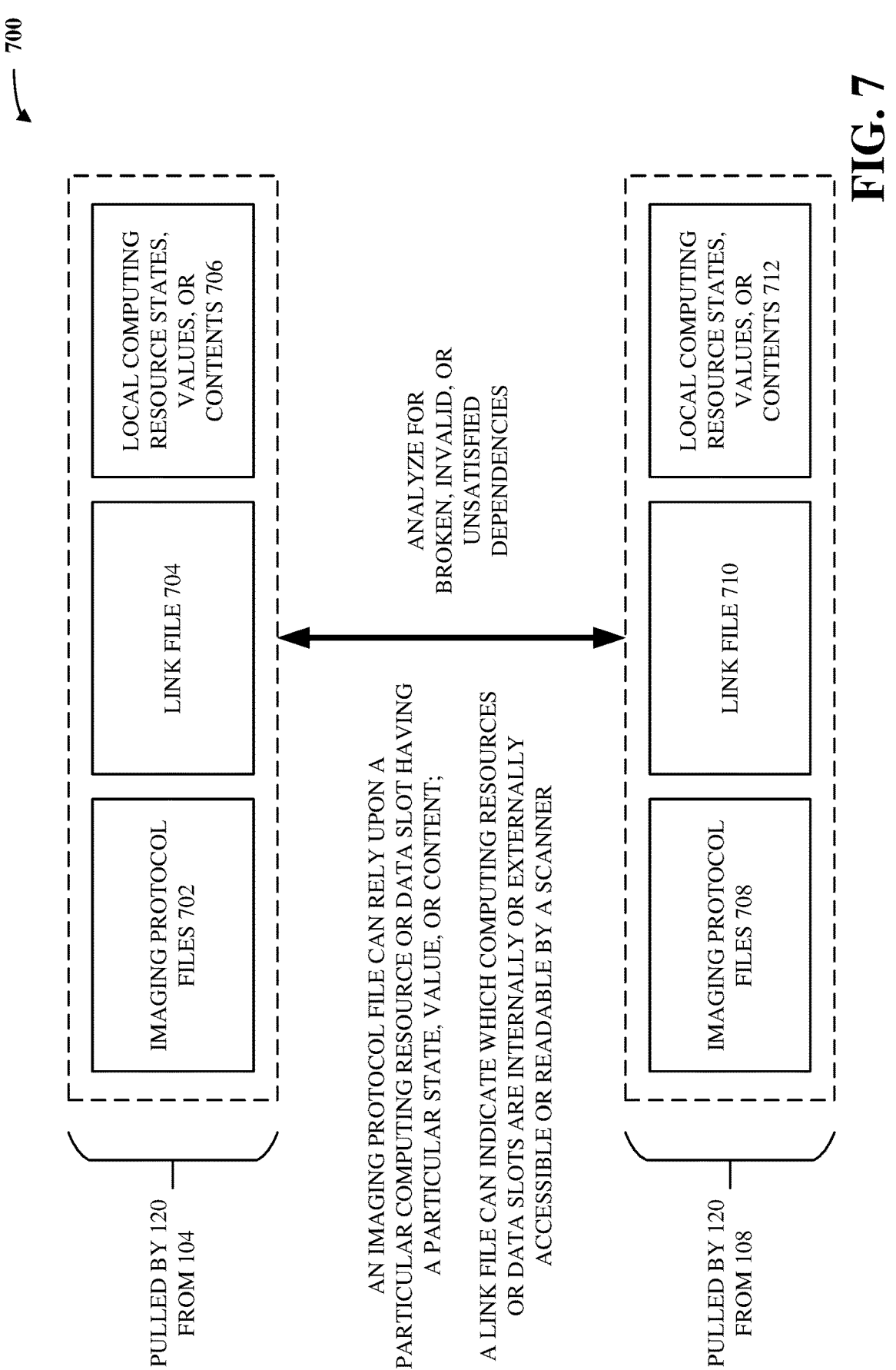
FIG. 7 illustrates an example, non-limiting block diagram showing hybrid-aware protocol dependency management in accordance with one or more embodiments described herein.

Non-limiting aspects specifically with respect to the medical imaging scanner 104 and the medical imaging scanner 108 are described with respect to FIG. 7.

FIG. 7 illustrates an example, non-limiting block diagram 700 showing hybrid-aware protocol dependency management in accordance with one or more embodiments described herein.

In various aspects, the manager component 120 can pull from the medical imaging scanner 104 one or more imaging protocol files 702, a link file 704, or one or more local computing resource states, values, or contents 706. In various instances, the one or more imaging protocol files 702 can be any suitable imaging protocol files, as described above, that can have been committed to or implemented on the medical imaging scanner 104. In various cases, the link file 704 can be any suitable electronic data (e.g., one or more scalars, one or more vectors, one or more matrices, one or more tensors, one or more character strings, or any suitable combination thereof) that can specify, indicate, convey, or otherwise point to which specific computing resources or data slots that are internally or externally accessible or readable by the medical imaging scanner 104. In other words, the link file 704 can be considered as indicating which specific computing resources or data slots (e.g., which can be local to the medical imaging scanner 104 or remote from the medical imaging scanner 104) that the medical imaging scanner 104 has permission or authority to read or access. In various aspects, the one or more local computing resource states, values, or contents 706 can be any suitable electronic data (e.g., one or more scalars, one or more vectors, one or more matrices, one or more tensors, one or more character strings, or any suitable combination thereof) indicating or conveying the specific states, values, or contents of whatever computing resources or data slots that are locally or internally maintained by or on the medical imaging scanner 104.

Likewise, in various aspects, the manager component 120 can pull from the medical imaging scanner 108 one or more imaging protocol files 708, a link file 710, or one or more local computing resource states, values, or contents 712. In various instances, the one or more imaging protocol files 708 can be any suitable imaging protocol files, as described above, that can have been committed to or implemented on the medical imaging scanner 108. In various cases, the link file 710 can be any suitable electronic data (e.g., one or more scalars, one or more vectors, one or more matrices, one or more tensors, one or more character strings, or any suitable combination thereof) that can specify, indicate, convey, or otherwise point to which specific computing resources or data slots that are internally or externally accessible or readable by the medical imaging scanner 108. That is, the link file 710 can be considered as indicating which specific computing resources or data slots (e.g., which can be local to the medical imaging scanner 108 or remote from the medical imaging scanner 108) that the medical imaging scanner 108 has permission or authority to read or access. In various aspects, the one or more local computing resource states, values, or contents 712 can be any suitable electronic data (e.g., one or more scalars, one or more vectors, one or more matrices, one or more tensors, one or more character strings, or any suitable combination thereof) indicating or conveying the specific states, values, or contents of whatever computing resources or data slots that are locally or internally maintained by or on the medical imaging scanner 108.

In various aspects, the manager component 120 can analyze all of this pulled data together or collectively, so as to determine whether or not the hybrid-modality setup formed by the medical imaging scanner 104 and the medical imaging scanner 108 is implementing inconsistent imaging protocol files.

As a non-limiting example, first consider the data pulled from the medical imaging scanner 104.

Suppose that a given dependency that is specified or referenced in at least one of the one or more imaging protocol files 702 is also specified or referenced in the link file 704. This can be interpreted to mean that whatever computing resource or data slot that is the subject of that given dependency is properly accessible or readable to the medical imaging scanner 104. In such case, the manager component 120 can determine whether or not that given dependency is satisfied by the one or more local computing resource states, values, or contents 706, by the one or more imaging protocol files 708 (e.g., recall that an imaging protocol file can itself be a dependency for another imaging protocol file), or by the one or more local computing resource states, values, or contents 712. That is, the manager component 120 can determine whether or not the computing resource or data slot specified by that given dependency actually has the state, value, or content that the given dependency indicates that it should have. If so, the manager component 120 can conclude that the given dependency is valid, satisfied, or otherwise unbroken. If not, the manager component 120 can instead conclude that the given dependency is invalid, unsatisfied, or otherwise broken. In particular, the manager component 120 can conclude in such case that the given dependency is accessible to the medical imaging scanner 104 but does not have the proper or correct state, value, or content.

Suppose instead that a given dependency that is specified or referenced in at least one of the one or more imaging protocol files 702 is not specified or referenced in the link file 704. This can be interpreted to mean that whatever computing resource or data slot that is the subject of that given dependency is not properly accessible or readable to the medical imaging scanner 104. In such case, the manager component 120 can conclude that the given dependency is invalid, unsatisfied, or otherwise broken, regardless of the actual state, value, or content of that given dependency.

Suppose instead that a given dependency that is specified or referenced in the link file 704 is not specified or referenced in any of the one or more imaging protocol files 702. This can be interpreted to mean that whatever computing resource or data slot that is the subject of that given dependency is properly accessible or readable to the medical imaging scanner 104 but is not required or relied upon by any of the one or more imaging protocol files 702. In such case, the manager component 120 can conclude that the given dependency is valid, satisfied, or otherwise unbroken, regardless of the actual state, value, or content of that given dependency. In other words, the manager component 120 can conclude that the given dependency is unlinked or not used. However, note that it is possible for such dependency to be used or linked at a later time (e.g., can be used or linked at scan time).

As another non-limiting example, consider the data pulled from the medical imaging scanner 108.

Suppose that a given dependency that is specified or referenced in at least one of the one or more imaging protocol files 708 is also specified or referenced in the link file 710. This can be interpreted to mean that whatever computing resource or data slot that is the subject of that given dependency is properly accessible or readable to the medical imaging scanner 108. In such case, the manager component 120 can determine whether or not that given dependency is satisfied by the one or more local computing resource states, values, or contents 712, by the one or more imaging protocol files 702, or by the one or more local computing resource states, values, or contents 706. That is, the manager component 120 can determine whether or not the computing resource or data slot specified by that given dependency actually has the state, value, or content that the given dependency indicates that it should have. If so, the manager component 120 can conclude that the given dependency is valid, satisfied, or otherwise unbroken. If not, the manager component 120 can instead conclude that the given dependency is invalid, unsatisfied, or otherwise broken. In particular, the manager component 120 can conclude in such case that the given dependency is accessible to the medical imaging scanner 108 but does not have the proper or correct state, value, or content.

Suppose instead that a given dependency that is specified or referenced in at least one of the one or more imaging protocol files 708 is not specified or referenced in the link file 710. This can be interpreted to mean that whatever computing resource or data slot that is the subject of that given dependency is not properly accessible or readable to the medical imaging scanner 108. In such case, the manager component 120 can conclude that the given dependency is invalid, unsatisfied, or otherwise broken, regardless of the actual state, value, or content of that given dependency.

Suppose instead that a given dependency that is specified or referenced in the link file 710 is not specified or referenced in any of the one or more imaging protocol files 708. This can be interpreted to mean that whatever computing resource or data slot that is the subject of that given dependency is properly accessible or readable to the medical imaging scanner 108 but is not required or relied upon by any of the one or more imaging protocol files 708. In such case, the manager component 120 can conclude that the given dependency is valid, satisfied, or otherwise unbroken, regardless of the actual state, value, or content of that given dependency. In other words, the manager component 120 can conclude that the given dependency is unlinked or not used. However, note that it is possible for such dependency to be used or linked at a later time.

In this way, the manager component 120 can automatically detect protocol inconsistencies among the medical imaging scanner 104 and the medical imaging scanner 108.

Furthermore, in various aspects, note that dependencies can be nested or daisy-chained together. That is, a dependency (e.g., referred to as a parent) can be any suitable computing resource or data slot whose state, value, or content can reference or depend upon another dependency (e.g., referred to as a child). In various aspects, when evaluating or checking any given dependency, the manager component 120 can also evaluate or check any child (e.g., or grandchild, or great-grandchild) dependencies of that given dependency. If any child dependency of that given dependency is invalid, broken, or unsatisfied, then the manager component 120 can conclude that the given dependency itself is invalid, broken, or unsatisfied.

FIGS. 8-11 illustrate flow diagrams of example, nonlimiting computer-implemented methods 800, 900, 1000, and 1100 that can facilitate hybrid-aware protocol dependency management in accordance with one or more embodiments described herein. In various cases, the hybrid-modality management system 102 can facilitate the computer-implemented methods 800, 900, 1000, and 1100.

Figure 8:
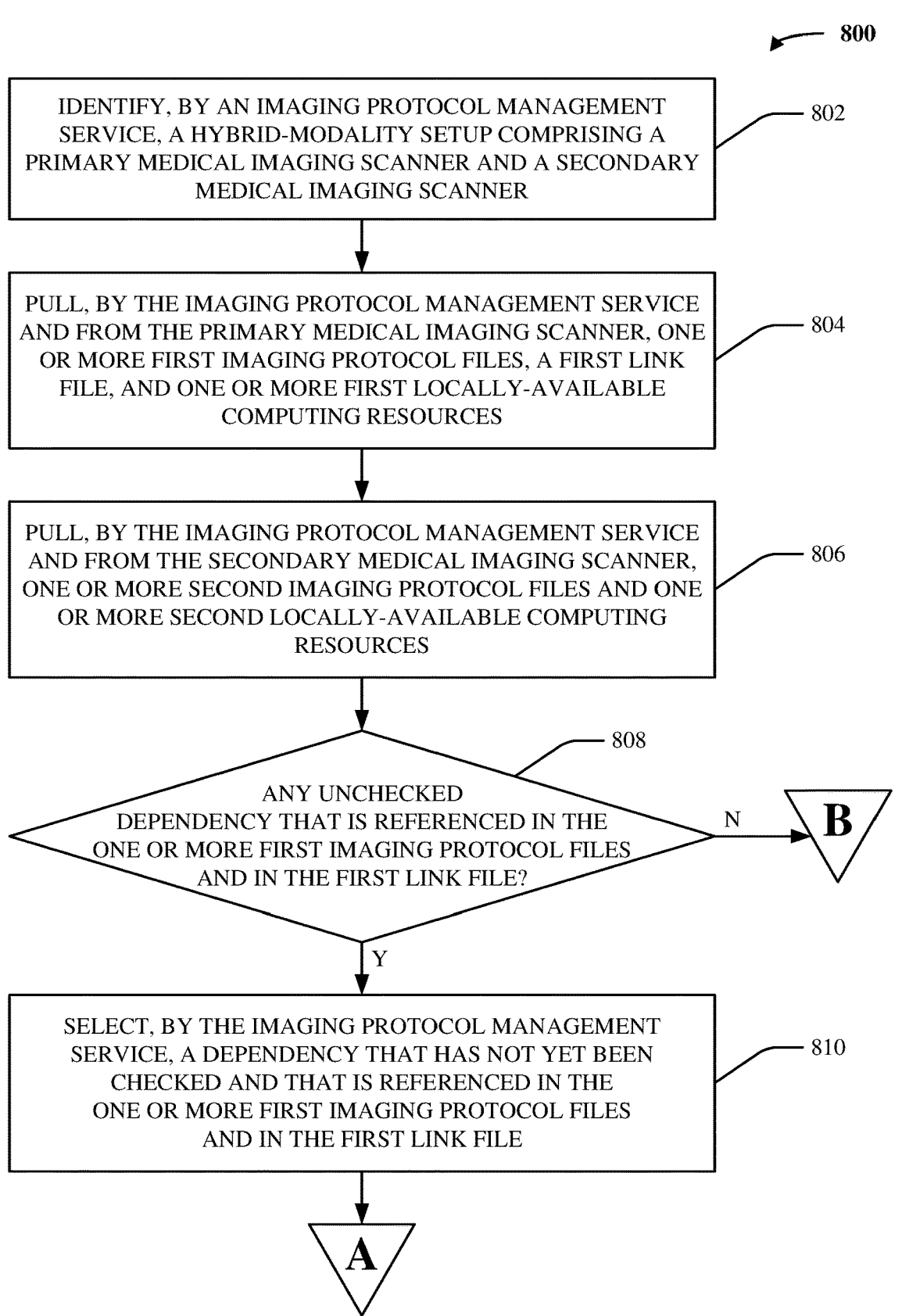
FIGS. 8-11 illustrate flow diagrams of example, non-limiting computer-implemented methods that facilitate hybrid-aware protocol dependency management in accordance with one or more embodiments described herein.

First, consider FIG. 8. In various embodiments, act 802 can include identifying, by an imaging protocol management service (e.g., via 120 of 102), a hybrid-modality setup comprising a primary medical imaging scanner (e.g., 104) and a secondary medical imaging scanner (e.g., 108). Note that, as used herein, the terms "primary" and "secondary" can be interpreted to mean the following: the imaging protocol files of the primary medical imaging scanner can depend upon those of the secondary medical imaging scanner, but the imaging protocol files of the secondary medical imaging scanner can be not dependent upon those of the primary medical imaging scanner.

In various aspects, act 804 can include pulling, by the imaging protocol management service (e.g., via 120 of 102) and from the primary medical imaging scanner, one or more first imaging protocol files (e.g., 702), a first link file (e.g., 704), and one or more first locally-available computing resources (e.g., 706).

In various instances, act 806 can include pulling, by the imaging protocol management service (e.g., via 120 of 102) and from the secondary medical imaging scanner, one or more second imaging protocol files (e.g., 708) and one or more second locally-available computing resources (e.g., 712).

In various cases, act 808 can include determining, by the imaging protocol management service (e.g., via 120 of 102), whether there is any unchecked dependency that is referenced in the one or more first imaging protocol files and that is referenced in the first link file. If so (e.g., if there is at least one dependency that has not yet been checked, that is referenced or recited in any of the one or more first imaging protocol files, and that is also referenced or recited in the first link file), the computer-implemented method 800 can proceed to act 810. If not (e.g., if there is no dependency that has not yet been checked, that is referenced or recited in any of the one or more first imaging protocol files, and that is also referenced or recited in the first link file), the computer-implemented method 800 can instead proceed to act 1002 of the computer-implemented method 1000.

In various aspects, act 810 can include selecting, by the imaging protocol management service (e.g., via 120 of 102), a dependency that has not yet been checked, that is referenced in the one or more imaging protocol files, and that is referenced in the first link file. In various cases, the computer-implemented method 800 can then proceed to act 902 of the computer-implemented method 900.

Figure 9:
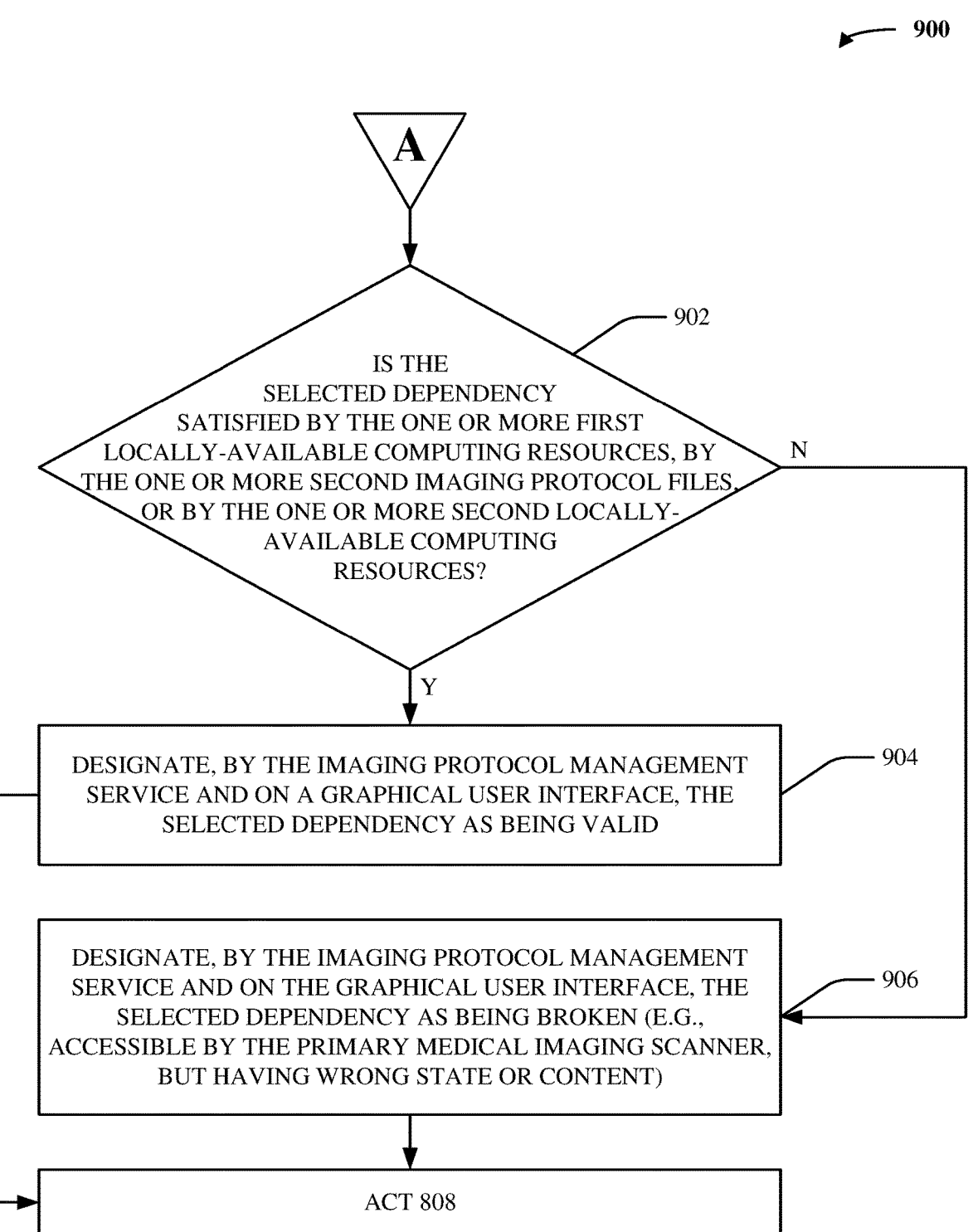

Now, consider FIG. 9. In various embodiments, act 902 can include determining, by the imaging protocol management service (e.g., via 120 of 102), whether the selected dependency is satisfied by the one or more first locally-available computing resources, by the one or more second imaging protocol files, or by the one or more second locally-available computing resources. If so (e.g., if the selected dependency actually has the state, value, or content that the one or more first imaging protocol files specify that it is supposed to have), the computer-implemented method 900 can proceed to act 904. If not (e.g., if the selected dependency does not actually have the state, value, or content that the one or more first imaging protocol files specify that it is supposed to have), the computer-implemented method 900 can instead proceed to act 906.

In various aspects, act 904 can include designating, by the imaging protocol management service (e.g., via 120 of 102) and on a graphical user interface (e.g., 204), the selected dependency as being valid. The computer-implemented method 900 can then proceed back to act 808 of the computer-implemented method 800.

In various instances, act 906 can include designating, by the imaging protocol management service (e.g., via 120 of 102) and on the graphical user interface, the selected dependency as being broken. In such case, the selected dependency can be considered as being accessible or readable by the primary medical imaging scanner, but the selected dependency can have the wrong or incorrect state, value, or content. In various aspects, the computer-implemented method 900 can then proceed back to act 808 of the computer-implemented method 800.

Figure 10:
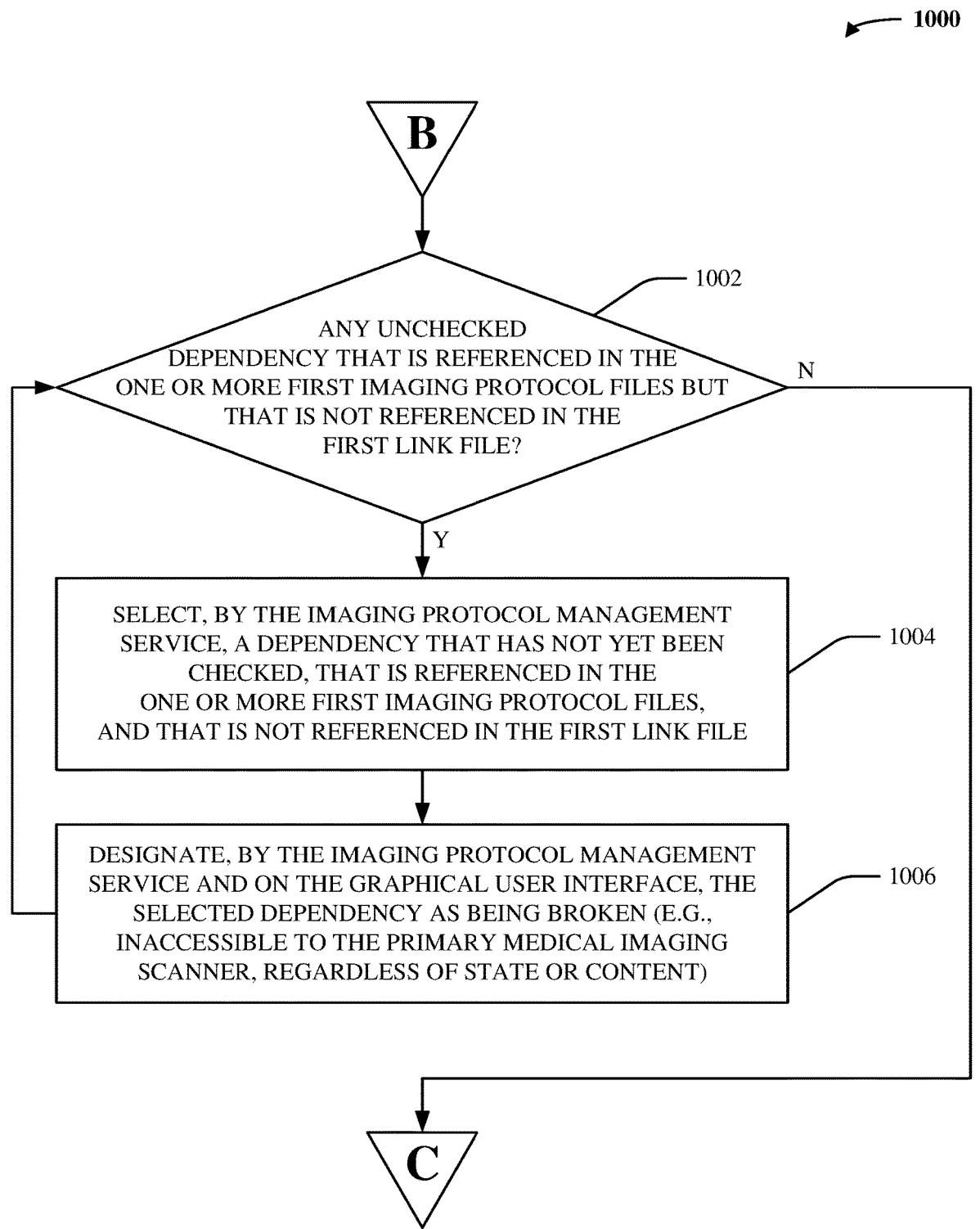

Now, consider FIG. 10. In various embodiments, act 1002 can include determining, by the imaging protocol management service (e.g., via 120 of 102), whether there is any unchecked dependency that is referenced in the one or more first imaging protocol files but that is not referenced in the first link file. If so (e.g., if there is at least one dependency that has not yet been checked, that is referenced or recited in any of the one or more first imaging protocol files, and that is not referenced or recited in the first link file), the computer-implemented method 1000 can proceed to act 1004. If not (e.g., if there is no dependency that has not yet been checked, that is referenced or recited in any of the one or more first imaging protocol files, and that is not referenced or recited in the first link file), the computer-implemented method 1000 can instead proceed to act 1102 of the computer-implemented method 1100.

In various aspects, act 1004 can include selecting, by the imaging protocol management service (e.g., via 120 of 102), a dependency that has not yet been checked, that is referenced in the one or more first imaging protocol files, and that is not referenced in the first link file.

In various instances, act 1006 can include designating, by the imaging protocol management service (e.g., via 120 of 102) and on the graphical user interface, the selected dependency as being broken. In such case, the selected dependency can be considered as not being accessible or readable to the primary medical imaging scanner, meaning that there can be no need to check the state, value, or content of the selected dependency. In various aspects, the computer-implemented method 1000 can then proceed back to act 1002.

Although not explicitly shown in FIG. 10, note that, whenever a given dependency is designated as broken, the imaging protocol file that recites that given dependency can likewise be designated or marked as broken. Such designation or marking can be visually rendered (e.g., on 204).

Figure 11:
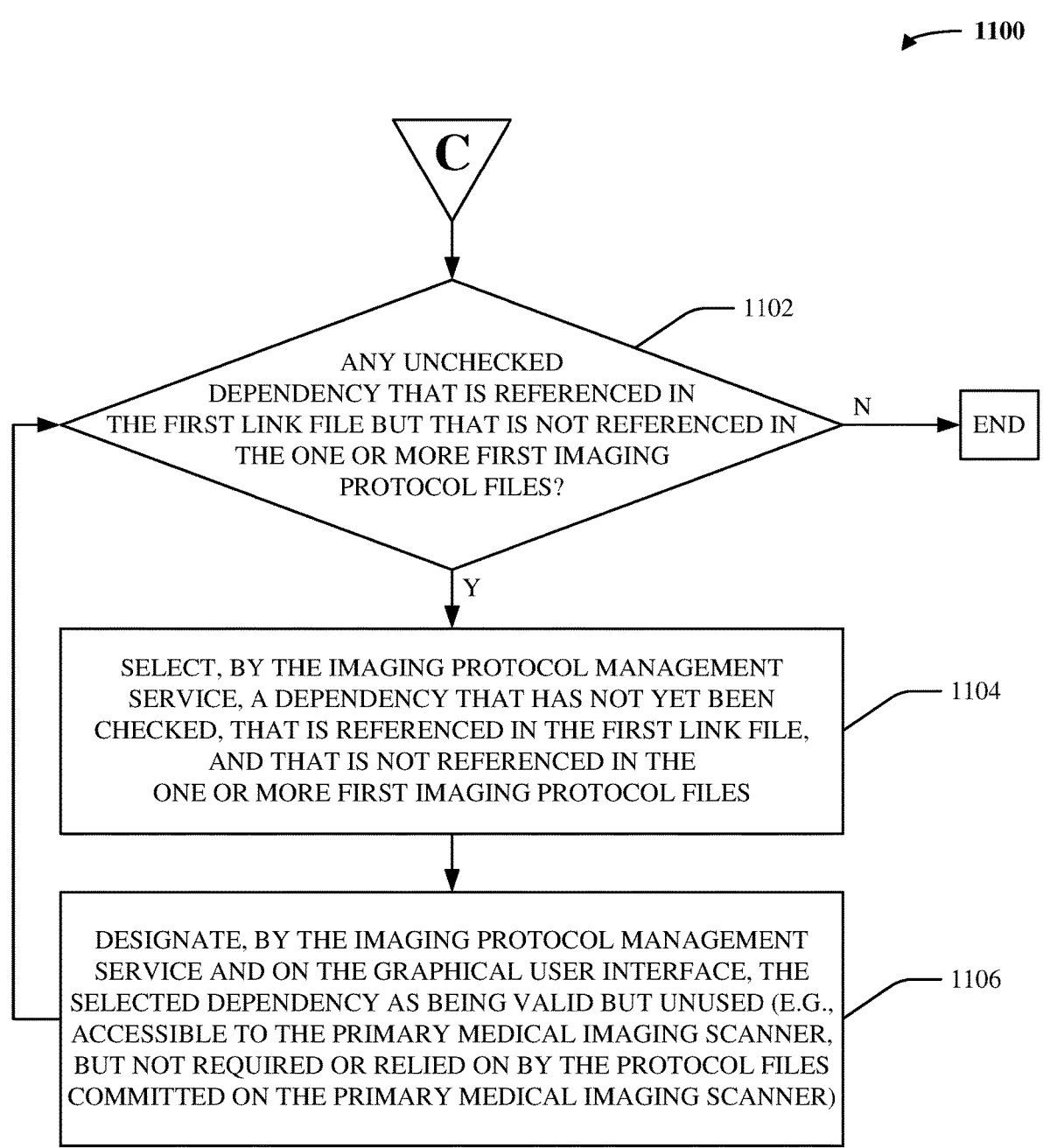

Now, consider FIG. 11. In various embodiments, act 1102 can include determining, by the imaging protocol management service (e.g., via 120 of 102), whether there is any unchecked dependency that is referenced in the first link file but that is not referenced in the one or more first imaging protocol files. If so (e.g., if there is at least one dependency that has not yet been checked, that is referenced or recited in the first link file, and that is not referenced or recited in any of the one or more first imaging protocol files), the computer-implemented method 1100 can proceed to act 1104. If not (e.g., if there is no dependency that has not yet been checked, that is referenced or recited in the first link file, and that is not referenced or recited in any of the one or more first imaging protocol files), the computer-implemented method 1100 can end.

In various aspects, act 1104 can include selecting, by the imaging protocol management service (e.g., via 120 of 102), a dependency that has not yet been checked, that is referenced in the first link file, and that is not referenced in the one or more first imaging protocol files.

In various instances, act 1106 can include designating, by the imaging protocol management service (e.g., via 120 of 102) and on the graphical user interface, the selected dependency as being valid but unused. In such case, the selected dependency can be considered as being accessible or readable to the primary medical imaging scanner, but as not being required or relied upon by the imaging protocol files that are committed on or pulled from the primary medical imaging scanner. However, note that it is possible for the selected dependency to nevertheless be used at a later time (e.g., such as during scanning).

Figure 12:
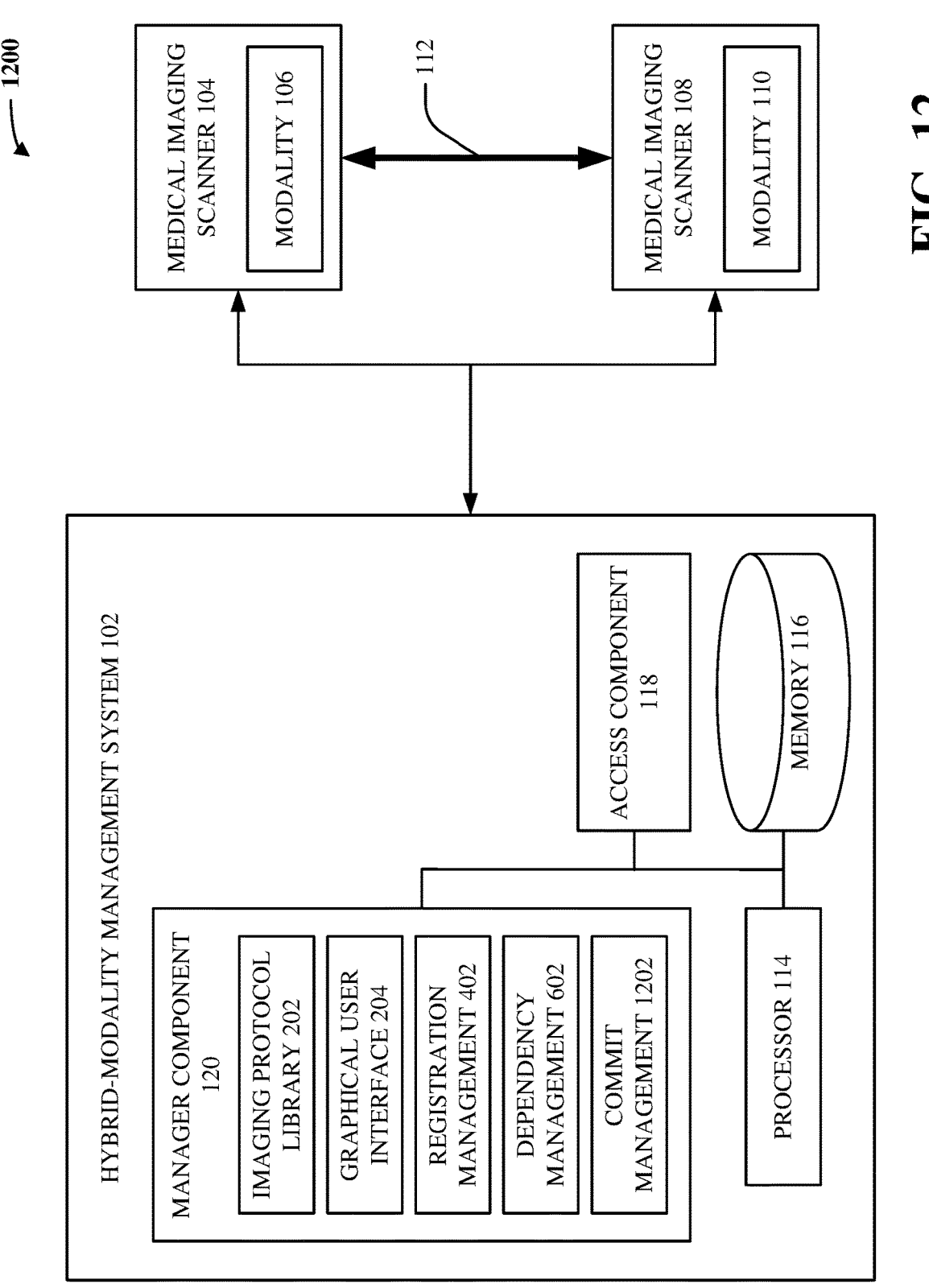
FIG. 12 illustrates a block diagram of an example, non-limiting system including commit management that facilitates automated imaging protocol management for hybrid modalities in accordance with one or more embodiments described herein.

FIG. 12 illustrates a block diagram of an example, non-limiting system 1200 including commit management that can facilitate automated imaging protocol management for hybrid modalities in accordance with one or more embodiments described herein. As shown, the system 1200 can, in some cases, comprise the same components as the system 600, and can further comprise commit management 1202.

In various embodiments, the manager component 120 can electronically perform or electronically facilitate the commit management 1202 for or with respect to the medical imaging scanner 104 or the medical imaging scanner 108. In various aspects, the commit management 1202 can be considered as a procedure or technique for synchronizing commit operations in a hybrid-aware fashion.

In various aspects, the manager component 120 can perform such synchronizing in a hybrid-aware fashion as follows. Whenever a user or technician instructs (via the graphical user interface 204) the manager component 120 to push imaging protocol files to a hybrid-modality setup for commitment, the manager component 120 can check or evaluate such imaging protocol files to determine which depend upon which. Based on such determination, the manager component 120 can ensure that the imaging protocol files are committed in order of dependency, with whichever imaging protocol files that do not depend upon any other imaging protocol files being committed first. This ordering or sequence of commitment can prevent situations in which an imaging protocol file is committed before another imaging protocol file on which it depends, which would be an inconsistency.

As a non-limiting example, suppose that it is desired to commit a first imaging protocol file on the medical imaging scanner 104 and a second imaging protocol file on the medical imaging scanner 108, where the first imaging protocol file references as a dependency the second imaging protocol file (e.g., the first and second imaging protocol files can together be considered as forming an imaging protocol transaction). In various aspects, the manager component 120 can push (e.g., simultaneously) the first and second imaging protocol files to the medical imaging scanner 104 and to the medical imaging scanner 108, respectively. Upon such push, the first and second imaging protocol files can be considered as respectively waiting in not-yet-committed menus of the medical imaging scanner 104 and of the medical imaging scanner 108. Now, because the manager component 120 can know (e.g., via parsing) that the first imaging protocol file depends upon the second imaging protocol file, the manager component 120 can instruct the medical imaging scanner 108 to commit the second imaging protocol file, and the manager component 120 can refrain from instructing the medical imaging scanner 104 to commit the first imaging protocol file. In various instances, the manager component 120 can wait to instruct the medical imaging scanner 104 to commit the first imaging protocol file, until after the manager component 120 receives from the second medical imaging scanner 108 a notification indicating that the second imaging protocol file has been successful or properly committed. Again, this can be considered as the manager component 120 automatically preventing a situation in which an imaging protocol file is committed before another file on which it depends or relies.

FIG. 13 illustrates a flow diagram of an example, non-limiting computer-implemented method 1300 that can facilitate hybrid-aware protocol commit management in accordance with one or more embodiments described herein. In various cases, the hybrid-modality management system 102 can facilitate the computer-implemented method 1300.

In various embodiments, act 1302 can include identifying, by an imaging protocol management service (e.g., via 120 of 102), a hybrid-modality setup comprising a primary medical imaging scanner (e.g., 104) and a secondary medical imaging scanner (e.g., 108).

In various aspects, act 1304 can include identifying, by the imaging protocol management service (e.g., via 120 of 102), a hybrid-modality imaging protocol transaction (e.g., a grouping of imaging protocol files that are pullable or pushable) comprising a first imaging protocol file and a second imaging protocol file that are respectively performable by the primary medical imaging scanner and the second medical imaging scanner.

In various instances, act 1306 can include simultaneously pushing, by the imaging protocol management service (e.g., via 120 of 102), the hybrid-modality imaging protocol transaction to the primary medical imaging scanner and to the secondary medical imaging scanner. That is, the first imaging protocol file can be pushed to the primary medical imaging scanner, and the second imaging protocol file can be pushed to the secondary medical imaging scanner.

In various cases, act 1308 can include instructing, by the imaging protocol management service (e.g., via 120 of 102), the secondary medical imaging scanner (e.g., the scanner whose protocols are depended or relied upon) to commit the hybrid-modality imaging protocol transaction (e.g., to commit the second imaging protocol file).

In various aspects, act 1310 can include determining, by the imaging protocol management service (e.g., via 120 of 102), whether the secondary medical imaging scanner has successfully committed the hybrid-modality imaging protocol transaction. If not (e.g., if the secondary medical imaging scanner has not finished committing the second imaging protocol file), the computer-implemented method 1300 can proceed back to act 1310. If so (e.g., if the secondary medical imaging scanner has finished committing the second imaging protocol file), the computer-implemented method 1300 can instead proceed to act 1312.

In various instances, act 1312 can include instructing, by the imaging protocol management service (e.g., via 120 of 102), the primary medical imaging scanner to commit the hybrid-modality imaging protocol transaction (e.g., to commit the first imaging protocol file).

Figure 14:
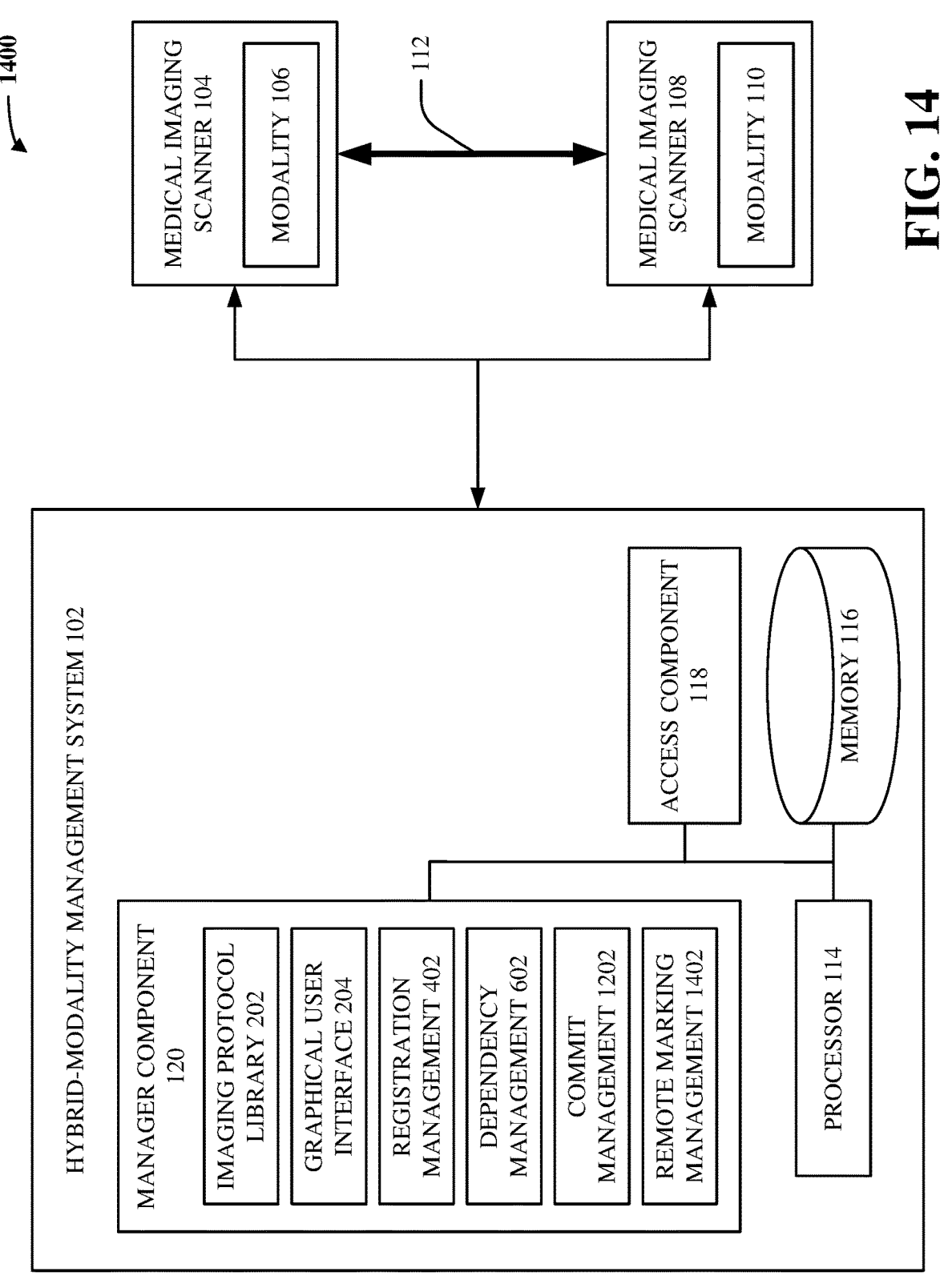
FIG. 14 illustrates a block diagram of an example, non-limiting system including remote marking management that facilitates automated imaging protocol management for hybrid modalities in accordance with one or more embodiments described herein.

FIG. 14 illustrates a block diagram of an example, non-limiting system 1400 including remote marking management that can facilitate automated imaging protocol management for hybrid modalities in accordance with one or more embodiments described herein. As shown, the system 1400 can, in some cases, comprise the same components as the system 1200, and can further comprise remote marking management 1402.

In various embodiments, the manager component 120 can electronically perform or electronically facilitate the remote marking management 1402 for or with respect to the medical imaging scanner 104 or the medical imaging scanner 108. In various aspects, the remote marking management

1402 can be considered as a procedure or technique for ensuring that the medical imaging scanners of a hybrid-modality setup properly or correctly make their imaging protocol files accessible or inaccessible to other medical imaging scanners in the hybrid-modality setup.

In various aspects, the manager component 120 can facilitate this as follows. Whenever the manager component 120 pushes an imaging protocol file to a medical imaging scanner, the manager component 120 can check or evaluate the imaging protocol file itself or the imaging protocol library 202, so as to determine whether that imaging protocol file depends upon, or is depended upon by, any other imaging protocol file. If not, the manager component 120 can instruct the medical imaging scanner to locally mark or designate that imaging protocol file as a single-modality protocol, meaning that the medical imaging scanner can prevent other scanners from accessing or reading the imaging protocol file. If so, the manager component 120 can instead instruct the medical imaging scanner to locally mark or designate that imaging protocol file as a hybrid-modality protocol, meaning that the medical imaging scanner can permit other scanners to access or read the imaging protocol file. In this way, the manager component 120 can be considered as helping to prevent situations in which an imaging protocol file is incorrectly or mistakenly locally marked as single-modality, which can wrongly prevent the imaging protocol file from being read or accessed by other medical imaging scanners that need it.

As a non-limiting example, suppose that the manager component 120 pushes a given imaging protocol file to the medical imaging scanner 104. In various aspects, the manager component 120 can parse the given imaging protocol file as well as any other imaging protocol files in the imaging protocol library 202, so as to determine whether the given imaging protocol file depends upon, or is depended upon by, any other imaging protocol file. If the given imaging protocol file does not depend upon, and is not depended upon by, any other imaging protocol file, the manager component 120 can conclude that the given imaging protocol file stands alone (e.g., is not involved in a hybrid-modality setup), and the manager component 120 can accordingly instruct the medical imaging scanner 104 to locally mark or designate the given imaging protocol file as single-modality. Such local marking or designation can prevent or prohibit other medical imaging scanners (e.g., 108) from reading or accessing the given imaging protocol file. Instead, if the given imaging protocol file depends upon at least one other imaging protocol file, or if the given imaging protocol file is depended upon by at least one other imaging protocol file, the manager component 120 can conclude that the given imaging protocol file does not stand alone (e.g., is involved in a hybrid-modality setup), and the manager component 120 can accordingly instruct the medical imaging scanner 104 to locally mark or designate the given imaging protocol file as hybrid-modality. Such local marking or designation can permit or allow other medical imaging scanners (e.g., 108) to read or access the given imaging protocol file. Again, the manager component 120 can be considered as helping to avoid a situation in which an erroneous local marking or designation prevents another medical imaging scanner (e.g., 108) from reading or accessing the given imaging protocol file when it needs to.

Note that the above paragraph applies to various embodiments that involve the manager component 120 instructing the medical imaging scanner 104 to locally mark or designate the given imaging protocol file as hybrid-modality, in response to determining that the given imaging protocol file depends upon, or is depended upon by, any other imaging protocol file. However, this is a mere non-limiting example. In other embodiments, the manager component 120 can instruct the medical imaging scanner 104 to locally mark or designate the given imaging protocol file as hybrid-modality, in response to determining that the given imaging protocol file is depended upon by any other imaging protocol file. In other words, the manager component 120 can, in such embodiments, refrain from asking or determining whether the given imaging protocol file depends upon any other imaging protocol files. Accordingly, in such other embodiments, a "depends-upon" imaging protocol file can be locally marked or designated as single-modality rather than hybrid-modality.

Figure 15:
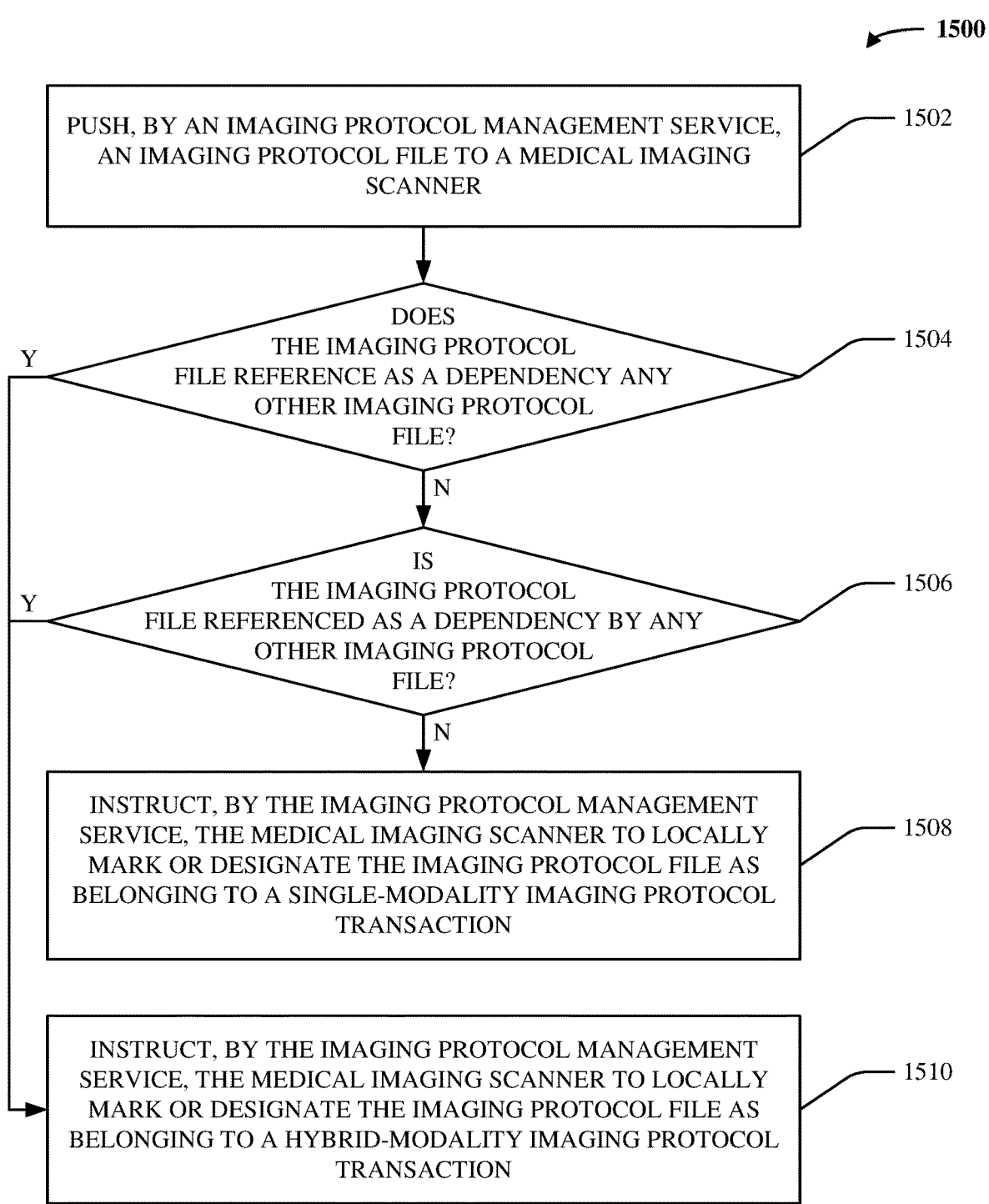
FIG. 15 illustrates a flow diagram of an example, non-limiting computer-implemented method that facilitates hybrid-aware remote protocol marking management in accordance with one or more embodiments described herein.

FIG. 15 illustrates a flow diagram of an example, non-limiting computer-implemented method 1500 that can facilitate hybrid-aware remote protocol marking management in accordance with one or more embodiments described herein. In various cases, the hybrid-modality management system 102 can facilitate the computer-implemented method 1500.

In various embodiments, act 1502 can include pushing, by an imaging protocol management service (e.g., via 120 of 102), an imaging protocol file to a medical imaging scanner (e.g., 104).

In various aspects, act 1504 can include determining, by the imaging protocol management service (e.g., 120 of 102), whether the imaging protocol file references as a dependency any other imaging protocol file. If not (e.g., if the imaging protocol file does not depend upon any other imaging protocol file), the computer-implemented method 1500 can proceed to act 1506. If so (e.g., if the imaging protocol file does depend upon another imaging protocol file), the computer-implemented method 1500 can instead proceed to act 1510.

In various instances, act 1506 can include determining, by the imaging protocol management service (e.g., 120 of 102), whether the imaging protocol file is referenced as a dependency by any other imaging protocol file. If not (e.g., if the imaging protocol file is not depended upon by any other imaging protocol file), the computer-implemented method 1500 can proceed to act 1508. If so (e.g., if the imaging protocol file is depended upon by another imaging protocol file), the computer-implemented method 1500 can instead proceed to act 1510.

In various cases, act 1508 can include instructing, by the imaging protocol management service (e.g., via 120 of 102), the medical imaging scanner to locally mark or designate the imaging protocol file as belonging to a single-modality imaging protocol transaction.

In various aspects, act 1510 can include instructing, by the imaging protocol management service (e.g., via 120 of 102), the medical imaging scanner to locally mark or designate the imaging protocol file as belonging to a hybrid-modality imaging protocol transaction.

Although not explicitly shown in FIG. 15, note that, in various embodiments, act 1504 can be omitted. Indeed, as mentioned above, various embodiments described herein can involve instructing a medical imaging scanner to locally mark or designate an imaging protocol file as hybrid-modality, in response to determining that the imaging protocol file is depended upon by at least one other imaging protocol file. That is, the determination can be focused on "depended upon" rather than "depends upon".

Figure 16:
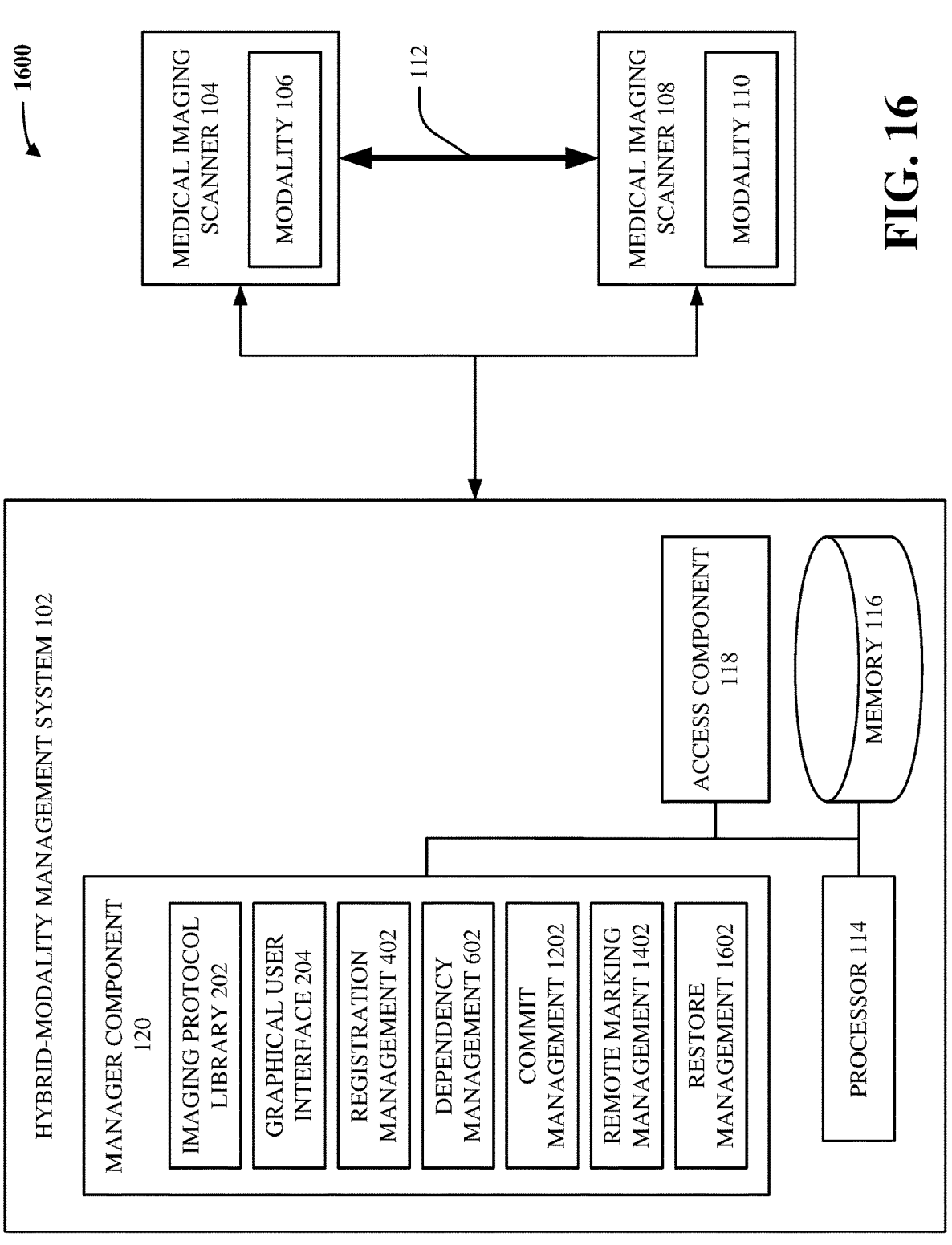
FIG. 16 illustrates a block diagram of an example, non-limiting system including restore management that facilitates automated imaging protocol management for hybrid modalities in accordance with one or more embodiments described herein.

FIG. 16 illustrates a block diagram of an example, non-limiting system 1600 including restore management that can facilitate automated imaging protocol management for hybrid modalities in accordance with one or more embodiments described herein. As shown, the system 1600 can, in some cases, comprise the same components as the system 1400, and can further comprise restore management 1602.

In various embodiments, the manager component 120 can electronically perform or electronically facilitate the restore management 1602 for or with respect to the medical imaging scanner 104 or the medical imaging scanner 108. In various aspects, the restore management 1602 can be considered as a procedure or technique for synchronizing restore operations in a hybrid-aware fashion.

In various aspects, whenever a medical imaging scanner is instructed to commit an imaging protocol transaction (e.g., one or more imaging protocol files), the medical imaging scanner can save the imaging protocol transaction in a backup file. In various instances, the medical imaging scanner can mark the backup file as a single-modality backup, if the imaging protocol transaction is not a hybrid-modality transaction (e.g., if the imaging protocol transaction does not include any imaging protocol files that depend upon, or that are depended upon by, any other imaging protocol files). In various cases, the medical imaging scanner can instead mark the backup file as a hybrid-modality backup file, if the imaging protocol transaction is a hybrid-modality transaction (e.g., if the imaging protocol transaction include at least one imaging protocol file that depends upon, or that is depended upon by, any other imaging protocol file). After saving the backup file, the medical imaging scanner can then commit the imaging protocol transaction (e.g., can then commit the one or more imaging protocol files).

In various aspects, whenever a medical imaging scanner is instructed to restore its internal state to an imaging protocol transaction that it had previously committed, the medical imaging scanner can internally identify a backup file corresponding to that imaging protocol transaction. In various instances, the medical imaging scanner can restore that imaging protocol transaction using the identified backup file. Note that such restoration can cause the medical imaging scanner to lose imaging protocol transactions that are not reflected in the identified backup file. Moreover, in various cases, the medical imaging scanner can determine whether the identified backup file was marked as a single-modality backup file or instead as a hybrid-modality backup file. If the identified backup file was marked as single-modality, the medical imaging scanner can delete the identified backup file after restoring it. On the other hand, if the identified backup file was instead marked as hybrid-modality, the medical imaging scanner can append an identifier (e.g., a naming extension, such as ".bck") to the identified backup file (unless the identified backup file is already appended with the identifier). In various aspects, the medical imaging scanner can then refrain from deleting the identified backup file, and the medical imaging scanner can instead delete all other of its backup files that are: marked as hybrid-modality; and that are appended with the identifier.

Now, in various aspects, whenever a user or technician instructs (via the graphical user interface 204) the manager component 120 to restore a prior imaging protocol transaction on a hybrid-modality setup, the manager component 120 can determine which medical imaging scanners in that hybrid-modality setup depend upon which other medical imaging scanners in that hybrid-modality setup. In various instances, the manager component 120 can facilitate this determination by parsing whatever imaging protocol files are involved in the prior imaging protocol transaction. In various cases, the manager component 120 can then instruct the medical imaging scanners of that hybrid-modality setup to restore the prior imaging protocol transaction in order of dependency, beginning with whichever medical imaging scanner is not depended upon by any other medical imaging scanner in the hybrid-modality setup. In other words, the manager component 120 can cause restore operations to be performed in a reverse sequential order as compared to commit operations (e.g., commit operations can, as described herein, be performed in order of dependency starting with whichever scanner does not depend upon any other scanner; whereas restore operations can, as described herein, be performed in order of dependency starting with whichever scanner is not depended upon by any other scanner). Such ordering or sequence of restoration can help to prevent the creation of protocol inconsistencies. After all, a medical imaging scanner can lose current protocol trans-action information that is not reflected or captured in its restored backup file. So, if a given scanner in a hybrid-modality setup depends upon another scanner in the hybrid-modality setup, and if that another scanner is restored first, then it is possible that the current imaging protocol trans-action information of that given scanner depends upon imaging protocol transaction information that was just lost by the restoration of the another scanner. The manager component 120 can avoid such situations by performing restore operations in order of dependency, starting with whichever scanner is not depended upon by any others.

As a non-limiting example, suppose that the user or technician instructs the manager component 120 to restore a previous hybrid-modality imaging protocol transaction on the hybrid-modality setup formed by the medical imaging scanner 104 and the medical imaging scanner 108, where the previous hybrid-modality imaging protocol transaction com-prises a first imaging protocol file performable by the medical imaging scanner 104 and a second imaging protocol file performable by the medical imaging scanner 108. In various aspects, the manager component 120 can determine (e.g., via parsing) whether the first imaging protocol file depends upon the second imaging protocol file. If so, the manager component 120 can conclude that the medical imaging scanner 104 is the primary scanner (e.g., is not depended upon by the medical imaging scanner 108). So, the manager component 120 can instruct the medical imaging scanner 104 to restore the first imaging protocol file first, and the manager component 120 can instruct the medical imag-ing scanner 108 to restore the second imaging protocol file afterward. On the other hand, if not, the manager component 120 can conclude that the medical imaging scanner 104 is the secondary scanner (e.g., is depended upon by the medi-cal imaging scanner 108). So, the manager component 120 can instruct the medical imaging scanner 108 to restore the second imaging protocol file first, and the manager compo-nent 120 can instruct the medical imaging scanner 104 to restore the first imaging protocol file afterward.

Figure 18:
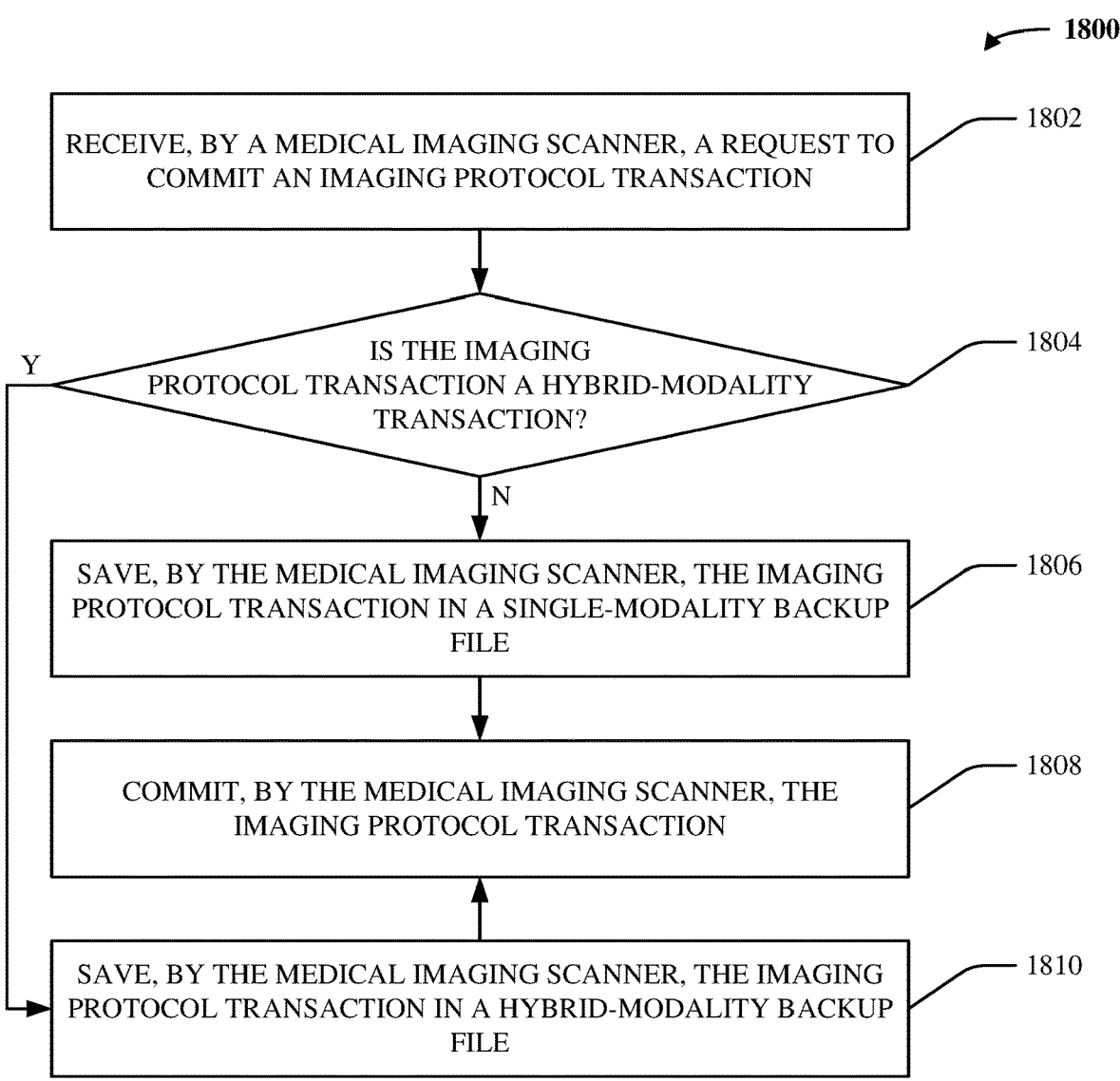

FIGS. 17-19 illustrate flow diagrams of example, non-limiting computer-implemented methods 1700, 1800, and 1900 that can facilitate hybrid-aware protocol restore man-agement in accordance with one or more embodiments described herein. In various cases, the hybrid-modality management system 102 can facilitate the computer-imple-mented method 1700. In various cases, the medical imaging scanner 104 or the medical imaging scanner 108 can facili-tate the computer-implemented methods 1800 and 1900.

First, consider FIG. 17. In various embodiments, act 1702 can include identifying, by an imaging protocol manage-ment service (e.g., via 120 of 102), a hybrid-modality setup comprising a primary medical imaging scanner (e.g., 104) and a secondary medical imaging scanner (e.g., 108).

In various aspects, act 1704 can include identifying, by the imaging protocol management service (e.g., via 120 of 102), a previously-committed hybrid-modality imaging pro-tocol transaction (e.g., a group of imaging protocol files) that is to be restored on the hybrid-modality setup.

In various instances, act 1706 can include instructing, by the imaging protocol management service (e.g., via 120 of 102), the primary medical imaging scanner to restore the previously-committed hybrid-modality imaging protocol transaction.

In various cases, act 1708 can include determining, by the imaging protocol management service (e.g., via 120 of 102), whether the primary medical imaging scanner has success-fully restored the previously-committed hybrid-modality imaging protocol transaction. If not (e.g., if the primary medical imaging scanner has not finished restoring the previously-committed hybrid-modality imaging protocol transaction), the computer-implemented method 1700 can proceed back to act 1708. If so (e.g., if the primary medical imaging scanner has finished restoring the previously-com-mitted hybrid-modality imaging protocol transaction), the computer-implemented method 1700 can instead proceed back to act 1710.

In various aspects, act 1710 can include instructing, by the imaging protocol management service (e.g., via 120 of 102), the secondary medical imaging scanner to restore the pre-viously-committed hybrid-modality imaging protocol trans-action.

Now, consider FIG. 18. In various embodiments, act 1802 can include receiving, by a medical imaging scanner (e.g., 104), a request to commit an imaging protocol transaction (e.g., one or more imaging protocol files).

In various aspects, act 1804 can include determining, by the medical imaging scanner, whether the imaging protocol transaction is a hybrid-modality transaction. If not (e.g., if the imaging protocol transaction does not involve any imag-ing protocol files that depend upon, or that are depended upon by, any other imaging protocol files), the computer-implemented method 1800 can proceed to act 1806. If so (e.g., if the imaging protocol transaction does involve at least one imaging protocol file that depends upon, or that is depended upon by, any other imaging protocol files), the computer-implemented method 1800 can instead proceed to act 1810.

In various instances, act 1806 can include saving, by the medical imaging scanner, the imaging protocol transaction in a single-modality backup file.

In various cases, act 1808 can include committing, by the medical imaging scanner, the imaging protocol transaction.

In various aspects, act 1810 can include saving, by the medical imaging scanner, the imaging protocol file in a hybrid-modality back file. In various instances, the com-puter-implemented method 1800 can then proceed to act 1810.

Now, consider FIG. 19. In various embodiments, act 1902 can include receiving, by a medical imaging scanner (e.g., 104), a request to restore a previously-committed imaging protocol transaction.

In various aspects, act 1904 can include identifying, by the medical imaging scanner, a backup file corresponding to the previously-committed imaging protocol transaction.

In various instances, act 1906 can include restoring, by the medical imaging scanner, the previously-committed imaging protocol transaction based on the backup file.

In various cases, act 1908 can include determining, by the medical imaging scanner, whether the backup file is marked as hybrid-modality. If not (e.g., if the backup file is marked as a single-modality backup file), the computer-implemented method 1900 can proceed to act 1910. If so (e.g., if the backup file is marked as a hybrid-modality backup file), the computer-implemented method 1900 can instead proceed to act 1912.

In various aspects, act 1910 can include deleting, by the medical imaging scanner, the backup file.

In various instances, act 1912 can include appending, by the medical imaging scanner and if not already appended, an identifier (e.g., a ".bck" extension) to the backup file.

In various cases, act 1914 can include deleting, by the medical imaging scanner, all other hybrid-modality backup files that are appended with the identifier.

Figure 20:
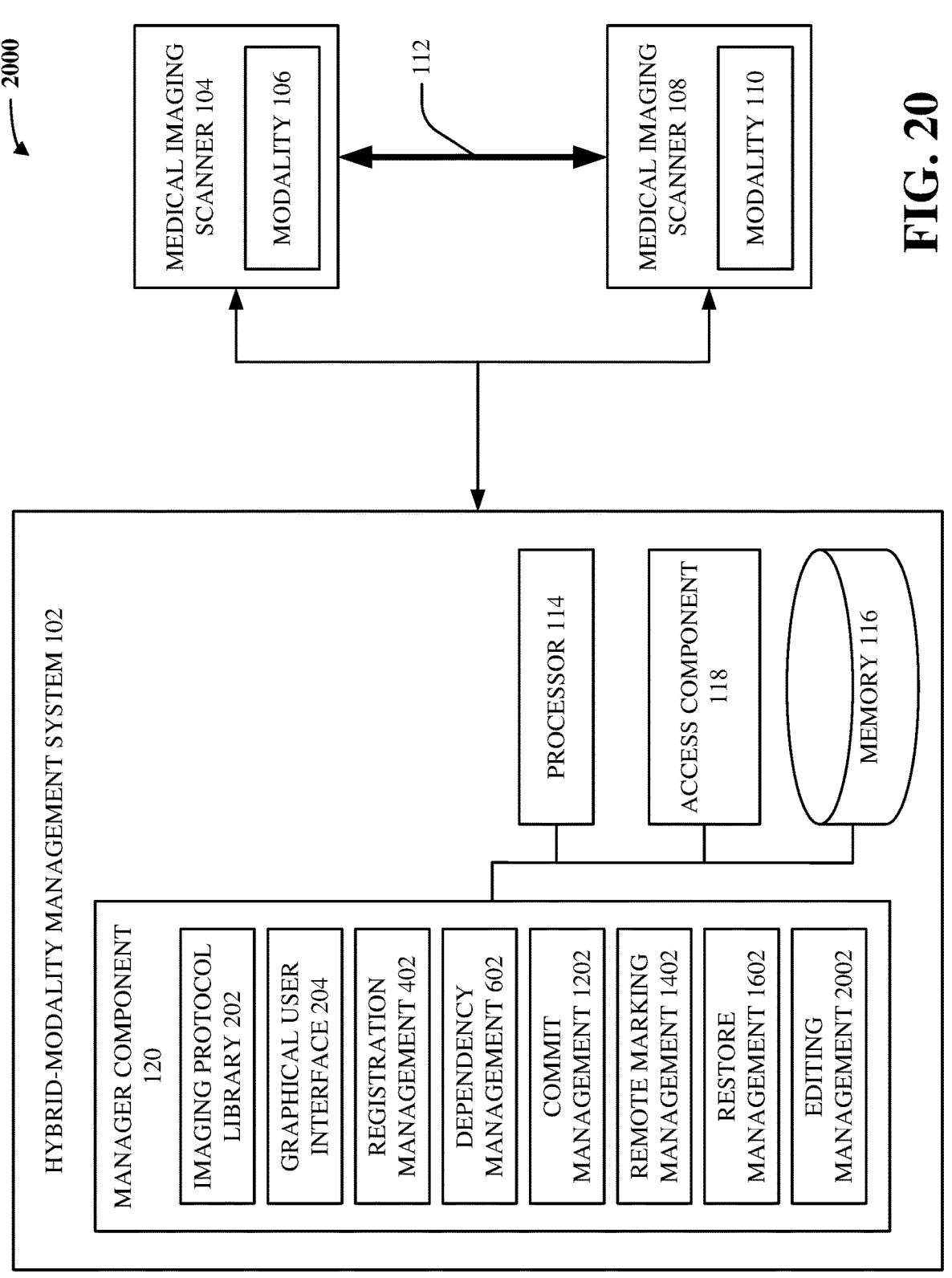
FIG. 20 illustrates a block diagram of an example, non-limiting system including editing management that facilitates automated imaging protocol management for hybrid modalities in accordance with one or more embodiments described herein.

FIG. 20 illustrates a block diagram of an example, non-limiting system 2000 including editing management that can facilitate automated imaging protocol management for hybrid modalities in accordance with one or more embodiments described herein. As shown, the system 2000 can, in some cases, comprise the same components as the system 1600, and can further comprise editing management 2002.

In various embodiments, the manager component 120 can electronically perform or electronically facilitate the editing management 2002 for or with respect to the medical imaging scanner 104 or the medical imaging scanner 108. In various aspects, the editing management 2002 can be considered as a procedure or technique for ensuring that the imaging protocol files of a hybrid-modality setup are not mistakenly made inconsistent by one-sided editing.

In various aspects, the manager component 120 can facilitate this as follows. Whenever a user or technician instructs (via the graphical user interface 204) the manager component 120 to launch an editor of an imaging protocol file, the manager component 120 can check or evaluate the imaging protocol file itself or the imaging protocol library 202, so as to determine whether that imaging protocol file depends upon, or is depended upon by, any other imaging protocol file. If not, the manager component 120 can launch the editor of that imaging protocol file. If so, the manager component 120 can launch the edit of that imaging protocol file and can also launch the editors of whatever other imaging protocol files that depend upon, or that are depended upon by, that imaging protocol file. In this way, the manager component 120 can be considered as helping to prevent situations in which an imaging protocol file is edited while other imaging protocol files that it depends on or that depend on it are mistakenly or erroneously left unedited.

Figure 21:
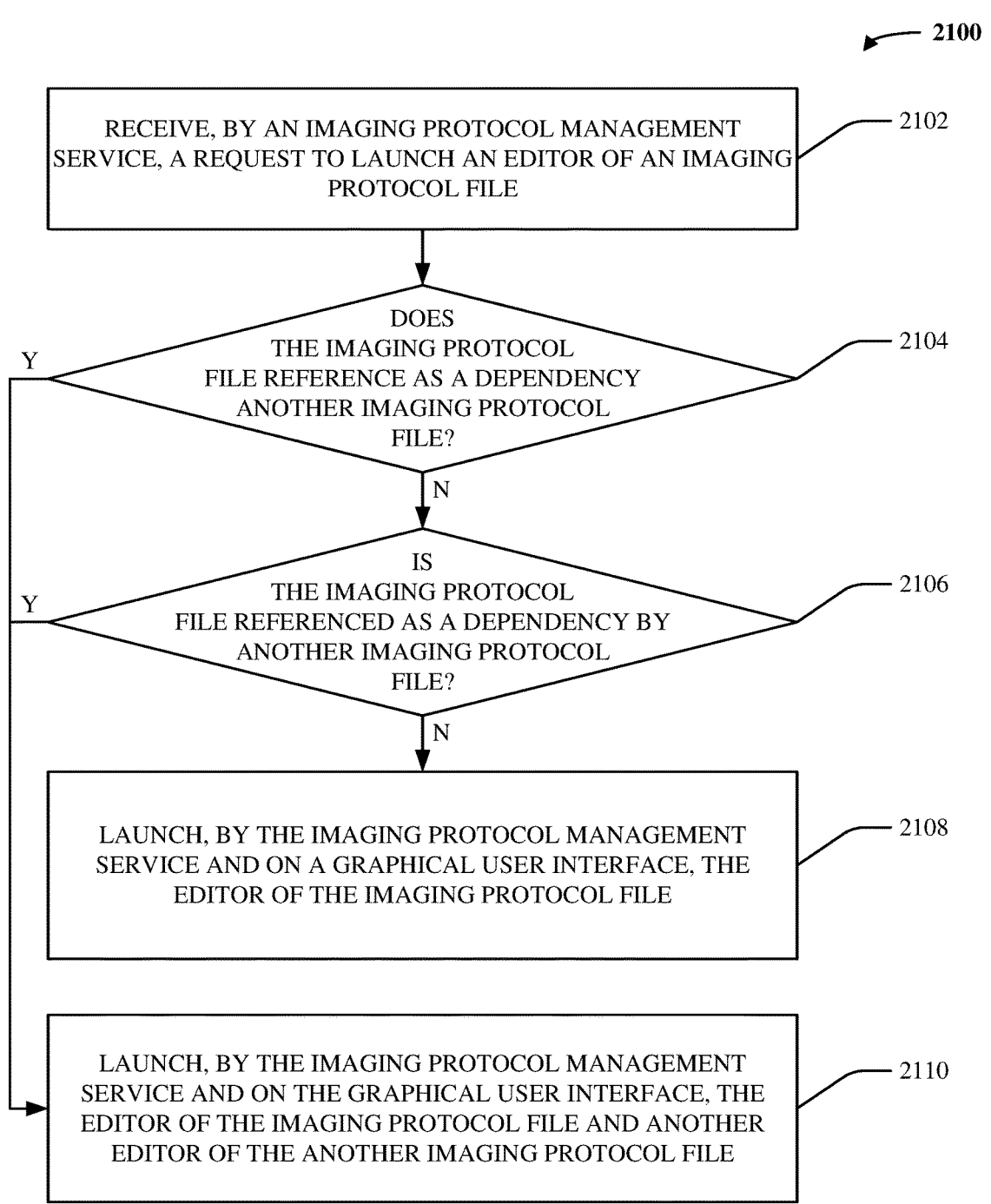
FIG. 21 illustrates a flow diagram of an example, non-limiting computer-implemented method that facilitates hybrid-aware protocol editing management in accordance with one or more embodiments described herein.

FIG. 21 illustrates a flow diagram of an example, non-limiting computer-implemented method 2100 that can facilitate hybrid-aware protocol editing management in accordance with one or more embodiments described herein. In various cases, the hybrid-modality management system 102 can facilitate the computer-implemented method 2100.

In various embodiments, act 2102 can include receiving, by an imaging protocol management service (e.g., via 120 of 102), a request to launch an editor of an imaging protocol file.

In various aspects, act 2104 can include determining, by the imaging protocol management service (e.g., 120 of 102), whether the imaging protocol file references as a dependency another imaging protocol file. If not (e.g., if the imaging protocol file does not depend upon any other imaging protocol file), the computer-implemented method 2100 can proceed to act 2106. If so (e.g., if the imaging protocol file does depend upon another imaging protocol file), the computer-implemented method 2100 can instead proceed to act 2110.

In various instances, act 2106 can include determining, by the imaging protocol management service (e.g., 120 of 102), whether the imaging protocol file is referenced as a dependency by another imaging protocol file. If not (e.g., if the imaging protocol file is not depended upon by any other imaging protocol file), the computer-implemented method 2100 can proceed to act 2108. If so (e.g., if the imaging protocol file is depended upon by another imaging protocol file), the computer-implemented method 2100 can instead proceed to act 2110.

In various cases, act 2108 can include launching, by the imaging protocol management service (e.g., via 120 of 102) and on a graphical user interface (e.g., 204), the editor of the imaging protocol file.

In various aspects, act 2110 can include instructing, by the imaging protocol management service (e.g., via 120 of 102), the editor of the imaging protocol file and another editor of the another imaging protocol file.

Note that the embodiments described above regarding FIGS. 20-21 can be considered as pertaining to editors that are launched on a file-wise basis. It is to be appreciated that such embodiments are mere non-limiting examples. In other embodiments, editors can instead be launched on a scanner-wise basis. In such other embodiments, the manager component 120 can facilitate the editing management 2002 as follows. Whenever a user or technician instructs the manager component 120 to launch an editor of any given medical imaging scanner, the manager component 120 can check its internal records, so as to determine whether that given medical imaging scanner is marked, designated, or registered as belonging to a hybrid-modality setup. If the given medical imaging scanner is not marked, designated, or registered as belonging to a hybrid-modality setup, the manager component 120 can launch the editor of that given medical imaging scanner. On the other hand, if the given medical imaging scanner is marked, designated, or registered as belonging to a hybrid-modality setup, the manager component 120 can launch the edit of that given medical imaging scanner and can also launch the editors of whatever other medical imaging scanners are marked, designated, or registered as belonging to that same hybrid-modality setup.

As a non-limiting example, suppose that a user or technician instructs (via the graphical user interface 204) the manager component 120 to launch an editor of the medical imaging scanner 104. As described above, the registration management 402 can have caused the manager component 120 to mark, designate, or register the medical imaging scanner 104 as forming a hybrid-modality setup with the medical imaging scanner 108. Such marking, designation, or registration can cause the manager component 120 to not launch the editor of the medical imaging scanner 104 in isolation. Instead, such marking, designation, or registration can cause the manager component 120 to launch the editor of the medical imaging scanner 104 in parallel or simultaneously with an editor of the medical imaging scanner 108. This can be notwithstanding the fact that the user or technician did not instruct the manager component 120 to launch the editor of the medical imaging scanner 108. Accordingly, such parallel launching of editors can be considered as conveying to the user or technician that whatever edits they desire to make to the medical imaging scanner 104 might need to be commensurately made to the medical imaging scanner 108.

Figure 22:
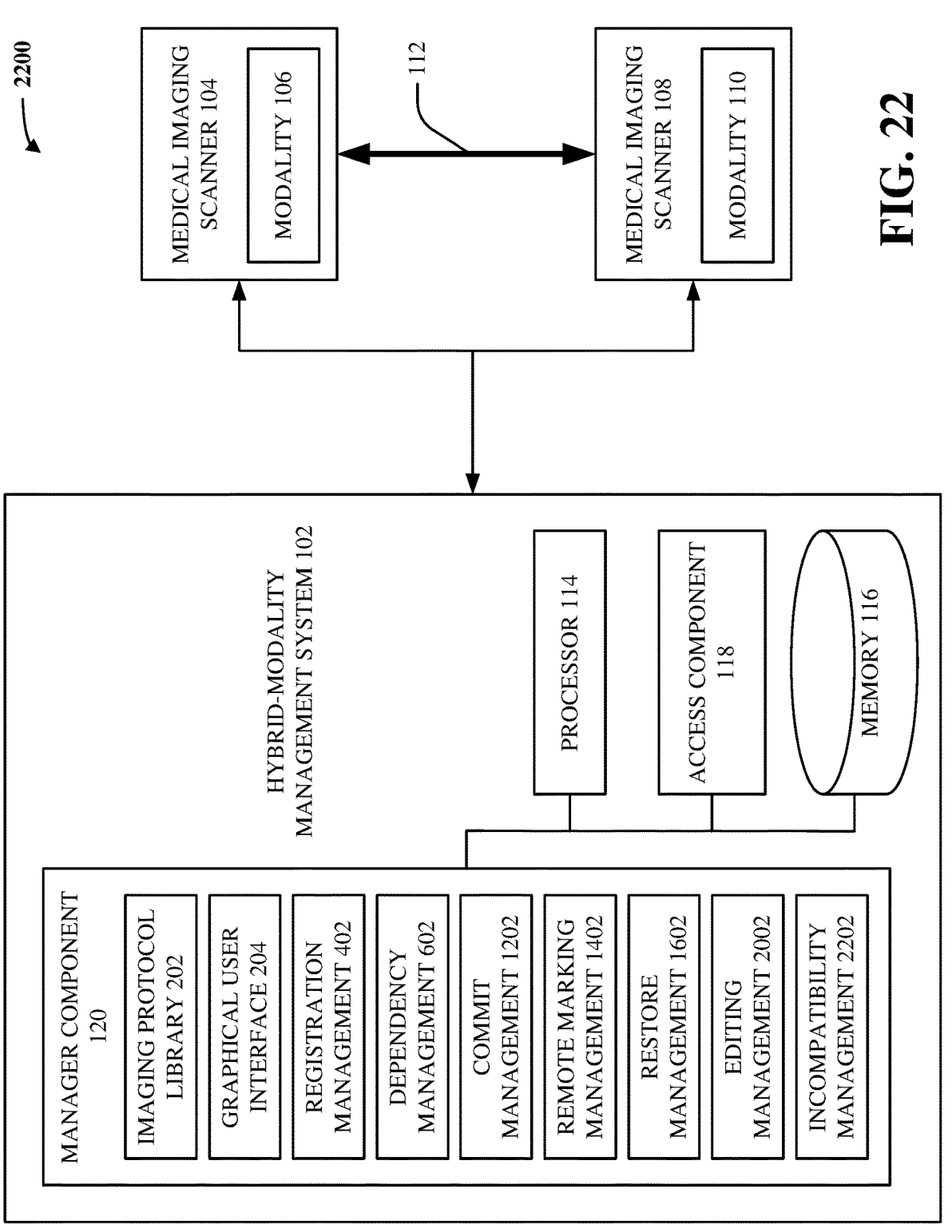
FIG. 22 illustrates a block diagram of an example, non-limiting system including incompatibility management that facilitates automated imaging protocol management for hybrid modalities in accordance with one or more embodiments described herein.

FIG. 22 illustrates a block diagram of an example, non-limiting system 2200 including incompatibility management that can facilitate automated imaging protocol management for hybrid modalities in accordance with one or more embodiments described herein. As shown, the system 2200 can, in some cases, comprise the same components as the system 2000, and can further comprise incompatibility management 2202.

In various embodiments, the manager component 120 can electronically perform or electronically facilitate the incompatibility management 2202 for or with respect to the medical imaging scanner 104 or the medical imaging scanner 108. In various aspects, the incompatibility management 2202 can be considered as a procedure or technique for curing scanner-protocol incompatibilities in a hybrid-aware fashion.

In various aspects, the manager component 120 can perform such curing in a hybrid-aware fashion as follows. Whenever a user or technician instructs (via the graphical user interface 204) the manager component 120 to push imaging protocol files to a hybrid-modality setup, the manager component 120 can check or evaluate such imaging protocol files to determine whether they are properly performable on the hybrid-modality setup (e.g., whether they are compatible with the hardware or software of the hybrid-modality setup). If one or more imaging protocol files are found to be hardware-incompatible or software-incompatible with the hybrid-modality setup, the manager component 120 can identify in the imaging protocol library 202 appropriate substitutes for those one or more imaging protocol files, and the manager component 120 can accordingly push those substitutes to the hybrid-modality setup.

As a non-limiting example, suppose that it is desired to respectively push a first imaging protocol file and a second imaging protocol file to the medical imaging scanner 104 and to the medical imaging scanner 108. In various instances, the manager component 120 can respectively check or evaluate whether the first imaging protocol file and the second imaging protocol file are performable on or otherwise compatible with the medical imaging scanner 104 and the medical imaging scanner 108. This determination can be facilitated by leveraging or querying the set of modality indicators 304 or the set of model indicators 306 with the registered metadata pertaining to the medical imaging scanner 104 and to the medical imaging scanner 108. Now, suppose that the manager component 120 determines that the first imaging protocol file is performable on (e.g., is compatible with the image-capture modality, with the model number, and with the software version of) the medical imaging scanner 104. However, further suppose that the manager component 120 determines that the second imaging protocol file is not performable on (e.g., is not compatible with the image-capture modality, with the model number, or with the software version of) the medical imaging scanner 108. In such case, the manager component 120 can leverage the set of substitute indicators 308, so as to identify a third imaging protocol file that is a clinically relevant or related to (e.g., that is designed to visualize the same anatomical structure for the same clinical purpose as) the second imaging protocol file, where the third imaging protocol file is performable on (e.g., is compatible with the image-capture modality, with the model number, or with the software version of) the medical imaging scanner 108. Accordingly, rather than respectively pushing the first and second imaging protocol files to the medical imaging scanner 104 and the medical imaging scanner 108, the manager component 120 can instead respectively push the first and third imaging protocol files to the medical imaging scanner 104 and the medical imaging scanner 108. In this way, the manager component 120 can be considered as automatically helping to cure a detected scanner-protocol incompatibility.

Figure 23:
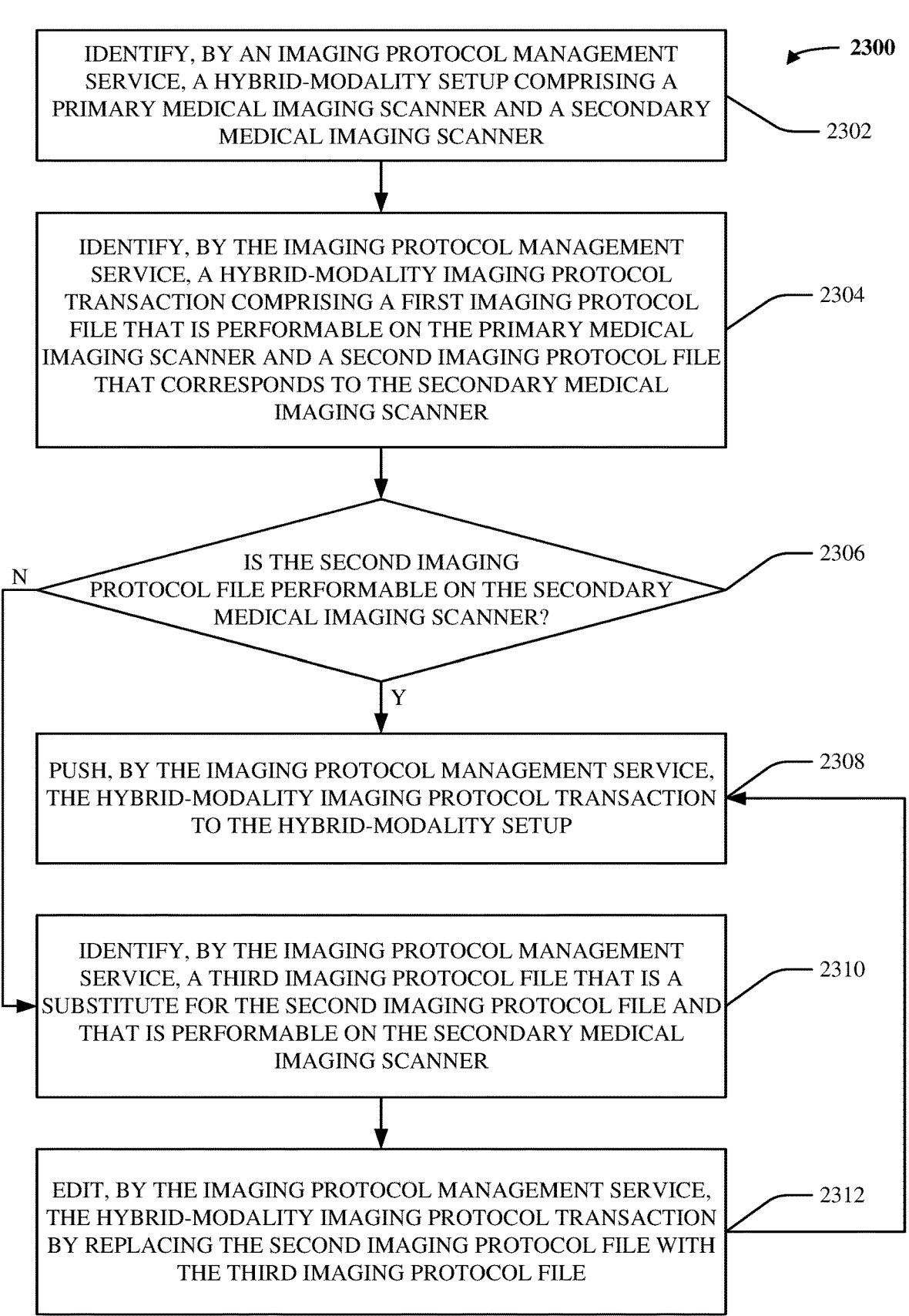
FIG. 23 illustrates a flow diagram of an example, non-limiting computer-implemented method that facilitates hybrid-aware scanner-protocol incompatibility management in accordance with one or more embodiments described herein.

FIG. 23 illustrates a flow diagram of an example, non-limiting computer-implemented method 2300 that can facilitate hybrid-aware scanner-protocol incompatibility management in accordance with one or more embodiments described herein. In some cases, the hybrid-management management system 102 can facilitate the computer-implemented method 2300.

In various embodiments, at 2302 can include identifying, by an imaging protocol management service (e.g., via 120 of 102), a hybrid-modality setup comprising a primary medical imaging scanner (e.g., 104) and a secondary medical imaging scanner (e.g., 108).

In various aspects, act 2304 can include identifying, by the imaging protocol management service (e.g., via 120 of 102), a hybrid-modality imaging protocol transaction comprising a first imaging protocol file that is performable on the primary medical imaging scanner and a second imaging protocol file that corresponds to (e.g., that is desired to be pushed to) the secondary medical imaging scanner.

In various instances, act 2306 can include determining, by the imaging protocol management service (e.g., via 120 of 102), whether the second imaging protocol file is performable on the second medical imaging scanner. If not (e.g., if the second imaging protocol file is not compatible with an image-capture modality of, with a model number of, or with a software version of the secondary medical imaging scanner), the computer-implemented method 2300 can proceed to act 2310. If so (e.g., if the second imaging protocol file is compatible with an image-capture modality of, with a model number of, and with a software version of the secondary medical imaging scanner), the computer-implemented method 2300 can instead proceed to act 2308.

In various cases, act 2308 can include pushing, by the imaging protocol management service (e.g., via 120 of 102), the hybrid-modality imaging protocol transaction to the hybrid-modality setup.

In various aspects, act 2310 can include identifying, by the imaging protocol management service (e.g., via 120 of 102), a third imaging protocol file that is a clinical substitute for the second imaging protocol file and that is performable on (e.g., that is compatible with an image-capture modality of, with a model number of, and with a software version of) the secondary medical imaging scanner.

In various instances, act 2312 can include editing, by the imaging protocol management service (e.g., via 120 of 102), the hybrid-modality imaging protocol transaction by replacing the second imaging protocol file with the third imaging protocol file. However, this is a mere non-limiting example. In other cases, act 2312 can include editing, by the imaging protocol management service (e.g., via 120 of 102), the hybrid-modality imaging protocol transaction by adding the third imaging protocol file as an alternative to the second imaging protocol file. In either case, the computer-implemented method 2300 can then proceed to act 2308.

Figure 24:
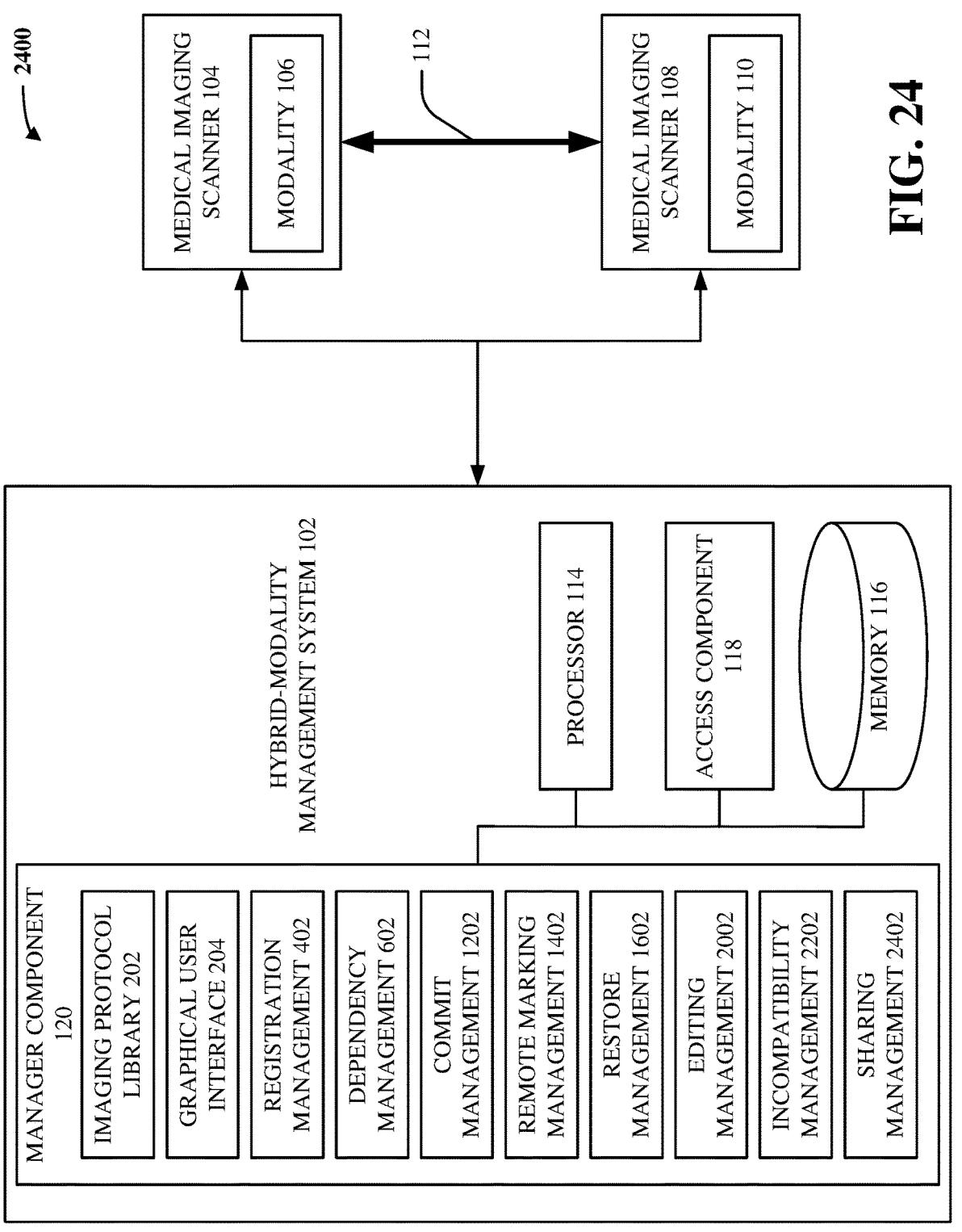
FIG. 24 illustrates a block diagram of an example, non-limiting system including sharing management that facilitates automated imaging protocol management for hybrid modalities in accordance with one or more embodiments described herein.

FIG. 24 illustrates a block diagram of an example, non-limiting system 2400 including sharing management that can facilitate automated imaging protocol management for hybrid modalities in accordance with one or more embodiments described herein. As shown, the system 2400 can, in some cases, comprise the same components as the system 2200, and can further comprise sharing management 2402.

In various embodiments, the sharing management 2402 can include cross-model sharing of imaging protocol files. As mentioned above, an imaging protocol file can be model-specific. In various aspects, cross-model sharing can involve the manager component 120 automatically converting or editing an imaging protocol file so that it is no longer compatible with an original scanner model and is instead compatible with some other scanner model. In various instances, a hybrid-modality imaging protocol transaction can involve at least one first imaging protocol file that depends upon at least one second imaging protocol file. For some scanner models for which protocol sharing is desired, the entire hybrid-modality imaging protocol transaction can be converted and thus shared between the models. For other scanner models for which protocol sharing is desired, less than an entirety of the hybrid-modality imaging protocol transaction can be converted and thus shared between the models (e.g., the scanner models can be only partially compatible with each other, such that only the at least one first imaging protocol file is convertible and sharable between the models, or such that only the at least one second imaging protocol file is convertible and shared between the models). For yet other scanner models for which protocol sharing is desired, none of the hybrid-modality imaging protocol transaction can be converted and thus shared between the models (e.g., the scanner models can be totally incompatible with each other, such that none of the at least one first imaging protocol file and none of the at least one second imaging protocol file are convertible and sharable between the models). In various aspects, there can be a model compatibility matrix that is known or deemed to define which scanner models are totally or partially compatible or incompatible with each other. In various instances, the manager component 120 can store, maintain, or otherwise access the model compatibility matrix, and the manager component 120 can leverage or bootstrap the model compatibility matrix when launching a converter for any given imaging protocol file or transaction.

In various embodiments, the sharing management 2402 can include cross-modality sharing of imaging protocol files. As mentioned above, an imaging protocol file can be modality-specific. In various aspects, cross-modality sharing can involve the manager component 120 automatically converting or editing an imaging protocol file so that it is no longer compatible with an original image-capture modality and is instead compatible with some other image-capture modality. Similar to above, the manager component 120 can facilitate this by leveraging or bootstrapping any suitable modality compatibility matrix in conjunction with any suitable converters.

Although not explicitly shown in the figures, remote agents of the hybrid-modality management system 102 can be locally installed on the medical imaging scanner 104 and the medical imaging scanner 108, and such agents can communicate (e.g., via a REST application programming interface) with the access component 118.

In various instances, machine learning algorithms or models can be implemented in any suitable way to facilitate any suitable aspects described herein. To facilitate some of the above-described machine learning aspects of various embodiments, consider the following discussion of artificial intelligence (AI). Various embodiments described herein can employ artificial intelligence to facilitate automating one or more features or functionalities. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system or environment from a set of observations as captured via events or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events or data.

Such determinations can result in the construction of new events or actions from a set of observed events or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes or systems (e.g., support vector machines, neural networks, expert systems, Bayesian belief networks, fuzzy logic, data fusion engines, and so on) in connection with performing automatic or determined action in connection with the claimed subject matter. Thus, classification schemes or systems can be used to automatically learn and perform a number of functions, actions, or determinations.

A classifier can map an input attribute vector, $z=(z_1, z_2, z_3, z_4, z_n)$, to a confidence that the input belongs to a class, as by $f(z)=$confidence(class). Such classification can employ a probabilistic or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, or probabilistic classification models providing different patterns of independence, any of which can be employed. Classification as used herein also is inclusive of statistical regression that is utilized to develop models of priority.

Figure 25:
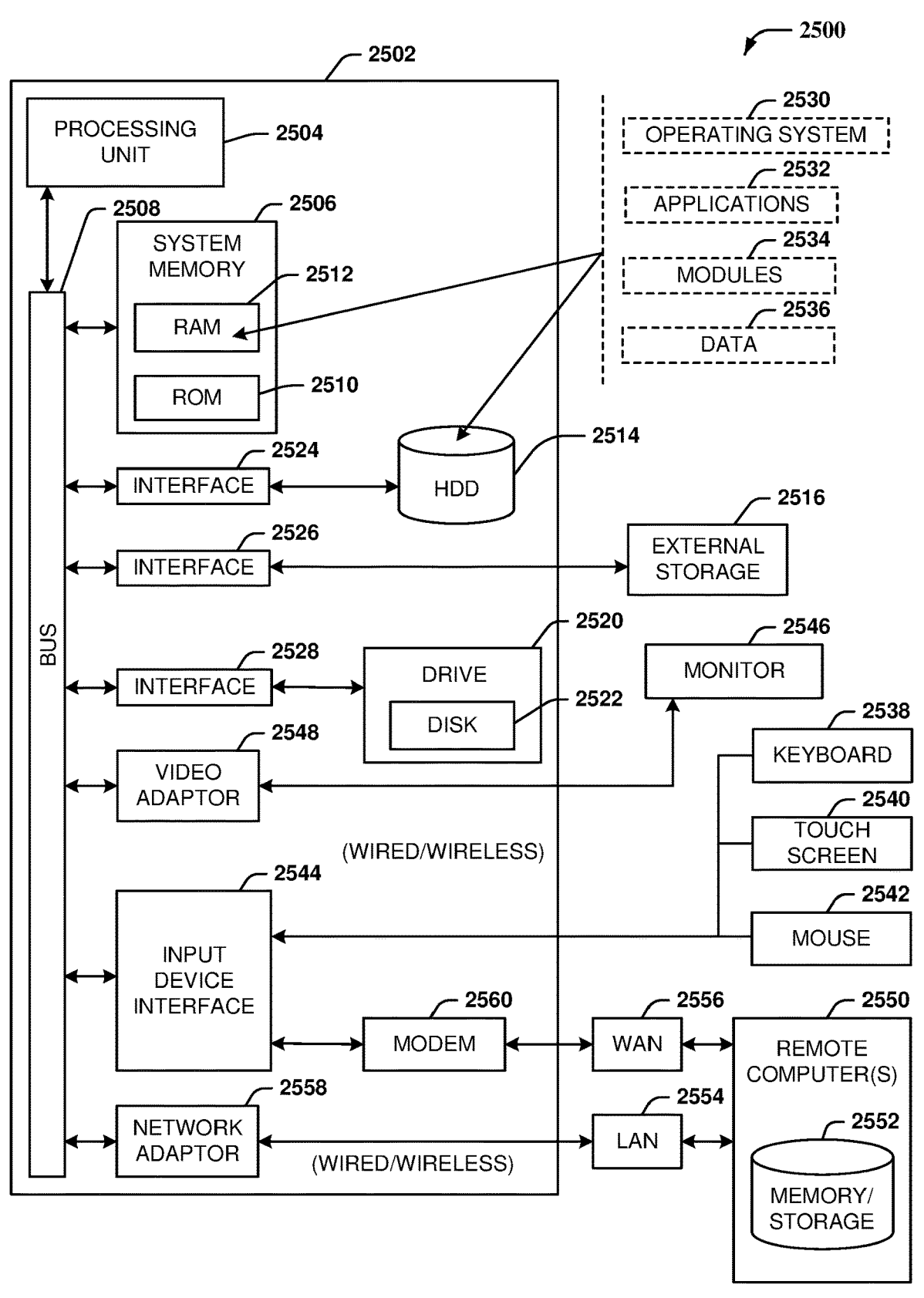
FIG. 25 illustrates a block diagram of an example, non-limiting operating environment in which one or more embodiments described herein can be facilitated.

In order to provide additional context for various embodiments described herein, FIG. 25 and the following discussion are intended to provide a brief, general description of a suitable computing environment 2500 in which the various embodiments of the embodiment described herein can be implemented. While the embodiments have been described above in the general context of computer-executable instructions that can run on one or more computers, those skilled in the art will recognize that the embodiments can be also implemented in combination with other program modules or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IOT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 25, the example environment 2500 for implementing various embodiments of the aspects described herein includes a computer 2502, the computer 2502 including a processing unit 2504, a system memory 2506 and a system bus 2508. The system bus 2508 couples system components including, but not limited to, the system memory 2506 to the processing unit 2504. The processing unit 2504 can be any of various commercially available processors. Dual microprocessors and other multi-processor architectures can also be employed as the processing unit 2504.

The system bus 2508 can be any of several types of bus structure that can further interconnect to a memory bus (with or without a memory controller), a peripheral bus, and a local bus using any of a variety of commercially available bus architectures. The system memory 2506 includes ROM 2510 and RAM 2512. A basic input/output system (BIOS) can be stored in a non-volatile memory such as ROM, erasable programmable read only memory (EPROM), EEPROM, which BIOS contains the basic routines that help to transfer information between elements within the computer 2502, such as during startup. The RAM 2512 can also include a high-speed RAM such as static RAM for caching data.

The computer 2502 further includes an internal hard disk drive (HDD) 2514 (e.g., EIDE, SATA), one or more external storage devices 2516 (e.g., a magnetic floppy disk drive (FDD) 2516, a memory stick or flash drive reader, a memory card reader, etc.) and a drive 2520, e.g., such as a solid state drive, an optical disk drive, which can read or write from a disk 2522, such as a CD-ROM disc, a DVD, a BD, etc. Alternatively, where a solid state drive is involved, disk 2522 would not be included, unless separate. While the internal HDD 2514 is illustrated as located within the computer 2502, the internal HDD 2514 can also be configured for external use in a suitable chassis (not shown). Additionally, while not shown in environment 2500, a solid state drive (SSD) could be used in addition to, or in place of, an HDD 2514. The HDD 2514, external storage device(s) 2516 and drive 2520 can be connected to the system bus 2508 by an HDD interface 2524, an external storage interface 2526 and a drive interface 2528, respectively. The interface 2524 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 2502, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 2512, including an operating system 2530, one or more application programs 2532, other program modules 2534 and program data 2536. All or portions of the operating system, applications, modules, or data can also be cached in the RAM 2512. The systems and methods described herein can be implemented utilizing various commercially available operating systems or combinations of operating systems.

Computer 2502 can optionally comprise emulation technologies. For example, a hypervisor (not shown) or other intermediary can emulate a hardware environment for operating system 2530, and the emulated hardware can optionally be different from the hardware illustrated in FIG. 25. In such an embodiment, operating system 2530 can comprise one virtual machine (VM) of multiple VMs hosted at computer 2502. Furthermore, operating system 2530 can provide runtime environments, such as the Java runtime environment or the .NET framework, for applications 2532. Runtime environments are consistent execution environments that allow applications 2532 to run on any operating system that includes the runtime environment. Similarly, operating system 2530 can support containers, and applications 2532 can be in the form of containers, which are lightweight, standalone, executable packages of software that include, e.g., code, runtime, system tools, system libraries and settings for an application.

Further, computer 2502 can be enable with a security module, such as a trusted processing module (TPM). For instance with a TPM, boot components hash next in time boot components, and wait for a match of results to secured values, before loading a next boot component. This process can take place at any layer in the code execution stack of computer 2502, e.g., applied at the application execution level or at the operating system (OS) kernel level, thereby enabling security at any level of code execution.

A user can enter commands and information into the computer 2502 through one or more wired/wireless input devices, e.g., a keyboard 2538, a touch screen 2540, and a pointing device, such as a mouse 2542. Other input devices (not shown) can include a microphone, an infrared (IR) remote control, a radio frequency (RF) remote control, or other remote control, a joystick, a virtual reality controller or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 2504 through an input device interface 2544 that can be coupled to the system bus 2508, but can be connected by other interfaces, such as a parallel port, an IEEE 1394 serial port, a game port, a USB port, an IR interface, a BLUETOOTH® interface, etc.

A monitor 2546 or other type of display device can be also connected to the system bus 2508 via an interface, such as a video adapter 2548. In addition to the monitor 2546, a computer typically includes other peripheral output devices (not shown), such as speakers, printers, etc.

The computer 2502 can operate in a networked environment using logical connections via wired or wireless communications to one or more remote computers, such as a remote computer(s) 2550. The remote computer(s) 2550 can be a workstation, a server computer, a router, a personal computer, portable computer, microprocessor-based entertainment appliance, a peer device or other common network node, and typically includes many or all of the elements described relative to the computer 2502, although, for purposes of brevity, only a memory/storage device 2552 is illustrated. The logical connections depicted include wired/wireless connectivity to a local area network (LAN) 2554 or larger networks, e.g., a wide area network (WAN) 2556. Such LAN and WAN networking environments are commonplace in offices and companies, and facilitate enterprise-wide computer networks, such as intranets, all of which can connect to a global communications network, e.g., the Internet.

When used in a LAN networking environment, the computer 2502 can be connected to the local network 2554 through a wired and/or wireless communication network interface or adapter 2558. The adapter 2558 can facilitate wired or wireless communication to the LAN 2554, which can also include a wireless access point (AP) disposed thereon for communicating with the adapter 2558 in a wireless mode.

When used in a WAN networking environment, the computer 2502 can include a modem 2560 or can be connected to a communications server on the WAN 2556 via other means for establishing communications over the WAN 2556, such as by way of the Internet. The modem 2560, which can be internal or external and a wired or wireless device, can be connected to the system bus 2508 via the input device interface 2544. In a networked environment, program modules depicted relative to the computer 2502 or portions thereof, can be stored in the remote memory/storage device 2552. It will be appreciated that the network connections shown are example and other means of establishing a communications link between the computers can be used.

When used in either a LAN or WAN networking environment, the computer 2502 can access cloud storage systems or other network-based storage systems in addition to, or in place of, external storage devices 2516 as described above, such as but not limited to a network virtual machine providing one or more aspects of storage or processing of information. Generally, a connection between the computer 2502 and a cloud storage system can be established over a LAN 2554 or WAN 2556 e.g., by the adapter 2558 or modem 2560, respectively. Upon connecting the computer 2502 to an associated cloud storage system, the external storage interface 2526 can, with the aid of the adapter 2558 or modem 2560, manage storage provided by the cloud storage system as it would other types of external storage. For instance, the external storage interface 2526 can be configured to provide access to cloud storage sources as if those sources were physically connected to the computer 2502.

The computer 2502 can be operable to communicate with any wireless devices or entities operatively disposed in wireless communication, e.g., a printer, scanner, desktop or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

FIG. 26 is a schematic block diagram of a sample computing environment 2600 with which the disclosed subject matter can interact. The sample computing environment 2600 includes one or more client(s) 2610. The client(s) 2610 can be hardware or software (e.g., threads, processes, computing devices). The sample computing environment 2600 also includes one or more server(s) 2630. The server(s) 2630 can also be hardware or software (e.g., threads, processes, computing devices). The servers 2630 can house threads to perform transformations by employing one or more embodiments as described herein, for example. One possible communication between a client 2610 and a server 2630 can be in the form of a data packet adapted to be transmitted between two or more computer processes. The sample computing environment 2600 includes a communication framework 2650 that can be employed to facilitate communications between the client(s) 2610 and the server(s) 2630. The client(s) 2610 are operably connected to one or more client data store(s) 2620 that can be employed to store information local to the client(s) 2610. Similarly, the server(s) 2630 are operably connected to one or more server data store(s) 2640 that can be employed to store information local to the servers 2630.

Various embodiments may be a system, a method, an apparatus or a computer program product at any possible technical detail level of integration. The computer program product can include a computer readable storage medium (or media) having computer readable program instructions thereon for causing a processor to carry out aspects of various embodiments. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network or a wireless network. The network can comprise copper transmission cables, optical transmission fibers, wireless transmission, routers, firewalls, switches, gateway computers or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform various aspects.

Various aspects are described herein with reference to flowchart illustrations or block diagrams of methods, apparatus (systems), and computer program products according to various embodiments. It will be understood that each block of the flowchart illustrations or block diagrams, and combinations of blocks in the flowchart illustrations or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer readable program instructions can also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart or block diagram block or blocks.

The flowcharts and block diagrams in the Figures illustrate the architecture, functionality, and operation of possible implementations of systems, methods, and computer program products according to various embodiments. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer or computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that various aspects can be practiced with other computer system configurations, including single-processor or multi-processor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. In another example, respective components can execute from various computer readable media having various data structures stored thereon. The components can communicate via local or remote processes such as in accordance with a signal having one or more data packets (e.g., data from one component interacting with another component in a local system, distributed system, or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. As used herein, the term "and/or" is intended to have the same meaning as "or." Moreover, articles "a" and "an" as used in the subject specification and annexed drawings should generally be construed to mean "one or more" unless specified otherwise or clear from context to be directed to a singular form. As used herein, the terms "example" or "exemplary" are utilized to mean serving as an example, instance, or illustration. For the avoidance of doubt, the subject matter disclosed herein is not limited by such examples. In addition, any aspect or design described herein as an "example" or "exemplary" is not necessarily to be construed as preferred or advantageous over other aspects or designs, nor is it meant to preclude equivalent exemplary structures and techniques known to those of ordinary skill in the art.

The herein disclosure describes non-limiting examples. For ease of description or explanation, various portions of the herein disclosure utilize the term "each," "every," or "all" when discussing various examples. Such usages of the term "each," "every," or "all" are non-limiting. In other words, when the herein disclosure provides a description that is applied to "each," "every," or "all" of some particular object or component, it should be understood that this is a non-limiting example, and it should be further understood that, in various other examples, it can be the case that such description applies to fewer than "each," "every," or "all" of that particular object or component.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:

a processor that executes computer-executable instructions stored in a non-transitory computer-readable memory, wherein execution of the computer-executable instructions causes the processor to perform operations comprising:

electronically accessing a first medical imaging scanner and a second medical imaging scanner, wherein the first medical imaging scanner and the second medical imaging scanner are of different image-capture modalities; and electronically performing imaging protocol management across the first medical imaging scanner and the second medical imaging scanner, wherein the imaging protocol management comprises:

determining, by the processor and in response to registration of the first medical imaging scanner, whether or not any other medical imaging scanner is electronically coupled to or is within a threshold proximity of the first medical imaging scanner;

designating, by the processor, in response to a determination that the second medical imaging scanner is electronically coupled to or is within the threshold proximity of the first medical imaging scanner, and on a graphical user interface, the first medical imaging scanner and the second medical imaging scanner as collectively forming a hybrid-modality setup;

determining, by the processor, whether or not the second medical imaging scanner is already registered; and prompting, by the processor, via the graphical user interface, and in response to a determination that the second medical imaging scanner is not already registered, registration of the second medical imaging scanner.

2. The system of claim 1, wherein the imaging protocol management comprises:

pulling, by the processor and from the first medical imaging scanner, one or more first imaging protocol files, a first link file, and one or more first locally-available computing resources;

pulling, by the processor and from the second medical imaging scanner, one or more second imaging protocol files and one or more second locally-available computing resources;

for each dependency referenced in the one or more first imaging protocol files and in the first link file:

determining, by the processor, whether or not the dependency, and its child dependencies, is satisfied by the one or more first locally-available computing resources, by the one or more second imaging protocol files, or by the one or more second locally-available computing resources;

designating, by the processor and on a graphical user interface, the dependency as broken, in response to a determination that the dependency, or any of its child dependencies, is not satisfied by the one or more first locally-available computing resources, by the one or more second imaging protocol files, or by the one or more second locally-available computing resources; and designating, by the processor and on the graphical user interface, that dependency as valid, in response to a determination that the dependency, and all of its child dependencies, is satisfied by the one or more first locally-available computing resources, by the one or more second imaging protocol files, or by the one or more second locally-available computing resources;

for each dependency referenced in the one or more first imaging protocol files but not referenced in the first link file, designating, by the processor and on the graphical user interface, the dependency as broken; and for each dependency referenced in the first link file but not referenced in the one or more first imaging protocol files, designating, by the processor and on the graphical user interface, the dependency as valid but unused.

3. The system of claim 1, wherein the imaging protocol management comprises:

identifying, by the processor, a hybrid-modality imaging protocol transaction, wherein the hybrid-modality imaging protocol transaction comprises a first imaging protocol file corresponding to the first medical imaging scanner and a second imaging protocol file corresponding to the second medical imaging scanner;

pushing, by the processor, the hybrid-modality imaging protocol transaction to the first medical imaging scanner and to the second medical imaging scanner;

determining, by the processor, whether or not the first imaging protocol file references the second imaging protocol file as a dependency;

requesting, by the processor and in response to a determination that the first imaging protocol file references the second imaging protocol file as a dependency, that the second medical imaging scanner commit the hybrid-modality imaging protocol transaction; and requesting, by the processor and in response to a notification from the second medical imaging scanner indicating that the hybrid-modality imaging protocol transaction has been successfully committed, that the first medical imaging scanner commit the hybrid-modality imaging protocol transaction.

4. The system of claim 1, wherein the imaging protocol management comprises:

pushing, by the processor, an imaging protocol file to the second medical imaging scanner;

determining, by the processor, whether or not the imaging protocol file references as a dependency, or is referenced as a dependency by, any other imaging protocol file; and instructing, by the processor and in response to a determination that the imaging protocol file references as a dependency, or is referenced as a dependency by, another imaging protocol file, the second medical imaging scanner to locally mark the imaging protocol file as belonging to a hybrid-modality imaging protocol transaction.

5. The system of claim 1, wherein the imaging protocol management comprises:

identifying, by the processor, a hybrid-modality imaging protocol transaction to be restored on the first medical imaging scanner and the second medical imaging scanner, wherein the hybrid-modality imaging protocol transaction comprises a first imaging protocol file performable by the first medical imaging scanner and a second imaging protocol file performable by the second medical imaging scanner;

determining, by the processor, whether or not the first imaging protocol file references the second imaging protocol file as a dependency;

requesting, by the processor and in response to a determination that the first imaging protocol file references the second imaging protocol file as a dependency, that the first medical imaging scanner restore the hybrid-modality imaging protocol transaction; and requesting, by the processor and in response to a notification from the first medical imaging scanner indicating that the hybrid-modality imaging protocol transaction has been successfully restored, that the second medical imaging scanner restore the hybrid-modality imaging protocol transaction.

6. The system of claim 1, wherein the imaging protocol management comprises:

accessing, by the processor, a request to launch an editor associated with the first medical imaging scanner;

launching, by the processor and in response to the request, the editor associated with the first medical imaging scanner and another editor associated with the second medical imaging scanner.

7. The system of claim 1, wherein the imaging protocol management comprises:

identifying, by the processor, a first imaging protocol file that references as a dependency a second imaging protocol file, wherein the first imaging protocol file is performable on the first medical imaging scanner, and wherein the second imaging protocol file corresponds to the second medical imaging scanner;

determining, by the processor, whether or not the second imaging protocol file is performable on the second medical imaging scanner;

substituting, by the processor and in response to a determination that the second imaging protocol file is not performable on the second medical imaging scanner, the second imaging protocol file with a third imaging protocol file that is clinically related to the second imaging protocol file and that is performable on the second medical imaging scanner; and pushing, by the processor, the first imaging protocol file and the third imaging protocol file to the first medical imaging scanner and to the second medical imaging scanner, respectively.

8. A computer-implemented method, comprising:

electronically accessing, by a processor, a first medical imaging scanner and a second medical imaging scanner, wherein the first medical imaging scanner and the second medical imaging scanner are of different image-capture modalities; and electronically performing, by the processor, imaging protocol management across the first medical imaging scanner and the second medical imaging scanner, wherein the imaging protocol management comprises:

pulling, by the processor and from the first medical imaging scanner, one or more first imaging protocol files, a first link file, and one or more first locally-available computing resources;

pulling, by the processor and from the second medical imaging scanner, one or more second imaging protocol files and one or more second locally-available computing resources;

for each dependency referenced in the one or more first imaging protocol files and in the first link file:

determining, by the processor, whether or not the dependency, and its child dependencies, is satisfied by the one or more first locally-available computing resources, by the one or more second imaging protocol files, or by the one or more second locally-available computing resources;

designating, by the processor and on a graphical user interface, the dependency as broken, in response to a determination that the dependency, or any of its child dependencies, is not satisfied by the one or more first locally-available computing resources, by the one or more second imaging protocol files, or by the one or more second locally-available computing resources; and designating, by the processor and on the graphical user interface, that dependency as valid, in response to a determination that the dependency, and all of its child dependencies, is satisfied by the one or more first locally-available computing resources, by the one or more second imaging protocol files, or by the one or more second locally-available computing resources;

for each dependency referenced in the one or more first imaging protocol files but not referenced in the first link file, designating, by the processor and on the graphical user interface, the dependency as broken; and for each dependency referenced in the first link file but not referenced in the one or more first imaging protocol files, designating, by the processor and on the graphical user interface, the dependency as valid but unused.

9. The computer-implemented method of claim 8, wherein the imaging protocol management comprises:

determining, by the processor and in response to registration of the first medical imaging scanner, whether or not any other medical imaging scanner is electronically coupled to or is within a threshold proximity of the first medical imaging scanner;

designating, by the processor, in response to a determination that the second medical imaging scanner is electronically coupled to or is within the threshold proximity of the first medical imaging scanner, and on a graphical user interface, the first medical imaging scanner and the second medical imaging scanner as collectively forming a hybrid-modality setup;

determining, by the processor, whether or not the second medical imaging scanner is already registered; and prompting, by the processor, via the graphical user interface, and in response to a determination that the second medical imaging scanner is not already registered, registration of the second medical imaging scanner.

10. The computer-implemented method of claim 8, wherein the imaging protocol management comprises:

identifying, by the processor, a hybrid-modality imaging protocol transaction, wherein the hybrid-modality imaging protocol transaction comprises a first imaging protocol file corresponding to the first medical imaging scanner and a second imaging protocol file corresponding to the second medical imaging scanner;

pushing, by the processor, the hybrid-modality imaging protocol transaction to the first medical imaging scanner and to the second medical imaging scanner;

determining, by the processor, whether or not the first imaging protocol file references the second imaging protocol file as a dependency;

requesting, by the processor and in response to a determination that the first imaging protocol file references the second imaging protocol file as a dependency, that the second medical imaging scanner commit the hybrid-modality imaging protocol transaction; and requesting, by the processor and in response to a notification from the second medical imaging scanner indicating that the hybrid-modality imaging protocol transaction has been successfully committed, that the first medical imaging scanner commit the hybrid-modality imaging protocol transaction.

11. The computer-implemented method of claim 8, wherein the imaging protocol management comprises:

pushing, by the processor, an imaging protocol file to the second medical imaging scanner;

determining, by the processor, whether or not the imaging protocol file references as a dependency, or is referenced as a dependency by, any other imaging protocol file; and instructing, by the processor and in response to a determination that the imaging protocol file references as a dependency, or is referenced as a dependency by, another imaging protocol file, the second medical imaging scanner to locally mark the imaging protocol file as belonging to a hybrid-modality imaging protocol transaction.

12. The computer-implemented method of claim 8, wherein the imaging protocol management comprises:

identifying, by the processor, a hybrid-modality imaging protocol transaction to be restored on the first medical imaging scanner and the second medical imaging scanner, wherein the hybrid-modality imaging protocol transaction comprises a first imaging protocol file performable by the first medical imaging scanner and a second imaging protocol file performable by the second medical imaging scanner;

determining, by the processor, whether or not the first imaging protocol file references the second imaging protocol file as a dependency;

requesting, by the processor and in response to a determination that the first imaging protocol file references the second imaging protocol file as a dependency, that the first medical imaging scanner restore the hybrid-modality imaging protocol transaction; and requesting, by the processor and in response to a notification from the first medical imaging scanner indicating that the hybrid-modality imaging protocol transaction has been successfully restored, that the second medical imaging scanner restore the hybrid-modality imaging protocol transaction.

13. The computer-implemented method of claim 8, wherein the imaging protocol management comprises:

accessing, by the processor, a request to launch an editor associated with the first medical imaging scanner;

launching, by the processor and in response to the request, the editor associated with the first medical imaging scanner and another editor associated with the second medical imaging scanner.

14. The computer-implemented method of claim 8, wherein the imaging protocol management comprises:

identifying, by the processor, a first imaging protocol file that references as a dependency a second imaging protocol file, wherein the first imaging protocol file is performable on the first medical imaging scanner, and wherein the second imaging protocol file corresponds to the second medical imaging scanner;

determining, by the processor, whether or not the second imaging protocol file is performable on the second medical imaging scanner;

substituting, by the processor and in response to a determination that the second imaging protocol file is not performable on the second medical imaging scanner, the second imaging protocol file with a third imaging protocol file that is clinically related to the second imaging protocol file and that is performable on the second medical imaging scanner; and pushing, by the processor, the first imaging protocol file and the third imaging protocol file to the first medical imaging scanner and to the second medical imaging scanner, respectively.

15. A computer program product for facilitating automated imaging protocol management for hybrid modalities, the computer program product comprising a non-transitory computer-readable memory having program instructions embodied therewith, the program instructions executable by a processor to cause the processor to:

electronically access a first medical imaging scanner and a second medical imaging scanner, wherein the first medical imaging scanner and the second medical imaging scanner are of different image-capture modalities; and electronically perform imaging protocol management across the first medical imaging scanner and the second medical imaging scanner, wherein the imaging protocol management comprises:

identifying, by the processor, a hybrid-modality imaging protocol transaction, wherein the hybrid-modality imaging protocol transaction comprises a first imaging protocol file corresponding to the first medical imaging scanner and a second imaging protocol file corresponding to the second medical imaging scanner;

pushing, by the processor, the hybrid-modality imaging protocol transaction to the first medical imaging scanner and to the second medical imaging scanner;

determining, by the processor, whether or not the first imaging protocol file references the second imaging protocol file as a dependency;

requesting, by the processor and in response to a determination that the first imaging protocol file references the second imaging protocol file as a dependency, that the second medical imaging scanner commit the hybrid-modality imaging protocol transaction; and requesting, by the processor and in response to a notification from the second medical imaging scanner indicating that the hybrid-modality imaging protocol transaction has been successfully committed, that the first medical imaging scanner commit the hybrid-modality imaging protocol transaction.

16. The computer program product of claim 15, wherein the imaging protocol management comprises hybrid-aware scanner registration.

17. The computer program product of claim 15, wherein the imaging protocol management comprises hybrid-aware detection of broken protocol dependencies.

18. The computer program product of claim 15, wherein the imaging protocol management comprises hybrid-aware commit operations or hybrid-aware restore operations.

* * * * *